(12) United States Patent
Biadatti et al.

(10) Patent No.: US 8,470,871 B2
(45) Date of Patent: *Jun. 25, 2013

(54) LIGANDS THAT MODULATE RAR RECEPTORS

(75) Inventors: Thibaud Biadatti, Opio (FR); Laurence Dumais, Le Rouret (FR); Catherine Soulet, Antibes (FR); Sandrine Talano, Vence (FR); Sebastien Daver, Antibes (FR)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/527,299

(22) Filed: Jun. 19, 2012

(65) Prior Publication Data

US 2012/0258996 A1   Oct. 11, 2012

Related U.S. Application Data

(60) Continuation of application No. 12/842,347, filed on Jul. 23, 2010, now Pat. No. 8,227,507, which is a division of application No. 11/819,068, filed on Jun. 25, 2007, now Pat. No. 7,807,708, which is a continuation of application No. PCT/EP2005/014217, filed on Dec. 21, 2005.

(60) Provisional application No. 60/647,383, filed on Jan. 28, 2005.

(30) Foreign Application Priority Data

Dec. 23, 2004  (FR) ..................... 04/13848

(51) Int. Cl.
| | |
|---|---|
| A61K 31/235 | (2006.01) |
| A61K 31/196 | (2006.01) |
| A61K 31/40 | (2006.01) |
| C07C 229/64 | (2006.01) |
| C07C 229/66 | (2006.01) |
| C07D 207/08 | (2006.01) |

(52) U.S. Cl.
USPC ........... 514/428; 514/530; 514/531; 514/539; 514/563; 514/567; 548/573; 560/43; 562/452

(58) Field of Classification Search
USPC .. 514/428, 530, 531, 539, 563, 567; 548/573; 560/43; 562/452
See application file for complete search history.

(56) References Cited

U.S. PATENT DOCUMENTS 6,150,413 A * 11/2000 Bernardon et al. ........... 514/568
6,649,612 B1    11/2003 Bernardon et al.

FOREIGN PATENT DOCUMENTS

WO    WO 99/10308 A1   3/1999

OTHER PUBLICATIONS

Sakuta et al. "Comedolytic effect of a novel RARγ-specific retinoid, ER36009: comparison with retinoic acid in the rhino mouse model" *European Journal of Dermatology*, 2006, vol. 15, No. 6, pp. 459-464.
Napgal et al. "Recent Developments in Receptor-Selective Retinoids" *Current Pharmaceutical Design*, 2000, vol. 6, No. 9, pp. 919-931.
International Search Report for corresponding PCT/EP2005/014217 dated Mar. 28, 2006.

* cited by examiner

*Primary Examiner* — Joseph Kosack
(74) *Attorney, Agent, or Firm* — Dentons US LLP

(57) ABSTRACT

Novel ligand compounds having the general formula (I):

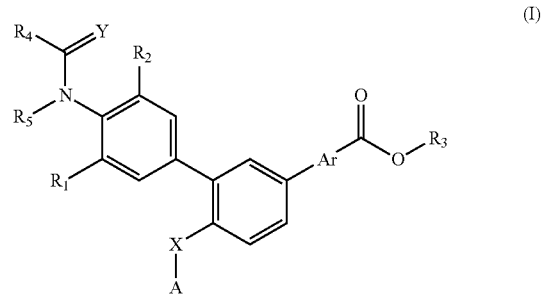

and pharmaceutical/cosmetic compositions comprised thereof are useful in human and veterinary medicine or, alternatively, in cosmetics.

21 Claims, 3 Drawing Sheets

LIGANDS THAT MODULATE RAR RECEPTORS

CROSS-REFERENCE TO EARLIER APPLICATIONS

This application is a continuation of U.S. application Ser. No. 12/842,347 filed Jul. 23, 2010, now U.S. Pat. No. 8,227,507, which is a division of U.S. application Ser. No. 11/819,068 filed Jun. 25, 2007, now U.S. Pat. No. 7,807,708, which is a continuation of PCT/EP2005/014217 filed Dec. 21, 2005 and designating the United States, published in the English language as WO 2006/066978 A1 on Jun. 29, 2006, which claims priority under 35 U.S.C. §119 of FR 0413848, filed Dec. 23, 2004, and benefit of Provisional Application No. 60/647,383, filed Jan. 28, 2005, each hereby expressly incorporated by reference in its entirety and each assigned to the assignee hereof.

BACKGROUND OF THE INVENTION

1. Technical Field of the Invention

The present invention relates to novel ligand compounds as useful industrial products, which are ligands that modulate RAR receptors. This invention also relates to compositions comprised thereof, to processes for the preparation of same and to their formulation into pharmaceutical compositions useful in human or veterinary medicine, or alternatively, into cosmetic compositions, and to the non-therapeutic applications of these compositions.

2. Description of Background and/or Related and/or Prior Art

Compounds with activity of retinoid type (vitamin A and its derivatives) are widely described in the literature as having activity in cell proliferation and differentiation processes. These properties give this class of compounds great potential in the treatment or prevention of numerous pathologies, and more particularly in dermatology and cancer. Many biological effects of retinoids are mediated by modulating the nuclear retinoic acid receptors (RAR).

The RAR receptors activate transcription by binding to DNA sequence elements, known as RAR response elements (RARE), in the form of a heterodimer with the retinoid X receptors (known as RXRs).

Three subtypes of human RARs have been identified and described: RARα, RARβ and RARγ.

The prior art described a large number of chemical compounds that are RAR type receptor ligands. In the prior art, examples include U.S. Pat. No. 6,150,413, which describes triaromatic compounds, U.S. Pat. No. 6,214,878, which describes stilbene compounds, and U.S. Pat. No. 6,218,128, which describes a family of bicyclic or tricyclic molecules.

SUMMARY OF THE INVENTION

Novel compounds that modulate retinoic acid receptors have now been developed.

Thus, the present invention features compounds having the general formula (I) below:

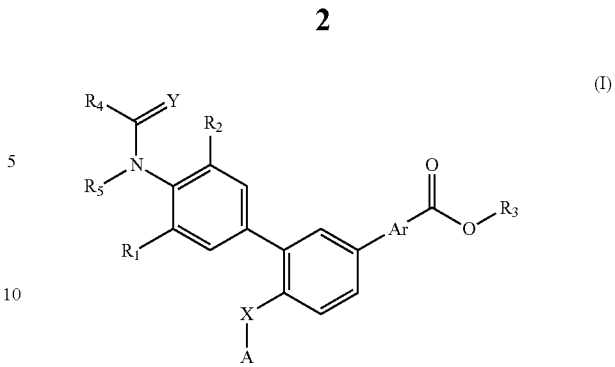

in which:

$R_1$ is a hydrogen atom, an alkyl radical of 1 to 4 carbon atoms or a —$CF_3$ radical;

$R_2$ is a hydrogen atom, an alkyl or alkoxy radical of 1 to 4 carbon atoms or a chlorine atom;

$R_3$ is a hydrogen atom, a linear or branched alkyl or alkoxy radical of 1 to 10 carbon atoms and preferably 1 to 6 carbon atoms optionally substituted with a methoxy group, or alternatively a linear or branched alkyl radical of 1 to 10 carbon atoms and preferably 1 to 6 carbon atoms containing an ether function;

$R_4$ is a hydrogen atom or an alkyl radical of 1 to 3 carbon atoms;

$R_5$ is a hydrogen atom or an alkyl radical of 1 to 3 carbon atoms;

or alternatively $R_4$ and $R_5$ form, together with the bond —N—C(=Y)—, a pyrrolidine, pyrrolidinone, piperidine or piperidinone ring;

Y is two hydrogen atoms or a hetero atom, for example oxygen or sulfur;

Ar is a 1,4-phenyl, 2,5-pyridyl, 5,2-pyridyl or 2,5-thiophenyl ring;

X is an oxygen atom optionally substituted with an alkyl or alkylamine radical or a C—C single bond;

A is a hydrogen atom or the following formula:

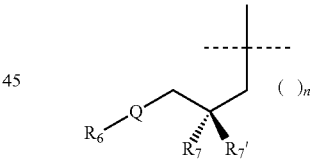

in which:

Q is an oxygen atom or an —NH— bond;

$R_6$ is a hydrogen atom, an alkyl radical of 1 to 6 carbon atoms, a cycloalkyl radical of 3 to 6 carbon atoms or a —C(O)$CH_3$ or —C(O)$CH_2CH_3$ radical;

$R_7$ and $R_{7'}$ represent, independently of each other, a hydrogen atom or a hydroxyl group, with the proviso that $R_7$ and $R_{7'}$ are not simultaneously a hydroxyl group;

n is 0, 1, 2, 3, 4 or 5;

and the salts of the compounds of formula (I) when $R_3$ is a hydrogen atom, and also the geometrical isomers of the said compounds of formula (I).

Figure 1:
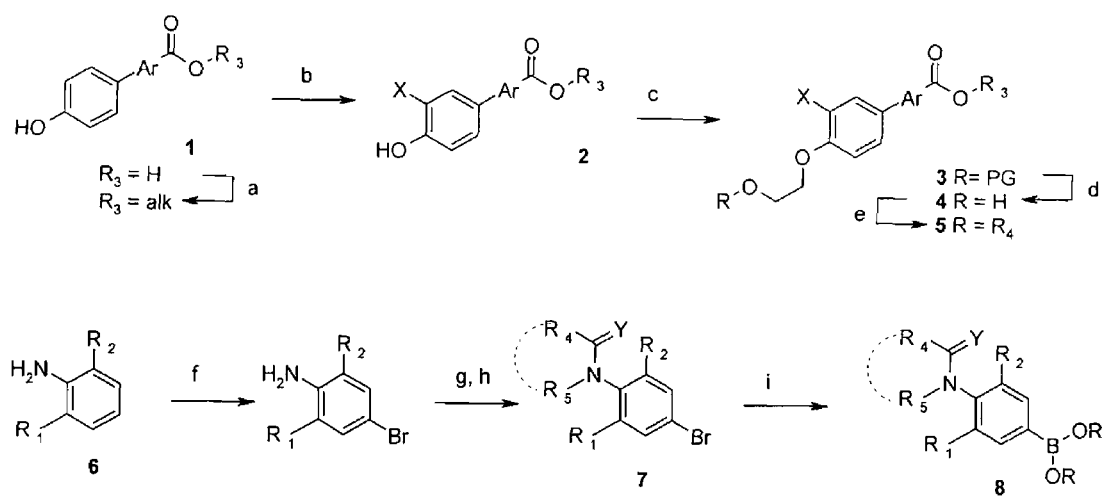
FIGS. 1-3 show a variety of reaction schemes for the ultimate preparation of the ligand compounds according to the invention.

DETAILED DESCRIPTION OF BEST MODE AND SPECIFIC/PREFERRED EMBODIMENTS OF THE INVENTION

When the compounds according to the invention are in the form of a salt, it is preferably an alkali metal or alkaline-earth metal salt, or alternatively a zinc salt or a salt of an organic amine or of an acidic partner when the compound is itself basic.

According to the present invention, the alkyl radicals of 1 to 3 carbon atoms are preferably selected from among methyl, ethyl, i-propyl and n-propyl radicals.

According to the present invention, the alkyl radicals of 1 to 4 carbon atoms are preferably selected from among methyl, ethyl, i-propyl, butyl and t-butyl radicals.

According to the present invention, the alkyl radicals of 1 to 6 carbon atoms are preferably selected from among methyl, ethyl, propyl, i-propyl, butyl, i-butyl, t-butyl, pentyl and hexyl.

According to the present invention, the alkyl radicals of 1 to 10 carbon atoms are linear or branched chains preferably selected from among methyl, ethyl, propyl, i-propyl, butyl, i-butyl, t-butyl, pentyl, hexyl, heptyl, octyl, nonyl and dodecyl.

The term "alkoxy radical having from 1 to 10 carbon atoms" means an alkyl radical having from 1 to 10 carbon atoms linked to the rest of the molecule via an oxygen atom. Preferably, the alkoxy radical is selected from among methoxy, ethoxy, isopropyloxy, tert-butoxy and hexyloxy radicals.

Similarly, the term "alkoxy radical having from 1 to 6 carbon atoms" means an alkyl radical having from 1 to 6 carbon atoms linked to the rest of the molecule via an oxygen atom. Preferably, the alkoxy radical is selected from among methoxy, ethoxy, isopropyloxy, tert-butoxy and hexyloxy radicals.

Finally, the term "alkoxy radical having from 1 to 4 carbon atoms" means an alkyl radical having from 1 to 4 carbon atoms linked to the rest of the molecule via an oxygen atom. Preferably, the alkoxy radical is selected from among methoxy, ethoxy, isopropyloxy and tert-butoxy radicals.

According to the present invention, the cycloalkyl radicals of 3 to 6 carbon atoms are preferably selected from among cyclopropyl, cyclopentyl and cyclohexyl.

According to the present invention, the compounds of formula (I) that are more particularly preferred are those for which at least one, and preferably all, of the conditions below are satisfied:

$R_1$ is a hydrogen atom or a t-butyl or i-propyl radical;
$R_2$ is a hydrogen atom or a t-butyl or i-propyl radical;
$R_3$ is a hydrogen atom or an ethyl radical;
$R_4$ and $R_5$ are, independently of each other, a methyl or ethyl radical or together form a pyrrolidine ring;
A is as defined above in which $R_6$ is a hydrogen atom, an i-propyl or t-butyl radical, a cycloalkyl radical of 3 to 6 carbon atoms or a —C(O)CH$_3$ or —C(O)CH$_2$CH$_3$ radical.

Among the compounds of formula (I) according to the present invention, especially representative are the following compounds:

1. ethyl 3"-tert-butyl-4"-diethylamino-4'-hydroxy[1,1';3',1"]terphenyl-4-carboxylate,
2. ethyl 3"-tert-butyl-4"-diethylamino-4'-(4-hydroxybutoxy)-[1,1';3',1"]terphenyl-4-carboxylate,
3. 3"-tert-butyl-4"-diethylamino-4'-(4-hydroxybutoxy)-[1,1';3',1"]terphenyl-4-carboxylic acid,
4. ethyl 4"-(acetylethylamino)-3"-tert-butyl-4'-(4-hydroxybutoxy)-[1,1';3',1"]terphenyl-4-carboxylate,
5. 4"-(acetylethylamino)-3"-tert-butyl-4'-(4-hydroxybutoxy)-[1,1';3',1"]terphenyl-4-carboxylic acid,
6. 3"-tert-butyl-4"-diethylamino-4'-(2-hydroxyethoxy)-[1,1'; 3',1"]terphenyl-4-carboxylic acid,
7. ethyl 3"-tert-butyl-4"-diethylamino-4'-(3-hydroxypropoxy)-[1,1';3',1"]terphenyl-4-carboxylate,
8. 3"-tert-butyl-4"-diethylamino-4'-(3-hydroxypropoxy)-[1,1';3',1"]terphenyl-4-carboxylic acid,
9. ethyl 4"-diethylamino-4'-(3-hydroxypropoxy)-[1,1';3',1"]terphenyl-4-carboxylate,
10. 4"-diethylamino-4'-(3-hydroxypropoxy)-[1,1';3',1"]terphenyl-4-carboxylic acid,
11. ethyl 4"-diethylamino-3"-ethyl-4'-(3-hydroxypropoxy)-[1,1';3',1"]terphenyl-4-carboxylate,
12. 4"-diethylamino-3"-ethyl-4'-(3-hydroxypropoxy)-[1,1'; 3',1"]terphenyl-4-carboxylic acid,
13. 4"-diethylamino-3"-ethyl-4'-(2-hydroxyethoxy)[1,1';3', 1"]terphenyl-4-carboxylic acid,
14. ethyl 4"-diethylamino-3"-ethyl-4'-(2-hydroxyethoxy)-[1, 1';3',1"]terphenyl-4-carboxylate,
15. 3"-tert-butyl-4"-diethylamino-4'-(2-hydroxyethoxy)[1, 1';3',1"]terphenyl-4-carboxylate,
16. ethyl 4"-diethylamino-4'-(3-hydroxypropoxy)-3"-methyl [1,1';3',1"]terphenyl-4-carboxylate,
17. 4"-diethylamino-4'-(3-hydroxypropoxy)-3"-methyl[1,1'; 3',1"]terphenyl-4-carboxylic acid,
18. ethyl 3"-tert-butyl-4'-(4-hydroxybutoxy)-4"-pyrrolidin-1-yl[1,1';3',1"]terphenyl-4-carboxylate,
19. 3"-tert-butyl-4'-(4-hydroxybutoxy)-4"-pyrrolidin-1-yl[1, 1';3',1"]terphenyl-4-carboxylic acid,
20. ethyl 4'-(4-hydroxybutoxy)-4"-pyrrolidin-1-yl-3"-trifluoromethyl[1,1';3',1"]terphenyl-4-carboxylate,
21. 4'-(4-hydroxybutoxy)-4"-pyrrolidin-1-yl-3"-trifluoromethyl[1,1';3',1"]terphenyl-4-carboxylic acid,
22. ethyl 3"-tert-butyl-4'-(3-hydroxypropoxy)-4"-pyrrolidin-1-yl[1,1';3',1"]terphenyl-4-carboxylate,
23. 3"-tert-butyl-4'-(3-hydroxypropoxy)-4"-pyrrolidin-1-yl [1,1';3',1]terphenyl-4-carboxylic acid,
24. ethyl 3"-tert-butyl-4'-(2-hydroxyethoxy)-4"-pyrrolidin-1-yl[1,1';3',1"]terphenyl-4-carboxylate,
25. 3"-tert-butyl-4'-(2-hydroxyethoxy)-4"-pyrrolidin-1-yl[1, 1';3',1"]terphenyl-4-carboxylic acid,
26. 4'-(3-hydroxypropoxy)-4"-pyrrolidin-1-yl[1,1';3',1"]terphenyl-4-carboxylic acid,
27. 3"-tert-butyl-4"-diethylamino-4'-hydroxy[1,1';3',1"]terphenyl-4-carboxylic acid,
28. ethyl 4"-diethylamino-4'-hydroxy-3"-trifluoromethyl[1, 1';3',1"]terphenyl-4-carboxylate,
29. 4"-diethylamino-4'-hydroxy-3"-trifluoromethyl[1,1';3', 1"]terphenyl-4-carboxylic acid,
30. 3"-tert-butyl-4"-diethylamino-4'-(4-isopropylaminobutoxy)-[1,1';3',1"]terphenyl-4-carboxylic acid,
31. 3"-tert-butyl-4'-(4-isopropylaminobutoxy)-4"-pyrrolidin-1-yl[1,1';3',1"]terphenyl-4-carboxylic acid,
32. ethyl 3"-tert-butyl-4"-diethylamino-4'-(3-hydroxypropyl)-[1,1';3',1"]terphenyl-4-carboxylate,
33. 3"-tert-butyl-4"-diethylamino-4'-(3-hydroxypropyl)-[1, 1';3',1"]terphenyl-4-carboxylic acid,
34. ethyl 3"-tert-butyl-4"-diethylamino-4'-(2,3-dihydroxypropyl)-[1,1';3',1"]terphenyl-4-carboxylate,
35. 3"-tert-butyl-4"-diethylamino-4'-(2,3-dihydroxypropyl)-[1,1';3',1"]terphenyl-4-carboxylic acid,
36. ethyl 4"-(acetylethylamino)-3"-tert-butyl-4'-(3-hydroxypropyl)-[1,1';3',1"]terphenyl-4-carboxylate,
37. 4"-(acetylethylamino)-3"-tert-butyl-4'-(3-hydroxypropyl)-[1,1';3',1"]terphenyl-4-carboxylic acid, 38. ethyl 3"-tert-butyl-4'-(3-cyclopropylaminopropyl)-4"-diethylamino[1,1';3',1"]terphenyl-4-carboxylate,
39. 3"-tert-butyl-4'-(3-cyclopropylaminopropyl)-4"-diethylamino[1,1';3',1"]terphenyl-4-carboxylic acid,
40. ethyl 3"-tert-butyl-4'-(3-cyclopentylaminopropyl)-4"-diethylamino[1,1';3',1"]terphenyl-4-carboxylate,
41. 3"-tert-butyl-4'-(3-cyclopentylaminopropyl)-4"-diethylamino[1,1';3',1"]terphenyl-4-carboxylic acid,
42. ethyl 3"-tert-butyl-4'-(3-cyclohexylaminopropyl)-4"-diethylamino[1,1';3',1"]terphenyl-4-carboxylate,
43. 3"-tert-butyl-4'-(3-cyclohexylaminopropyl)-4"-diethylamino[1,1';3',1"]terphenyl-4-carboxylic acid,
44. ethyl 3"-tert-butyl-4'-(3-tert-butylaminopropyl)-4"-diethylamino[1,1';3',1"]terphenyl-4-carboxylate,
45. 3"-tert-butyl-4'-(3-tert-butylaminopropyl)-4"-diethylamino[1,1';3',1"]terphenyl-4-carboxylic acid,
46. ethyl 4"-(acetylethylamino)-3"-tert-butyl-4'-(3-cyclopropylaminopropyl)-[1,1';3',1"]terphenyl-4-carboxylate,
47. 4"-(acetylethylamino)-3"-tert-butyl-4'-(3-cyclopropylaminopropyl)-[1,1';3',1"]terphenyl-4-carboxylic acid,
48. ethyl 3"-tert-butyl-4"-diethylamino-4'-(3-isopropylaminopropyl)-[1,1';3',1"]terphenyl-4-carboxylate,
49. 3"-tert-butyl-4"-diethylamino-4'-(3-isopropylaminopropyl)-[1,1';3',1"]terphenyl-4-carboxylic acid,
50. ethyl 4'-(3-aminopropyl)-3"-tert-butyl-4"-diethylamino[1,1';3',1"]terphenyl-4-carboxylate,
51. 4'-(3-aminopropyl)-3"-tert-butyl-4"-diethylamino[1,1';3',1"]terphenyl-4-carboxylic acid,
52. [3"-tert-butyl-4-carboxy-4'-(3-hydroxypropyl)-[1,1';3',1"]terphenyl-4"-yl]diethylamine hydrochloride,
53. 3"-tert-butyl-4'-(2-hydroxyethoxy)-4"-(2-oxopyrrolidin-1-yl)-[1,1';3',1"]terphenyl-4-carboxylic acid,
54. 3"-tert-butyl-4"-ethylamino-4'-(3-hydroxypropoxy)-[1,1';3',1"]terphenyl-4-carboxylic acid,
55. 4'-(3-acetoxypropoxy)-3"-tert-butyl-4"-diethylamino[1,1';3',1"]terphenyl-4-carboxylic acid,
56. 3"-tert-butyl-4"-diethylamino-4'-(3-propionyloxypropoxy)-[1,1';3',1"]terphenyl-4-carboxylic acid,
57. methyl 3"-tert-butyl-4"-diethylamino-4'-(3-hydroxypropoxy)-[1,1';3',1"]terphenyl-4-carboxylate,
58. isopropyl 3"-tert-butyl-4"-diethylamino-4'-(3-hydroxypropoxy)-[1,1';3',1"]terphenyl-4-carboxylate,
59. isobutyl 3"-tert-butyl-4"-diethylamino-4'-(3-hydroxypropoxy)-[1,1';3',1"]terphenyl-4-carboxylate,
60. 3"-tert-butyl-4"-diethylamino-4'-(3-hydroxypropoxy)-5"-methyl[1,1';3',1"]terphenyl-4-carboxylic acid,
61. 4"-diethylamino-4'-(3-hydroxypropoxy)-3"-isopropyl-5"-methyl[1,1';3',1"]terphenyl-4-carboxylic acid,
62. 3"-tert-butyl-5"-chloro-4"-diethylamino-4'-(3-hydroxypropoxy)-[1,1';3',1"]terphenyl-4-carboxylic acid,
63. 4"-diethylamino-4'-(3-hydroxypropoxy)-3",5"-diisopropyl[1,1';3',1"]terphenyl-4-carboxylic acid,
64. 3",5"-di-tert-butyl-4"-diethylamino-4'-(3-hydroxypropoxy)-[1,1';3',1"]terphenyl-4-carboxylic acid,
65. 4"-diethylamino-4'-(3-hydroxypropoxy)-3"-trifluoromethyl[1,1';3',1"]terphenyl-4-carboxylic acid,
66. 3"-tert-butyl-4"-(ethylmethylamino)-4'-(2-hydroxyethoxy)-[1,1';3',1"]terphenyl-4-carboxylic acid,
67. 3"-tert-butyl-4"-dimethylamino-4'-(2-hydroxyethoxy)-[1,1';3',1"]terphenyl-4-carboxylic acid,
68. 3"-tert-butyl-4"-(ethylisopropylamino)-4'-(2-hydroxyethoxy)-[1,1';3',1"]terphenyl-4-carboxylic acid,
69. 3"-tert-butyl-4"-(ethylpropylamino)-4'-(2-hydroxyethoxy)-[1,1';3',1"]terphenyl-4-carboxylic acid,
70. 3"-tert-butyl-4"-dipropylamino-4'-(2-hydroxyethoxy)-[1,1';3',1"]terphenyl-4-carboxylic acid,
71. 3"-tert-butyl-4"-(ethylpropionylamino)-4'-(2-hydroxyethoxy)-[1,1';3',1"]terphenyl-4-carboxylic acid,
72. 6-[3'-tert-butyl-4-diethylamino-6-(2-hydroxyethoxy)biphenyl-3-yl]nicotinic acid,
73. 5-[3'-tert-butyl-4-diethylamino-6-(2-hydroxyethoxy)biphenyl-3-yl]pyridine-2-carboxylic acid,
74. 5-[3'-tert-butyl-4-diethylamino-6-(2-hydroxyethoxy)biphenyl-3-yl]thiophene-2-carboxylic acid,
75. 3"-tert-butyl-4'-(2-hydroxyethoxy)-5"-methyl-4"-pyrrolidin-1-yl[1,1';3',1"]terphenyl-4-carboxylic acid,
76. 3"-tert-butyl-5"-chloro-4'-(2-hydroxyethoxy)-4"-pyrrolidin-1-yl[1,1';3',1"]terphenyl-4-carboxylic acid,
77. 4'-(2-hydroxyethoxy)-3"-isopropyl-4"-pyrrolidin-1-yl[1,1';3',1"]terphenyl-4-carboxylic acid,
78. 3"-ethyl-4'-(2-hydroxyethoxy)-4"-pyrrolidin-1-yl[1,1';3',1"]terphenyl-4-carboxylic acid,
79. 4'-(2-hydroxyethoxy)-3",5"-diisopropyl-4"-pyrrolidin-1-yl[1,1';3',1"]terphenyl-4-carboxylic acid,
80. 3",5"-diethyl-4'-(2-hydroxyethoxy)-4"-pyrrolidin-1-yl[1,1';3',1"]terphenyl-4-carboxylic acid,
81. 3",5"-dimethyl-4'-(2-hydroxyethoxy)-4"-pyrrolidin-1-yl[1,1';3',1"]terphenyl-4-carboxylic acid,
82. 4'-(2-acetoxyethoxy)-3"-tert-butyl-4"-pyrrolidin-1-yl[1,1';3',1"]terphenyl-4-carboxylic acid,
83. 4'-(2-propionyloxyethoxy)-3"-tert-butyl-4"-pyrrolidin-1-yl[1,1';3',1"]terphenyl-4-carboxylic acid,
84. methyl 3"-tert-butyl-4'-(2-hydroxyethoxy)-4"-pyrrolidin-1-yl[1,1';3',1"]terphenyl-4-carboxylate,
85. isopropyl 3"-tert-butyl-4'-(2-hydroxyethoxy)-4"-pyrrolidin-1-yl[1,1';3',1"]terphenyl-4-carboxylate,
86. isobutyl 3"-tert-butyl-4'-(2-hydroxyethoxy)-4"-pyrrolidin-1-yl[1,1';3',1"]terphenyl-4-carboxylate,
87. ethyl 3"-tert-butyl-4'-(3-hydroxypropoxy)-4"-pyrrolidin-1-yl[1,1';3',1"]terphenyl-4-carboxylate,
88. ethyl 3"-tert-butyl-5"-chloro-4'-(2-hydroxyethoxy)-4"-pyrrolidin-1-yl[1,1';3',1"]terphenyl-4-carboxylate,
89. 6-[3'-tert-butyl-6-(2-hydroxyethoxy)-4'-pyrrolidin-1-yl-biphenyl-3-yl]nicotinic acid,
90. 5-[3'-tert-butyl-6-(2-hydroxyethoxy)-4'-pyrrolidin-1-yl-biphenyl-3-yl]pyridine-2-carboxylic acid,
91. ethyl 6-[3'-tert-butyl-6-(2-hydroxyethoxy)-4'-pyrrolidin-1-ylbiphenyl-3-yl]nicotinate,
92. ethyl 3"-tert-butyl-4'-(3-hydroxypropyl)-4"-pyrrolidin-1-yl[1,1';3',1"]terphenyl-4-carboxylate,
93. 3"-tert-butyl-4'-(3-hydroxypropyl)-4"-pyrrolidin-1-yl[1,1';3',1"]terphenyl-4-carboxylic acid,
94. 3"-tert-butyl-4'-(2-hydroxyethoxy)-4"-(2-oxopyrrolidin-1-yl)-[1,1';3',1"]terphenyl-4-carboxylic acid,
95. 3"-tert-butyl-4'-(2-hydroxyethoxy)-4"-(2-oxopiperid-1-yl)-[1,1';3',1"]terphenyl-4-carboxylic acid,
96. 3"-tert-butyl-4'-(2-hydroxyethoxy)-4"-piperid-1-yl[1,1';3',1"]terphenyl-4-carboxylic acid,
97. 5-[3'-tert-butyl-6-(2-hydroxyethoxy)-4'-pyrrolidin-1-yl-biphenyl-3-yl]thiophene-2-carboxylic acid.

Figure 2:
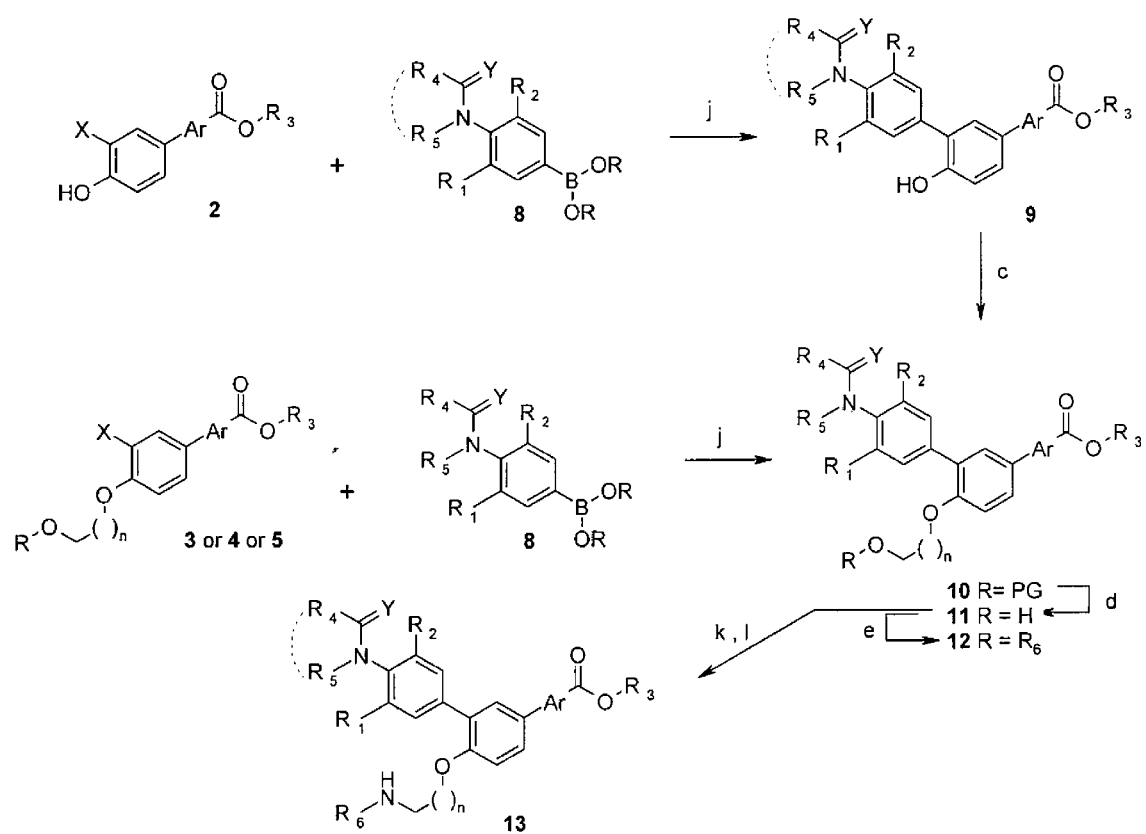
Figure 3:
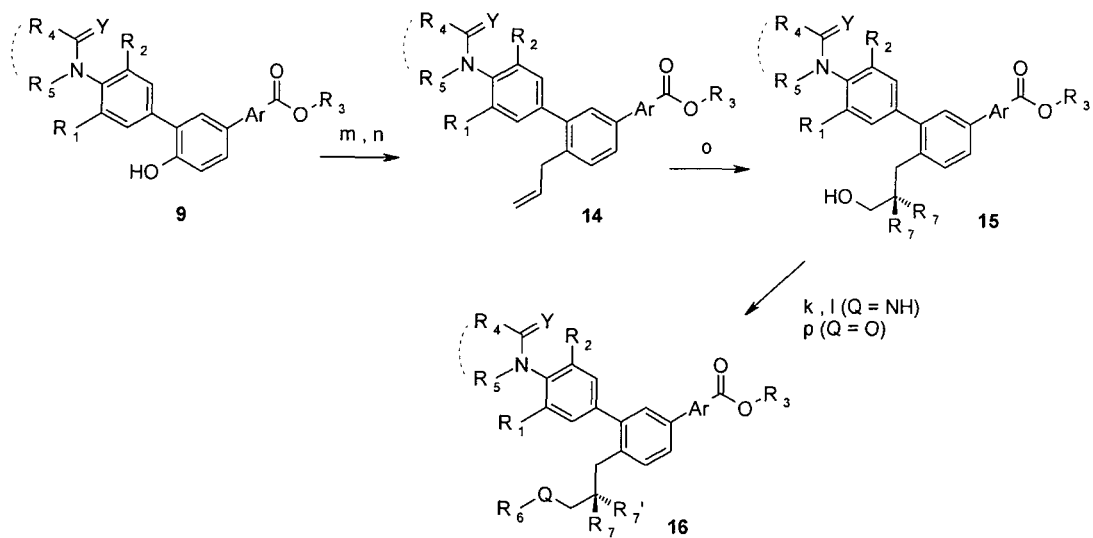

The present invention also features processes for preparing the compounds of formula (I), in particular according to the reaction schemes shown in FIGS. 1, 2 and 3.

Synthesis of Advanced Fragments (FIG. 1):

The intermediates of general formula 1 or 2 are prepared from the commercial starting material 1. Compound 1 is subjected to a first step of esterification of the carboxylic acid function (a), performed under standard esterification conditions including, for example, the methods described in "Protective Groups in Organic Synthesis" by T. W. Greene & P. G. M. Wuts, 3rd edition (J. Wiley & Sons), pages 373-377 or in "Comprehensive Organic Transformations" by R. C. Larock, $2^{nd}$ edition (J. Wiley & Sons), pages 1932-1941. The introduction of a halide (bromide or iodide) into an ortho position of the phenol function (b) may be performed under standard bromination conditions (for example by adding dibromine or an equivalent reagent such as a tetraalkylammonium tribromide) or standard iodination conditions (for example sodium iodide and sodium hypochlorite), many examples of which may be found in the literature: see, for example "Comprehensive Organic Transformations" by R. C. Larock, $2^{nd}$ edition (J. Wiley & Sons), pages 619-628.

The compounds of general formula 3 are then obtained via standard methods of etherification of phenols (c), for instance an etherification similar to a Williamson reaction starting with corresponding alkyl halides in the presence of a base, or alternatively a reaction of Mitsunobu type with the corresponding hydroxyl derivatives (see "Comprehensive Organic Transformations" by R. C. Larock, $2^{nd}$ edition (J. Wiley & Sons), pages 889-910 or, respectively: a. Dermer, O. C., Chem. Rev., 1934, 14, 409 or Nakatsugi, T. Synthesis, 1987, 280: b. Mitsunobu, O. Synthesis 1981, 1). The compounds of formula 3 are, in the case where the protecting group PG does not coincide with the desired group $R_6$, subjected to a deprotection step (d) suited to the nature of PG, the description of which will be found in "Protective Groups in Organic Synthesis" by T. W. Greene & P. G. M. Wuts, 3rd edition (J. Wiley & Sons) to obtain compound 4 ($R_6$=H) and is then subjected, where appropriate, to a standard esterification step (e) (see above) with the carboxylic acid or acyl halide derivative corresponding to the structure of $R_4$, in order to obtain the compounds of type 5 in which $R_6$ is other than H.

The intermediates of general formula 7 may be obtained from the compounds 6 after a first step of bromination (f) in the para position (see above) followed by alkylation or amidation of the aniline function (g) in the presence, respectively, of a dialkyl sulfate or of an alkyl halide and a base (see, for example, Dehmlow, E. V., Tet. Lett. 1985, 25, 97 or the reference below) or in the presence of an acyl chloride or a corresponding anhydride and a base (for example $Et_3N$) in accordance with the methods described, for example, in "Chemistry of the Amino Group" by S. Patai (Wiley-Interscience, NY 1968) pages 669-682. Alternatively, when $R_4$ and $R_5$, taken together, form a ring from among the claimed sub-structures, for example a pyrrolidine ring, the compounds 7 may be obtained after bromination of 6 and then formation of the ring (g), for example in the presence of a 1,4-dihalobutane or a 1,5-dihalopentane or the carbonyl analogues thereof, and of a base, or via a method described in "Chemistry of the Amino Group" by S. Patai (Wiley-Interscience, NY 1968) pages 669-682. Alternatively, when $R_4$ and $R_5$, taken together, form a ring from among the claimed sub-structures, the compounds of general formula 7 may also be generated after para-bromination (f, see above) and then formation (h) and reduction (i) of a pyrrolidinone, piperidinone, succinimide or piperidine-2,6-dione group (see, for example, Ohta, S. Heterocycles 1993, 36 (4), 743; Hubbard, J. L.; J. Heterocycl. Chem., 1992, 29 (4), 719; Akula, M. R.; Synth. Commun. 1998, 28 (11), 2063; Collins, C. J. Tetrahedron Lett. 1999, 40 (19), 3673).

Finally, the compounds of general formula 8 may be obtained via a sequence of two reactions: the first is an alkylation reaction (h) of a secondary aniline (when Y=H, H, see above) or of an acylaniline (when Y=O), in the presence of a dialkyl sulfate or an alkyl halide and of a base (see, for example, Bisarya, S. C. Synth. Commun. 1992, 22 (22), 3305 or the above references); an inversion of steps (h) and (g) when Y=O allows the same precursor of the compounds of general formula 8 to be obtained. The second reaction is the generation of a boronic acid or boronate function from the bromide group (i), for example by generating an organolithium or organomagnesium reagent trapped with a trialkyl borate (see, for example, Cladingboel, D. E. Org. Process Res. Dev., 2000, 4 (3), 153 or Li, W. J. Org. Chem., 2002, 67 (15), 5394) or alternatively by performing a coupling reaction with bis-dialkoxydiborane or dialkoxyborane in the presence of a catalyst of transition metal type (see, for example, Ishiyama, T. J. Org. Chem., 1995, 60 (23), 7508 or Murata, M., J. Org. Chem., 1997, 62 (19), 6458).

Synthesis of the Compounds in Which X=O (FIG. 2):

The synthesis of the final compounds of general formulae 11 and 12 may be performed according to two parallel routes for which only the order of the reactions changes.

A first route requires the synthesis of the intermediate 9, via a coupling reaction of Suzuki type (j) from the intermediate 2 and the boronate/boronic acid partner of formula 8, under standard Suzuki coupling conditions (see A. Suzuki et al., Synth. Commun., 1981, 11, 513 or Sharp, M. J. Tet. Lett. 1985, 26, 5997) or alternatively, where appropriate, optimized conditions (see, for example, Littke, A. F. et al., J. Am. Chem. Soc., 2000, 122 (17), 4020-4028). The compounds 9 are obtained directly when $R_3$ is other than H, or after a reaction to reveal the carboxylic acid function, for example by using conditions among those described in "Comprehensive Organic Transformations" by R. C. Larock, $2^{nd}$ edition (J. Wiley & Sons), pages 1959-1968.

The intermediate 9 may also be subjected to the conditions (c) described above in order to obtain the compounds of general formula 10.

These compounds of general formula 10 may also be generated via the same methods (j) described above starting with the intermediates of general formula 3.

When PG is other than the desired group $R_6$, 10 may be subjected to deprotection conditions (d) mentioned above to obtain the final compounds 11 in which $R_6$=H, and then, where appropriate, subjected to the conditions (e) to obtain the compounds 12 in which $R_6$ is other than H.

Alternatively, these same final compounds 11 and 12 may be obtained by subjecting, respectively, the intermediates 4 and 5 to the coupling conditions (j) described above.

Finally, when $R_3$=H, the advanced intermediates 11 and 12 may be subjected to reactions to reveal the carboxylic acid function, for example using conditions among those described in "Comprehensive Organic Transformations" by R. C. Larock, $2^{nd}$ edition (J. Wiley & Sons), pages 1959-1968.

The compounds of general formula 13 may be obtained after a sequence of conversion of the primary alcohol function of 11 into an amine, for example via oxidation (k) followed by reductive amination (l) (see, for example, "Comprehensive Organic Transformations" by R. C. Larock, $2^{nd}$ edition (J. Wiley & Sons)) or alternatively conversion of the alcohol into a halide and substitution of the halogen atom with an amine.

Synthesis of the Claimed Compounds in Which X is a Single Bond (FIG. 3):

When X is a single bond, the intermediates of general formula 9 are first converted into suitable sulfonyl esters under standard conditions, for example into triflates (see, for example, Robl, J. A. Tetrahedron Lett. 1990, 31 (24), 3421) (m), and this group is then subjected to an allylation reaction (n), for example in the presence of tributylallyltin and of a transition metal catalyst, for example tetrakis(triphenylphosphine)palladium (for an example, see Martorell, G.; Garcia-Raso, A.; Saa, J. M.; Tetrahedron Lett. 1990, 31 (16), 2357), to obtain the intermediates of type 14.

The final compounds of general formula 15 may then be obtained via an oxidation reaction (o) of the olefin function, for instance an oxidative hydroboration reaction (see, for example, Luo, F. T.; Negishi, E.; *J. Org. Chem.*, 1983, 48, 5144 or "Comprehensive Organic Transformations" by R. C. Larock, $2^{nd}$ edition (J. Wiley & Sons), pages 992-993 & 1005-1007) in the case where $R_7$, $R_{7'}$=H, H or alternatively via a racemic or enantioselective dihydroxylation reaction, as described, for example, in Van Rheenan, V.; Cha, D. Y.; Hartley, W. M.; *Org. Synth.*, 1978, 58, 44 or in "Comprehensive Organic Transformations" by R. C. Larock, $2^{nd}$ edition (J. Wiley & Sons), pages 996-1001.

When Q=NH, the reaction sequence (k, l) described above for the conversion of the compounds 11 into compounds 13 may be applied, in order to obtain the compounds of general formula 16. Alternatively, when Q=O and $R_6$ is other than H, a simple standard alkylation or acylation reaction of the primary alcohol function of the intermediates of structure 15 allows the final compounds of general formula 16 to be obtained.

The compounds according to the invention have modulatory properties on retinoic acid receptors (RAR). This activity on the RARα, β and γ receptors is measured in a transactivation test and quantified by means of the dissociation constant Kdapp (apparent), as described in Example 55.

The preferred compounds of the present invention have a dissociation constant of less than or equal to 5000 nM, advantageously less than or equal to 1000 nM and preferentially less than or equal to 1 nM.

Preferably, the compounds are at least modulators of receptors of RARγ type, selectively relative to the subtypes α and β, i.e., they have a ratio from the Kdapp for the RARα or RARβ receptors, and the Kdapp for the RARγ receptors, of greater than or equal to 5. Preferably, this ratio RARγ/RARβ or RARγ/RARα is greater than or equal to 10, advantageously greater than or equal to 50 and more advantageously greater than or equal to 100.

The present invention also features administration of the compounds of formula (I) as described above, as medicaments.

The compounds according to the invention are particularly suitable in the following fields of treatment:

1) for treating dermatological complaints, conditions or afflictions, associated with a keratinization disorder relating to cell differentiation and proliferation, especially for treating common acne, comedones, polymorphonuclear leukocytes, acne rosacea, nodulocystic acne, acne conglobata, senile acne, and secondary acnes such as solar acne, medication-related acne or occupational acne;

2) for treating other types of keratinization disorders, conditions or afflictions, especially ichthyosis, ichthyosiform conditions, Darier's disease, palmoplantar keratoderma, leukoplakia and leukoplakiform conditions, and cutaneous or mucous (buccal) lichen;

3) for treating other dermatological complaints, conditions or afflictions having an inflammatory immunoallergic component, with or without cell proliferation disorder, and especially all forms of psoriasis, whether cutaneous, mucous or ungual psoriasis, and even psoriatic rheumatism, or cutaneous atopy, such as eczema, or respiratory atopy, or even gingival hypertrophy;

4) in the treatment of skin disorders caused by exposure to UV radiation, and also for repairing or combating aging of the skin, whether photoinduced or chronological aging, or for reducing actinic pigmentations and keratosis, or any pathology associated with chronological or actinic aging, such as xerosis;

5) for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basocellular and spinocellular epithelioma, and also any precancerous skin lesion such as keratoacanthomas;

6) for treating other dermatological disorders such as immune dermatoses, such as lupus erythematosus, immune bullous diseases and collagen diseases, such as scleroderma;

7) in the treatment of dermatological or general complaints conditions or afflictions having an immunological component;

8) for treating certain ophthalmological disorders, especially corneopathies;

9) for preventing or curing the stigmata of epidermal and/or dermal atrophy induced by local or systemic corticosteroids, or any other form of cutaneous atrophy;

10) in the treatment of any cutaneous or general complaint, condition or affliction of viral origin;

11) for combating sebaceous function disorders, such as the hyperseborrhoea of acne or simple seborrhoea;

12) for preventing or treating cicatrization disorders, or for preventing or repairing stretch marks, or alternatively for promoting cicatrization;

13) in the treatment of pigmentation disorders, such as hyperpigmentation, melasma, hypopigmentation or vitiligo;

14) in the treatment of lipid metabolism complaints, conditions or afflictions, such as obesity, hyperlipidaemia, or non-insulin-dependent diabetes;

15) in the treatment of inflammatory complaints, conditions or afflictions, such as arthritis;

16) in the treatment or prevention of cancerous or precancerous conditions;

17) in the prevention or treatment of alopecia of various origins, especially alopecia caused by chemotherapy or radiation;

18) in the treatment of disorders of the immune system, such as asthma, type I sugar diabetes, multiple sclerosis or other selective dysfunctions of the immune system; and 19) in the treatment of complaints, conditions or afflictions of the cardiovascular system, such as arteriosclerosis or hypertension.

The present invention also features pharmaceutical compositions comprising, formulated into a physiologically acceptable medium, at least one compound of formula (I) as defined above.

This invention also features novel medicinal compositions especially useful for treating the abovementioned complaints, conditions or afflictions, comprising, in a pharmaceutically acceptable support that is compatible with the mode of administration selected for such compositions, at least one compound of formula (I), an optical isomer thereof or a salt thereof.

The compositions according to the invention may be administered, whether regime or regimen, orally, enterally, parenterally, topically or ocularly. The pharmaceutical composition is preferably packaged in a form that is suitable for topical application.

Via the oral route, the composition may be in the form of tablets, gel capsules, dragees, syrups, suspensions, solutions, powders, granules, emulsions, suspensions of microspheres or nanospheres or lipid or polymer vesicles allowing a controlled release. Via the parenteral route, the composition may be in the form of solutions or suspensions for infusion or for injection.

The compounds according to the invention are generally administered at a daily dose of about 0.01 mg/kg to 100 mg/kg of body weight, in one or more dosage intakes.

The compounds are administered systemically, at a concentration generally of from 0.001% to 10% by weight and preferably from 0.01% to 1% by weight, relative to the weight of the composition.

Via the topical route, the pharmaceutical composition according to the invention is more particularly useful for treating the skin and mucous membranes and may be in liquid, pasty or solid form, and more particularly in the form of ointments, creams, milks, pomades, powders, impregnated pads, syndets, solutions, gels, sprays, mousses, suspensions, sticks, shampoos or washing bases. It may also be in the form of suspensions of microspheres or nanospheres or of lipid or polymer vesicles or gelled or polymer patches allowing a controlled release.

The compounds are administered topically at a concentration generally of from 0.001% to 10% by weight and preferably from 0.01% to 1% by weight, relative to the total weight of the composition.

The compounds of formula (I) according to the invention also find applications in cosmetics, in particular in body and hair hygiene and especially for treating acne-prone skin, for promoting regrowth of the hair or for limiting hair loss, for combating the greasy appearance of the skin or the hair, in protection against the harmful aspects of sunlight or in the treatment of physiologically dry skin, and for preventing and/or combating photoinduced or chronological aging.

The present invention thus also features cosmetic compositions comprising, formulated into a physiologically acceptable support, at least one of the compounds of formula (I).

This invention also features the non-therapeutic use of a cosmetic composition comprising at least one compound of formula (I) for preventing and/or treating the signs of aging and/or dry skin.

This invention also features the non-therapeutic use of a cosmetic composition comprising at least one compound of formula (I) for body or hair hygiene.

The cosmetic compositions according to the invention containing, in a physiologically acceptable medium, at least one compound of formula (I) or an optical or geometrical isomer thereof or a salt thereof, may be especially in the form of a cream, a milk, a gel, suspensions of microspheres or nanospheres or lipid or polymer vesicles, impregnated pads, solutions, sprays, mousses, sticks, soaps, washing bases or shampoos.

The concentration of compound of formula (I) in the cosmetic compositions is preferably from 0.001% to 3% by weight, relative to the total weight of the composition.

The term "physiologically acceptable medium" means a medium that is compatible with the skin and optionally with its integuments (eyelashes, nails or hair) and/or mucous membranes.

The pharmaceutical and cosmetic compositions as described above may also contain inert additives, or even pharmacodynamically active additives as regards the pharmaceutical compositions, or combinations of these additives, and especially:

wetting agents;

flavor enhancers;

preservatives such as para-hydroxybenzoic acid esters;

stabilizers;

moisture regulators;

pH regulators;

osmotic pressure modifiers;

emulsifiers;

UV-A and UV-B screening agents;

antioxidants such as α-tocopherol, butylhydroxyanisole, butylhydroxytoluene, superoxide dismutase, ubiquinol or certain metal-chelating agents;

depigmenting agents such as hydroquinone, azelaic acid, caffeic acid or kojic acid;

emollients;

moisturizers, for instance glycerol, PEG 400, thiamorpholinone and its derivatives or urea;

anti-seborrhoeic or anti-acne agents, such as S-carboxymethylcysteine, S-benzylcysteamine, salts thereof or derivatives thereof, or benzoyl peroxide;

antibiotics, for instance erythromycin and its esters, neomycin, clindamycin and its esters, and tetracyclines;

anti-fungal agents such as ketoconazole or poly-4,5-methylene-3-isothiazolidones;

agents for promoting regrowth of the hair, for instance Minoxidil (2,4-diamino-6-piperidinopyrimidine 3-oxide) and its derivatives, Diazoxide (7-chloro-3-methyl-1,2,4-benzothiadiazine 1,1-dioxide) and Phenyloin (5,4-diphenylimidazolidine-2,4-dione);

non-steroidal anti-inflammatory agents;

carotenoids and especially β-carotene;

anti-psoriatic agents such as anthralin and its derivatives;

eicosa-5,8,11,14-tetraynoic acid and eicosa-5,8,11-triynoic acid, and esters and amides thereof;

retinoids, i.e., natural or synthetic RXR receptor ligands;

corticosteroids or oestrogens;

α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and its salts, amides or esters;

ion-channel blockers such as potassium-channel blockers;

or alternatively, more particularly for pharmaceutical compositions, in combination with medicaments known to interfere with the immune system (for example cyclosporin, FK 506, glucocorticoids, monoclonal antibodies, cytokines or growth factors, etc.).

Needless to say, one skilled in this art will take care to select the optional compound(s) to be added to these compositions such that the advantageous properties intrinsically associated with the present invention are not, or are not substantially, adversely affected by the envisaged addition.

The present invention also features a cosmetic regime or regimen for enhancing the appearance of the skin, wherein in that a composition comprising at least one compound of formula (I) as defined above is applied to the skin.

Activation of the retinoic acid receptors with the compounds of formula (I) according to the invention makes it possible to obtain skin of enhanced surface appearance.

In order to further illustrate the present invention and the advantages thereof, the following examples of specific active compounds are given, as are the results of the biological activities of such compounds and specific formulations thereof, it being understood that same are intended only as illustrative and in nowise limitative. In said examples to follow, all parts and percentages are given by weight, unless otherwise indicated.

EXAMPLES

Example 1

Synthesis of ethyl 3"-tert-butyl-4"-diethylamino-4'-hydroxy[1,1';3',1"]terphenyl-4-carboxylate

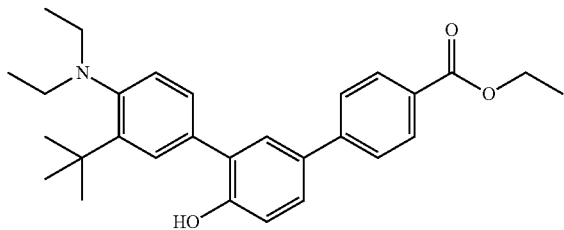 [SMILES: CCOC(=O)c1ccc(-c2ccc(O)c(-c3ccc(N(CC)CC)c(C(C)(C)C)c3)c2)cc1]

a) Preparation of 4-bromo-2-tert-butylaniline 25 g of 2 tert-butylaniline (168 mmol) are dissolved in 250 mL of THF; the reaction mixture is stirred and cooled to 0° C., and 81 g of tetrabutylammonium bromide (TBA.Br$_3$) (168 mmol) are then added portionwise while maintaining the temperature from 0° C. and 5° C. The temperature is then allowed to rise to about room temperature and the mixture is stirred for 10 minutes.

The reaction is stopped by adding 250 mL of water and is then extracted with 250 mL of ethyl acetate. The organic phases are washed with 1 L of saturated Na$_2$S$_2$O$_5$ solution and then dried over magnesium sulfate. The solvents are evaporated off and the residue is filtered through a pad of silica (pure heptane, then a 3/7 heptane/ethyl acetate mixture).

43.6 g of 4-bromo-2-tert-butylaniline (yield=100%) are obtained in the form of a white solid.

b) Preparation of (4-bromo-2-tert-butylphenyl)diethylamine 6.9 g (0.17 mol) of sodium hydride are suspended in 200 mL of tetrahydrofuran. 13 g (57 mmol) of 4-bromo-2-tert-butylaniline are added, along with 200 mL of dimethyl sulfoxide, added slowly. The mixture turns blue and, after 30 minutes, 13 mL (0.17 mol) of ethyl iodide are added and the reaction medium, which has turned white, is stirred at room temperature for 13 hours. The reaction medium is then poured into saturated ammonium chloride solution and extracted with ethyl acetate, and the organic phase is then washed twice with water. It is dried and then concentrated to dryness. The residue is purified by chromatography on silica gel (eluent: 90/10 heptane/ethyl acetate). 14.8 g of (4-bromo-2-tert-butylphenyl)diethylamine are obtained (yield=91%) in the form of a yellow oil.

c) Preparation of 3-tert-butyl-4-diethylaminophenylboronic acid 9.8 g (35 mmol) of (4-bromo-2-tert-butylphenyl)diethylamine are dissolved in 118 mL of THF at room temperature, and the reaction mixture is then cooled to −78° C. 17.5 mL of a 2 M solution of n-BuLi (35 mmol) are added dropwise and the reaction medium is left stirring at −78° C. for 1 hour. 12 mL of triisopropyl borate (B(OiPr)$_3$) (52 mmol) are added slowly and the reaction medium is stirred for 15 minutes at −70° C.

The temperature is raised to room temperature and the reaction medium is stirred for 3 hours. The reaction medium is cooled again to −70° C. and 69 mL of 1M hydrochloric acid solution (69 mmol) are added. The temperature is raised to 0° C. and the reaction medium is stirred for 30 minutes. The reaction is extracted after addition of 250 mL of water and 250 mL of ethyl acetate. The organic phases are washed with 800 mL of water and then dried over sodium sulfate. 6.5 g of 3-tert-butyl-4-diethylaminophenylboronic acid are obtained (yield=76%) in the form of a thick oil.

d) Synthesis of ethyl 3"-tert-butyl-4"-diethylamino-4'-hydroxyl[1,1';3',1"]terphenyl-4-carboxylate To 5.6 g of ethyl 3'-bromo-4'-hydroxy-biphenyl-4-carboxylate (17 mmol) are added 6.5 g of 3-tert-butyl-4-diethylaminophenylboronic acid (26 mmol) dissolved in 112 mL of toluene and 30.5 mL of 2M potassium carbonate (61 mmol). The reaction medium is stirred and heated to 40° C.; 2 g of tetrakis(triphenylphosphine)palladium (Pd(PPh$_3$)$_4$) (1.74 mmol) are added and the medium is heated to 110° C. and stirred for 3 hours. The reaction is stopped by adding 200 mL of water and the medium is then extracted with 200 mL of ethyl acetate. The organic phases are washed with 400 mL of water and neutralized with 200 mL of saturated NH$_4$Cl and then dried over magnesium sulfate. The solvents are evaporated off and the residue is then purified by chromatography on silica gel (eluent: 9/1 heptane/ethyl acetate). 1.2 g of ethyl 3"-tert-butyl-4"-diethylamino-4'-hydroxy[1,1';3',1"]terphenyl-4-carboxylate are obtained (yield=16%) in the form of an orange solid.

$^1$H NMR (CDCl$_3$, 400 MHz): 1.14 (t, J=7.4 Hz, 6H); 1.44 (t, J=7.6H, 3H); 1.51 (s, 9H); 2.94 (bs, 2H); 3.00 (bs, 2H); 4.42 (q, J=7.6 Hz, 2H); 5.49 (s, 1H); 7.11 (d, J=8.5 Hz, 1H); 7.33-7.41 (m, 2H); 7.53-7.57 (m, 3H); 7.68 (d, J=6.7 Hz, 2H); 8.11 (d, J=6.7 Hz, 2H).

Example 2

Synthesis of ethyl 3"-tert-butyl-4"-diethylamino-4'-(4-hydroxybutoxy)-[1,1';3',1"]terphenyl-4-carboxylate

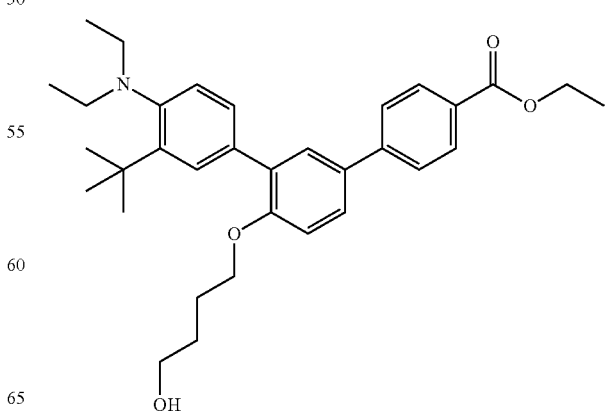

a) Preparation of ethyl 3"-tert-butyl-4'-[4-(tert-butyldimethylsilanyloxy)butoxy]-4"-diethylamino[1,1';3',1"]terphenyl-4-carboxylate 1 g of ethyl 3"-tert-butyl-4"-diethylamino-4'-hydroxy[1,1'; 3',1"]terphenyl-4-carboxylate obtained in Example 1d (2.2 mmol) are dissolved in 20 mL of dimethylformamide under a nitrogen atmosphere. 880 mg (2.7 mmol) of caesium carbonate are added. The reaction medium stirred at room temperature turns yellow. 0.64 mL of 1-bromo-4-(tert-butyldimethylsilanyloxy)butane (2.4 mmol) is then added and the reaction medium is heated at 80° C. for 18 hours. The reaction medium is then cooled to room temperature and then filtered. The solvents are evaporated off and the residue obtained is purified by chromatography on silica gel (eluent: 70/30 heptane/ethyl acetate).

1.4 g of ethyl 3"-tert-butyl-4'-[4-(tert-butyldimethylsilanyloxy)butoxy]-4"-diethylamino[1,1';3',1"]terphenyl-4-carboxylate are obtained (yield=99%) in the form of an oil.

b) Synthesis of ethyl 3"-tert-butyl-4"-diethylamino-4'-(4-hydroxybutoxy)-[1,1';3',1"]terphenyl-4-carboxylate 1.6 g of ethyl 3"-tert-butyl-4'-[4-(tert-butyldimethylsilanyloxy)butoxy]-4"-diethylamino[1,1';3',1"]terphenyl-4-carboxylate (2.5 mmol) are dissolved in 20 mL of tetrahydrofuran under a nitrogen atmosphere.

3 mL of a 1M solution of tetrabutylammonium fluoride are then added dropwise. The reaction medium is stirred at room temperature for 3 hours, and the reaction is then stopped by adding 10 mL of water and then extracted with ethyl acetate. The organic phases are combined and dried over magnesium sulfate. The solvents are evaporated off and the residue is precipitated from 10 mL of heptane and filtered. 900 mg of ethyl 3"-tert-butyl-4"-diethylamino-4'-(4-hydroxybutoxy)-[1,1';3',1"]terphenyl-4-carboxylate are obtained (yield=92%).

$^1$H NMR (CDCl$_3$-400 MHz): 1.12 (t, J=7.8 Hz, 6H); 1.43 (t, J=7.5 Hz, 3H); 1.51 (s, 9H); 1.64-1.71 (m, 2H); 1.85-2.07 (m, 2H); 2.91 (bs, 2H); 2.99 (bs, 2H); 3.62 (t, J=6.1 Hz, 2H); 4.08 (t, J=6.1 Hz, 2H); 4.41 (t, J=7.5 Hz, 2H); 7.07 (d, J=8.0 Hz, 1H); 7.30 (d, J=8.0 Hz, 1H); 7.38 (d, J=8.0 Hz, 1H); 7.56-7.59 (m, 1H); 7.62-7.64 (m, 2H); 7.68 (d, J=8.2 Hz, 2H); 8.11 (d, J=8.2 Hz, 2H).

Example 3

Synthesis of 3"-tert-butyl-4"-diethylamino-4'-(4-hydroxybutoxy)-[1,1';3',1"]terphenyl-4-carboxylic acid

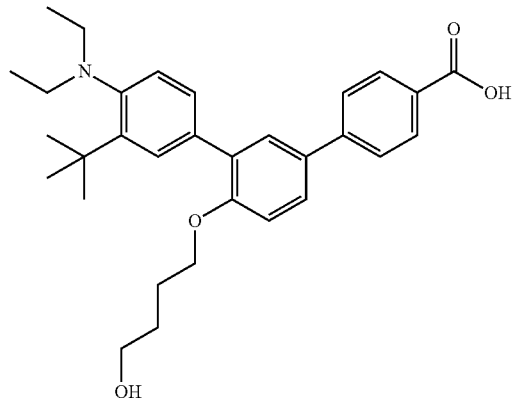 [SMILES: CCN(CC)c1ccc(-c2cc(-c3ccc(C(=O)O)cc3)ccc2OCCCCO)cc1C(C)(C)C]

a) Synthesis of 3"-tert-butyl-4"-diethylamino-4'-(4-hydroxybutoxy)-[1,1';3',1"]terphenyl-4-carboxylic acid 0.9 mL of aqueous 1N sodium hydroxide solution is added to a solution of 300 mg of ethyl 3"-tert-butyl-4"-diethylamino-4'-(4-hydroxybutoxy)-[1,1';3',1"]terphenyl-4-carboxylate (Example 2b) in a mixture of 10 mL of tetrahydrofuran and 3 mL of water. The reaction medium is stirred at room temperature for 12 hours. 0.5 mL of aqueous 1N sodium hydroxide solution is then added. After 12 hours at room temperature, the reaction medium is heated to 50° C. and then left at room temperature for 3 days. The reaction is stopped by adding 5 mL of water. The reaction medium is acidified to pH 5 by adding aqueous 1N hydrochloric acid solution and is then extracted with ethyl acetate. The organic phase is dried over magnesium sulfate. The solid obtained is taken up in heptane and then filtered. 235 mg of 3"-tert-butyl-4"-diethylamino-4'-(4-hydroxybutoxy)-[1,1';3',1"]terphenyl-4-carboxylic acid are obtained in the form of a white solid (yield=83%, m.p.=165° C.).

$^1$H NMR (DMSO-D$_6$ 400 MHz): 1.06 (t, 6H); 1.45 (s, 9H); 1.52 (m, 2H); 1.73 (m, 2H); 2.9 (m, 4H); 3.39 (t, 2H); 4.05 (t, 2H); 7.2 (dd, J=8.5 Hz, 1H); 7.3 (dd, J=8.15 Hz, 1H); 7.39 (d, J=6.93 Hz, 1H); 7.6 (s, 1H); 7.64 (s, 1H); 7.66 (d, J=8.5 Hz 2H); 7.8 (d, 2H, J=8.3 Hz); 7.97 (d, J=8.3 Hz, 1H).

Example 4

Synthesis of ethyl 4"-(acetylethylamino)-3"-tert-butyl-4'-(4-hydroxybutoxy)-[1,1';3',1"]terphenyl-4-carboxylate

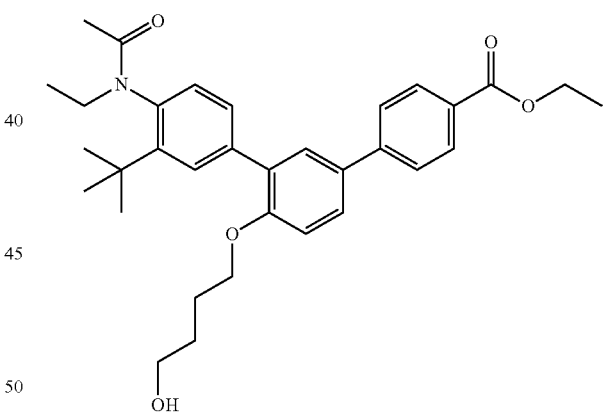

a) Preparation of (4-bromo-2-tert-butylphenyl)ethylamine

In a 1 L three-necked flask under a nitrogen atmosphere, equipped with a magnetic stirrer, 28 g (123 mmol) of 4-bromo-2-tert-butylphenylamine are dissolved in 280 mL of dimethylformamide. 5.4 g (135 mmol) of sodium hydride (60%) are added portionwise and the reaction medium is stirred for 10 minutes. 140 mL of dimethyl sulfoxide are then added slowly. The reaction medium is stirred at room temperature for 2 hours, 23 g (147 mmol, 11.8 mL) of ethyl iodide are introduced dropwise and the medium is then stirred for 18 hours at room temperature. The reaction medium is poured into 1 L of water and extracted three times with ethyl acetate.

The organic phases obtained are combined and washed with water, dried over anhydrous magnesium sulfate, filtered and evaporated to give a reddish oil. This residue is purified on silica (eluent: 95/5 heptane/ethyl acetate) to give 25 g (yield=79%) of (4-bromo-2-tert-butylphenyl)ethylamine in the form of a dark reddish oil.

b) Preparation of N-(4-bromo-2-tert-butylphenyl)-N-ethylacetamide

In a 250 mL three-necked flask under a nitrogen atmosphere, equipped with a magnetic stirrer, 15 g (58.5 mmol) of (4-bromo-2-tert-butylphenyl)ethylamine are dissolved in 150 mL of dichloromethane. 8.9 g (87.8 mmol, 12.2 mL) of triethylamine and 0.72 g (5.9 mmol) of 4-dimethylaminopyridine are added. 11.5 g (146 mmol, 2.5 mL) of acetyl chloride are added dropwise and the reaction medium is stirred for 1 hour at room temperature. The reaction medium is poured into 250 mL of water and extracted twice with dichloromethane. The organic phases obtained are combined and washed with water, dried over anhydrous magnesium sulfate, filtered and evaporated to give a blackish oil. This oil is purified by chromatography on silica (eluent: 80/20 heptane/ethyl acetate) to give 15 g (yield=86%) of N-(4-bromo-2-tert-butylphenyl)-N-ethylacetamide in the form of an orange oil.

c) Preparation of N-[2-tert-butyl-4-(4,4,5,5-tetramethyl[1,3,2]dioxaborolan-2-yl)phenyl]-N-ethylacetamide In a 250 mL three-necked flask under a nitrogen atmosphere, equipped with a magnetic stirrer, 10 g (33.5 mmol) of N-(4-bromo-2-tert-butylphenyl)-N-ethylacetamide are dissolved in 100 mL of dimethylformamide. The solution is then degassed by sparging with nitrogen for 15 minutes. 13.2 g (134 mmol) of potassium acetate, 12.8 g (50.3 mmol) of bis(pinacolato)diborane and 2.73 g (3.35 mmol) of [1,1'-bis(diphenylphosphino)ferrocene]dichloropalladium (II) are then added; the reaction medium is heated at 80° C. and stirred at this temperature for 3 hours. The reaction medium is poured into 500 mL of water and extracted twice with ethyl acetate. The organic phases obtained are combined and washed with water, dried over anhydrous magnesium sulfate, filtered and evaporated to give a blackish oil. This oil is purified by chromatography on silica (eluent: 90/10 heptane/ethyl acetate) to give 12 g (yield=100%) of N-[2-tert-butyl-4-(4,4,5,5-tetramethyl[1,3,2]dioxaborolan-2-yl)phenyl]-N-ethylacetamide in the form of a beige-colored powder.

d) Preparation of ethyl 4"-(acetylethylamino)-3"-tert-butyl-4'-hydroxy[1,4';3',1"]terphenyl-4-carboxylate In a manner similar to that of Example 1d, by reacting 2 g of ethyl 3'-bromo-4'-hydroxy-biphenyl-4-carboxylate (6 mmol) with 2.7 g of N-[2-tert-butyl-4-(4,4,5,5-tetramethyl[1,3,2]dioxaborolan-2-yl)phenyl]-N-ethylacetamide (9 mmol) in the presence of tetrakis(triphenylphosphine)palladium. 1.9 g of ethyl 4"-(acetylethylamino)-3"-tert-butyl-4'-hydroxy[1,1';3',1"]terphenyl-4-carboxylate (yield=70%) are obtained in the form of a beige-colored powder.

e) Preparation of ethyl 4"-(acetylethylamino)-3"-tert-butyl-4'-[4-(tert-butyldimethylsilanyloxy)butoxy]-[1,1';3',1"]terphenyl-4-carboxylate In a manner similar to that of Example 2a, by reacting 260 mg of ethyl 4"-(acetylethylamino)-3"-tert-butyl-4'-hydroxy [1,1';3',1"]terphenyl-4-carboxylate (0.56 mmol) in 12 mL of dimethylformamide with 225 mg of caesium carbonate and 0.16 mL of 1-bromo-4-(tert-butyldimethylsilanyloxy)butane, 310 mg of ethyl 4"-(acetylethylamino)-3"-tert-butyl-4'-[4-(tert-butyldimethylsilanyloxy)butoxy]-[1,1';3',1"]terphenyl-4-carboxylate (yield=99%) are obtained in the form of an oil.

f) Synthesis of ethyl 4"-(acetylethylamino)-3"-tert-butyl-4'-(4-hydroxybutoxy)-[1,1';3',1"]terphenyl-4-carboxylate In a manner similar to that of Example 2b, by reacting 320 mg of ethyl 4"-(acetylethylamino)-3"-tert-butyl-4'-[4-(tert-butyldimethylsilanyloxy)butoxy]-[1,1';3',1"]terphenyl-4-carboxylate in 10 mL of tetrahydrofuran with 0.5 mL of 1M tetrabutylammonium fluoride, 270 mg of ethyl 4"-(acetylethylamino)-3"-tert-butyl-4'-(4-hydroxybutoxy)-[1,1';3',1"]terphenyl-4-carboxylate are obtained (yield=99%).

$^1$H NMR (CDCl$_3$-400 MHz): 1.27 (t, 3H); 1.42 (s, 9H); 1.43 (t, 3H); 1.63-1.69 (m, 2H); 1.89 (s, 3H); 1.87-1.91 (m, 2H); 2.85-2.91 (m, 2H); 3.60-3.64 (m, 2H); 4.11 (t, J=6.1 Hz, 2H); 4.42 (t, J=7.5 Hz, 2H); 7.06 (d, J=8.0 Hz, 1H); 7.10 (d, J=8.0 Hz, 1H); 7.42 (d, J=8.0 Hz, 1H); 7.61-7.63 (m, 2H); 7.68 (d, J=8.2 Hz, 2H); 7.81 (s, 1H); 8.12 (d, J=8.2 Hz, 2H).

Example 5

Synthesis of 4"-(acetylethylamino)-3"-tert-butyl-4'-(4-hydroxybutoxy)-[1,1';3',1"]terphenyl-4-carboxylic acid

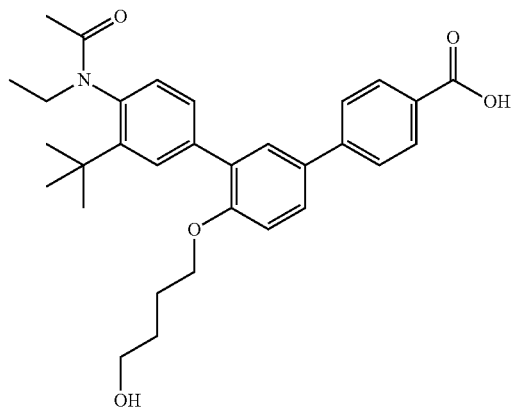 [SMILES: CCN(C(C)=O)c1ccc(-c2cc(-c3ccc(C(=O)O)cc3)ccc2OCCCCO)cc1C(C)(C)C]

a) Synthesis of 4"-(acetylethylamino)-3"-tert-butyl-4'-(4-hydroxybutoxy)-[1,1';3',1"]terphenyl-4-carboxylic acid In a manner similar to that of Example 3, by reacting 270 mg of ethyl 4"-(acetylethylamino)-3"-tert-butyl-4'-(4-hydroxybutoxy)-[1,1';3',1"]terphenyl-4-carboxylate with 0.8 mL and then 0.4 mL of aqueous 1N sodium hydroxide solution in a mixture of 8 mL of tetrahydrofuran and 2 mL of water. 195 mg of 4"-(acetylethylamino)-3"-tert-butyl-4'-(4-hydroxybutoxy)-[1,1';3',1"]terphenyl-4-carboxylic acid are obtained in the form of a white solid (yield=95%, m.p.=75° C.).

$^1$H NMR (DMSO, 400 MHz): 1.26 (m, 3H); 1.43 (s, 9H); 1.67 (m, 2H); 1.87 (s, 3H); 1.89 (m, 2H); 2.92 (m, 1H); 3.63

(m, 2H); 4.11 (m, 2H); 4.4 (m, 1H); 7.0 (m, 1H); 7.36 (m, 1H); 7.58 (m, 4H); 7.77 (m, 1H); 8.12 (m, 2H).

Example 6

Synthesis of 3''-tert-butyl-4''-diethylamino-4'-(2-hydroxyethoxy)-[1,1';3',1'']terphenyl-4-carboxylic acid

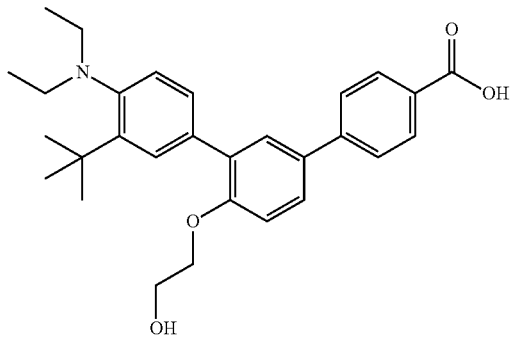 [SMILES: CCN(CC)c1ccc(-c2cc(-c3ccc(C(=O)O)cc3)ccc2OCCO)cc1C(C)(C)C]

a) Preparation of ethyl 4'-(2-acetoxyethoxy)-3''-tert-butyl-4''-diethylamino[1,1';3',1'']terphenyl-4-carboxylate 850 mg (1.9 mmol) of ethyl 3''-tert-butyl-4''-diethylamino-4'-hydroxy[1,1';3',1'']terphenyl-4-carboxylate (obtained in Example 1d) are dissolved in dimethylformamide under nitrogen. 92 mg (2.3 mmol) of 60% sodium hydride are added. After 20 minutes at room temperature, 0.25 mL (2.3 mmol) of 2-bromoethan-1-ol acetate are added and the mixture is stirred for 24 hours at room temperature and then poured into saturated ammonium chloride solution and extracted with ethyl acetate. The organic phase is washed with water and then dried and evaporated. The residue obtained is purified by chromatography on silica gel (eluent: 70/30 heptane/ethyl acetate). 1 g of ethyl 4'-(2-acetoxyethoxy)-3''-tert-butyl-4''-diethylamino[1,1';3',1'']terphenyl-4-carboxylate is obtained (yield=99%) in the form of a colorless oil.

b) Synthesis of 3''-tert-butyl-4''-diethylamino-4'-(2-hydroxyethoxy)-[1,1';3,1'']terphenyl-4-carboxylic acid 1 g (1.9 mmol) of ethyl 4'-(2-acetoxyethoxy)-3''-tert-butyl-4''-diethylamino[1,1';3',1'']terphenyl-4-carboxylate is placed in 50 mL of tetrahydrofuran and 19 mL (19 mmol) of 1N sodium hydroxide solution are added. The mixture is stirred at reflux for 12 hours. The yellow solution obtained is poured into saturated ammonium chloride solution, the pH is adjusted to 5-6 with 1N hydrochloric acid solution and the mixture is then extracted with ethyl acetate. The organic phase is dried over magnesium sulfate and then concentrated to dryness. 455 mg of 3''-tert-butyl-4''-diethylamino-4'-(2-hydroxyethoxy)-[1,1';3',1'']terphenyl-4-carboxylic acid are obtained in the form of a white solid (yield=52%, m.p.=216° C.)

$^1$H NMR (DMSO, 400 MHz): 1.06 (t, J=7.2 Hz, 6H); 1.47 (s, 9H); 2.84 (m, 2H); 2.94 (m, 2H); 4.11 (m, 2H); 7.23 (d, J=8 Hz, 1H); 7.32 (d, J=8 Hz, 1H); 7.48 (dd, J=1.6 Hz, 8.4 Hz, 1H); 7.66 (dd, J=1.2 Hz, 4 Hz, 2H); 7.69 (d, J=2 Hz, 1H); 7.99 (d, J=8 Hz, 2H); 7.82 (d, J=8 Hz, 2H).

Example 7

Synthesis of ethyl 3''-tert-butyl-4''-diethylamino-4'-(3-hydroxypropoxy)-[1,1';3',1'']terphenyl-4-carboxylate

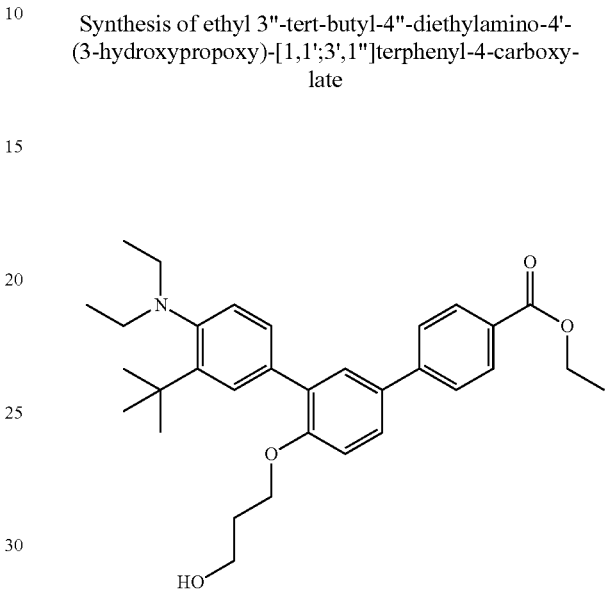

a) Preparation of ethyl 3''-tert-butyl-4'-[3-(tert-butyldimethylsilanyloxy)propoxy]-4''-diethylamino[1,1';3',1'']terphenyl-4-carboxylate In a manner similar to that of Example 2a, by reacting 1 g of ethyl 3''-tert-butyl-4''-diethylamino-4'-hydroxy[1,1';3',1'']terphenyl-4-carboxylate (obtained in Example 1d) (2.2 mmol) in 20 mL of dimethylformamide with 880 mg (2.7 mmol) of caesium carbonate and 0.6 mL of 1-bromo-3-(tert-butyldimethylsilanyloxy)propane (2.4 mmol). 1.35 g of ethyl 3''-tert-butyl-4'-[4-(tert-butyldimethylsilanyloxy)propoxy]-4''-diethylamino[1,1';3',1'']terphenyl-4-carboxylate are obtained (yield=99%) in the form of an oil.

b) Synthesis of ethyl 3''-tert-butyl-4''-diethylamino-4'-(4-hydroxypropoxy)-[1,1';3',1'']terphenyl-4-carboxylate In a manner similar to that of Example 2b, by reacting 1 g of ethyl 3''-tert-butyl-4'-[4-(tert-butyldimethylsilanyloxy)propoxy]-4''-diethylamino[1,1';3',1'']terphenyl-4-carboxylate (1.62 mmol) in 25 mL of tetrahydrofuran with 2 mL of 1M tetrabutylammonium fluoride. 790 mg of ethyl 3''-tert-butyl-4''-diethylamino-4'-(4-hydroxypropoxy)-[1,1';3',1'']terphenyl-4-carboxylate are obtained (yield=97%, m.p.=114-115° C.).

$^1$H NMR (DMSO, 400 MHz): 1.10 (t, J=7.1 Hz, 6H); 1.41 (t, J=7.1 Hz, 3H); 1.49 (s, 9H); 1.81 (m, 1H); 2.90 (bs, 2H); 3.0 (bm, 2H); 3.88 (m, 2H); 4.13 (t, J=4.4 Hz, 2H); 4.40 (q,

J=7.1 Hz, 2H); 7.08 (d, J=8.5 Hz, 1H); 7.30 (m, 1H); 7.36 (m, 1H); 7.56 (m, 1H); 7.62 (m, 2H); 7.66 (d, J=8.4 Hz, 2H); 8.09 (d, J=8.1 Hz, 2H).

Example 8

Synthesis of 3"-tert-butyl-4"-diethylamino-4'-(2-hydroxypropoxy)-[1,1';3',1"]terphenyl-4-carboxylic acid

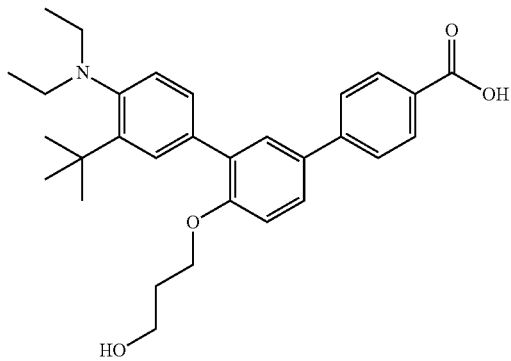 [SMILES: CCN(CC)c1ccc(-c2cc(-c3ccc(C(=O)O)cc3)ccc2OCCCO)cc1C(C)(C)C]

In a manner similar to that of Example 3, by reacting 870 mg of ethyl 3"-tert-butyl-4"-diethylamino-4'-(4-hydroxypropoxy)-[1,1';3',1"]terphenyl-4-carboxylate (Example 6b, 1.7 mmol) with 15 mL of 1N sodium hydroxide solution. 410 mg of 3"-tert-butyl-4"-diethylamino-4'-(2-hydroxypropoxy)-[1,1';3',1"]terphenyl-4-carboxylic acid are obtained in the form of a white solid (yield=51%, m.p.=193° C.).

$^1$H NMR (DMSO, 400 MHz): 1.05 (t, J=7 Hz, 6H); 1.46 (s, 9H); 1.85 (t, J=6 Hz, 2H); 2.50 (m, 2H); 2.95 (m, 2H); 3.51 (t, J=8 Hz, 2H); 4.12 (t, J=4 Hz, 2H); 4.50 (s, 1H); 7.22 (d, J=8 Hz, 1H); 7.32 (d, J=8 Hz, 1H); 7.41 (dd, J=1.6 Hz, 8 Hz, 1H); 7.61 (d, J=1.6 Hz, 1H); 7.65 (d, J=2.4 Hz, 1H); 7.70 (dd, J=2 Hz, 8 Hz, 1H); 7.83 (d, J=8.4 Hz, 2H); 7.99 (d, J=8 Hz, 2H); 13.1 (s, 1H).

Example 9

Synthesis of ethyl 4"-diethylamino-4'-(3-hydroxypropoxy)-[1,1';3',1"]terphenyl-4-carboxylate

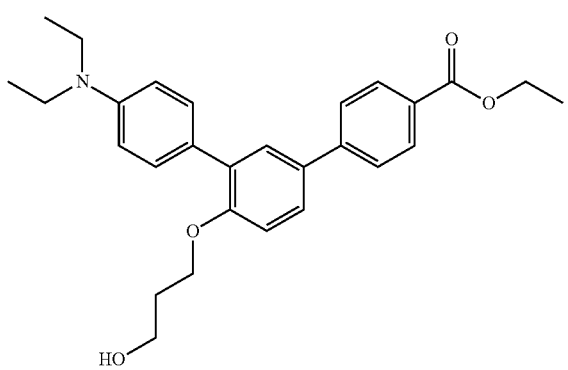 [SMILES: CCOC(=O)c1ccc(-c2ccc(OCCCO)c(-c3ccc(N(CC)CC)cc3)c2)cc1]

a) Preparation of 4-Diethylaminophenylboronic acid

In a manner similar to that of Example 1c, by reacting 5 g of (4-bromo-phenyl)diethylamine (21.9 mmol) with 13 mL of 2.0 M n-butyllithium solution and 6 mL (26 mmol) of triisopropyl borate. 4 g of 4-diethylaminophenylboronic acid (yield=94%) are obtained in the form of a white solid.

b) Preparation of ethyl 3'-bromo-4'-[3-(tert-butyldimethylsilanyloxy)propoxy]biphenyl-4-carboxylate In a manner similar to that of Example 2a, by reacting 3 g of ethyl 3'-bromo-4'-hydroxy-biphenyl-4-carboxylate (9.3 mmol) in 100 mL of dimethylformamide with 448 mg (11 mmol) of sodium hydride and 2.6 mL of 1-bromo-3-(tert-butyldimethylsilanyloxy)propane (11 mmol). 2.95 g of ethyl 3'-bromo-4'-[3-(tert-butyldimethylsilanyloxy)propoxy]biphenyl-4-carboxylate are obtained (yield=64%) in the form of an oil.

c) Preparation of ethyl 4'-[3-(tert-butyldimethylsilanyloxy)propoxy]-4"-diethylamino[1,1';3',1"]terphenyl-4-carboxylate In a manner similar to that of Example 1d, by reacting 1 g of ethyl 3'-bromo-4'-[3-(tert-butyldimethylsilanyloxy)propoxy]biphenyl-4-carboxylate (2 mmol) with 580 mg of 4-diethylaminophenylboronic acid (3 mmol) in the presence of tetrakis(triphenylphosphine)palladium. 1.15 g of ethyl 4'-[3-(tert-butyldimethylsilanyloxy)propoxy]-4"-diethylamino[1,1';3',1"]terphenyl-4-carboxylate (yield=100%) are obtained in the form of a colorless oil.

d) Synthesis of ethyl 4"-diethylamino-4'-(3-hydroxypropoxy)-[1,1';3',1"]terphenyl-4-carboxylate In a manner similar to that of Example 2b, by reacting 730 mg of ethyl 4'-[3-(tert-butyldimethylsilanyloxy)propoxy]-4"-diethylamino[1,1';3',1"]terphenyl-4-carboxylate (1.3 mmol) in 25 mL of tetrahydrofuran with 1.6 mL of 1M tetrabutylammonium fluoride. 430 mg of ethyl 4"-diethylamino-4'-(3-hydroxypropoxy)-[1,1';3',1"]terphenyl-4-carboxylate are obtained (yield=74%).

$^1$H NMR (CDCl$_3$, 400 MHz): 1.22 (t, J=7.4 Hz, 6H); 1.43 (t, J=7.6H, 3H); 2.05 (m, 2H); 3.42 (q, J=7.4 Hz, 4H); 3.81 (m, 2H); 4.17 (t, J=5.7 Hz, 2H); 4.41 (q, J=7.6 Hz, 2H); 6.76 (d, J=8.9 Hz, 1H); 7.08 (d, J=8.1 Hz, 2H); 7.45-7.47 (m, 2H); 7.52 (dd, J$_1$=2.3 Hz, J$_2$=8.6 Hz, 1H); 7.62 (d, J=2.4 Hz, 1H); 7.67 (d, J=6.7 Hz, 2H); 8.10 (d, J=6.7 Hz, 2H).

Example 10

Synthesis of 4"-diethylamino-4'-(3-hydroxypropoxy)-[1,1';3',1"]terphenyl-4-carboxylic acid

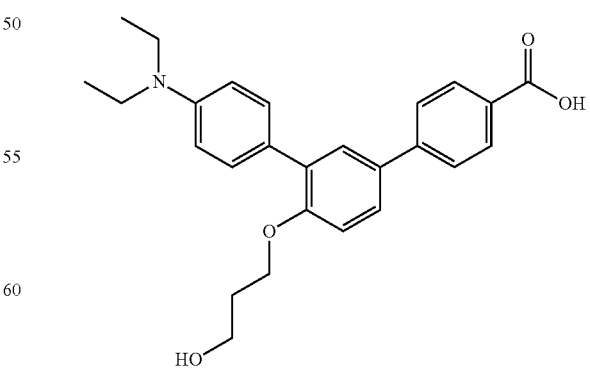

In a manner similar to that of Example 3, by reacting 430 mg of ethyl 4"-diethylamino-4'-(3-hydroxypropoxy)-[1,1';3',1"]terphenyl-4-carboxylate (Example 8d, 0.9 mmol) with 10 mL of 1N sodium hydroxide solution, 100 mg of 4"-diethylamino-4'-(3-hydroxypropoxy)-[1,1';3',1"]terphenyl-4-carboxylic acid are obtained in the form of a yellow solid (yield=25%, m.p.=200° C.).

HPLC Thermo Aquasil $C_{18}$, 3 microns, 2×150 mm, mobile phase: A ($CH_3CN$/0.1 v/v $HCO_2H$); B ($H_2O$/0.1 v/v $HCO_2H$), Flow rate: 0.5 mL/minutes. Gradient: 0 min: 90% B, 0-20 min: 90-5% B, 20-30 min: 5% B; retention time: 10.01 min, purity: 96%, MS (ESI) m/z 420.22 $(M+H)^+$ Example 11

Synthesis of ethyl 4"-diethylamino-3"-ethyl-4'-(3-hydroxypropoxy)-[1,1';3',1"]terphenyl-4-carboxylate

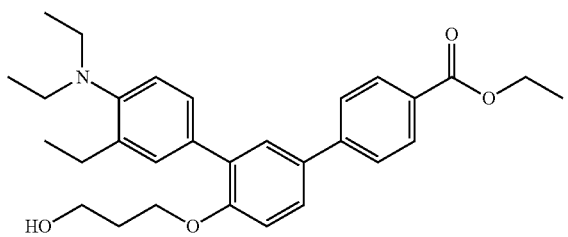 [SMILES: CCOC(=O)c1ccc(-c2ccc(OCCCO)c(-c3ccc(N(CC)CC)c(CC)c3)c2)cc1]

a) Preparation of (4-bromo-2-ethylphenyl)diethylamine

In a manner similar to that of Example 1b, by reacting 6 g (0.15 mol) of sodium hydride with 10 g (50 mmol) of 4-bromo-2-ethylaniline, 11.3 g of (4-bromo-2-ethylphenyl)diethylamine are obtained (yield=88%) in the form of a yellow oil.

b) Preparation of 4-diethylamino-3-ethylphenylboronic acid

In a manner similar to that of Example 1c, by reacting 3 g of (4-bromo-2-ethylphenyl)diethylamine (11.7 mmol) with 5.2 mL of a 2.5 M solution of n-butyllithium and 3.2 mL (14 mmol) of triisopropyl borate, 0.9 g of 4-diethylamino-3-ethylphenylboronic acid (yield=35%) is obtained in the form of a white solid.

c) Preparation of ethyl 4'-[3-(tert-butyldimethylsilanyloxy)propoxy]-4"-diethylamino-3"-ethyl[1,1';3',1"]terphenyl-4-carboxylate In a manner similar to that of Example 1d, by reacting 1.4 g (2.9 mmol) of ethyl 3'-bromo-4'-[3-(tert-butyldimethylsilanyloxy)propoxy]biphenyl-4-carboxylate (obtained in Example 5b) with 900 mg of 4-diethylamino-3-ethylphenylboronic acid (4 mmol) in the presence of tetrakis(triphenylphosphine)palladium, 674 mg of ethyl 4'-[3-(tert-butyldimethylsilanyloxy)propoxy]-4"-diethylamino-3"-ethyl[1,1';3',1"]terphenyl-4-carboxylate (yield=39%) are obtained in the form of a colorless oil.

d) Synthesis of ethyl 4"-diethylamino-3"-ethyl-4'-(3-hydroxypropoxy)-[1,1';3',1"]terphenyl-4-carboxylate In a manner similar to that of Example 2b, by reacting 660 mg of ethyl 4'-[3-(tert-butyldimethylsilanyloxy)propoxy]-4"-diethylamino-3"-ethyl[1,1';3',1"]terphenyl-4-carboxylate (1.1 mmol) in 25 mL of tetrahydrofuran with 1.2 mL of 1M tetrabutylammonium fluoride. 280 mg of ethyl 4"-diethylamino-3"-ethyl-4'-(3-hydroxypropoxy)-[1,1';3',1"]terphenyl-4-carboxylate are obtained (yield=52%).

$^1$H NMR ($CDCl_3$, 400 MHz): 1.05 (t, J=7.4 Hz, 6H); 1.28 (t, J=7.5 Hz, 3H); 1.44 (t, J=7.6 Hz, 3H); 2.02 (m, 2H); 2.80 (q, J=7.5 Hz, 2H); 3.02 (q, J=7.4 Hz, 4H); 3.77 (q, J=5.6 Hz, 2H); 4.17 (t, J=5.7 Hz, 2H); 4.42 (q, J=7.6 Hz, 2H); 7.10 (d, J=8.5 Hz, 1H); 7.18 (d, J=8.1 Hz, 1H); 7.35 (dd, $J_1$=2.1 Hz, $J_2$=8.2 Hz, 1H); 7.44 (d, J=2.1 Hz, 1H); 7.57 (dd, $J_1$=2.4 Hz, $J_2$=8.5 Hz, 1H); 7.63 (d, J=2.4 Hz, 1H); 7.57 (dd, $J_1$=2.4 Hz, $J_2$=8.5 Hz, 1H); 7.64 (d, J=2.4 Hz, 1H); 7.69 (d, J=6.7 Hz, 2H); 8.11 (d, J=6.7 Hz, 2H).

Example 12

Synthesis of 4"-diethylamino-3"-ethyl-4'-(3-hydroxypropoxy)-[1,1';3',1"]terphenyl-4-carboxylic acid

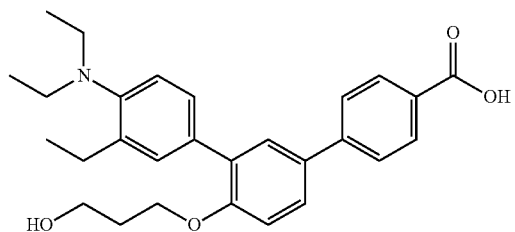 [SMILES: CCc1cc(-c2cc(-c3ccc(C(=O)O)cc3)ccc2OCCCO)ccc1N(CC)CC]

a) Synthesis of 4"-Diethylamino-3"-ethyl-4'-(3-hydroxypropoxy)-[1,1';3',1"]terphenyl-4-carboxylic acid Into a 25 mL three-necked flask under a nitrogen atmosphere, equipped with a magnetic stirrer, are placed 270 mg (0.57 mmol) of ethyl 4"-diethylamino-3"-ethyl-4'-(3-hydroxypropoxy)-[1,1';3',1"]terphenyl-4-carboxylate (Example 10d) and 22 mg (5.7 mmol) of solid sodium hydroxide in 5.4 mL of tetrahydrofuran. The reaction medium is heated at the reflux temperature of the tetrahydrofuran for 5 hours. The reaction medium is concentrated under vacuum. The crude reaction product obtained is taken up in water and the pH of the medium thus obtained is adjusted to pH=4 by addition of hydrochloric acid solution in a proportion of 1 mol/L. The precipitate obtained, after stirring for 30 minutes, is purified by chromatography on silica (eluent: 40/60 heptane/ethyl acetate) to give, after evaporation of the fractions, 80 mg (yield=31%) of 4"-diethylamino-3"-ethyl-4'-(3-hydroxypropoxy)-[1,1';3',1"]terphenyl-4-carboxylic acid in the form of a cream-colored powder (m.p.=204° C.).

$^1$H NMR (DMSO, 400 MHz): 1.02 (t, J=7.2 Hz, 6H); 1.25 (t, J=7.2 Hz, 3H); 2.02 (m, 2H); 2.78 (q, J=7.6 Hz, 2H); 3.01 (q, J=6.8 Hz, 4H); 3.76 (t, J=5.6 Hz, 2H); 4.18 (t, J=5.6 Hz, 2H); 7.08 (d, J=8.4 Hz, 1H); 7.16 (d, J=8.0 Hz, 1H); 7.33 (dd, $J_1$=2.0 Hz, $J_2$=8.4 Hz, 1H); 7.42 (d, J=1.6 Hz, 1H); 7.56 (dd, $J_1$=2.0 Hz, $J_2$=8.4 Hz, 1H); 7.63 (d, J=2.4 Hz, 1H); 7.70 (d, J=8.4 Hz, 2H); 8.14 (d, J=8.4 Hz, 2H).

Example 13

Synthesis of 4"-diethylamino-3"-ethyl-4'-(2-hydroxyethoxy)-[1,1';3',1"]terphenyl-4-carboxylic acid

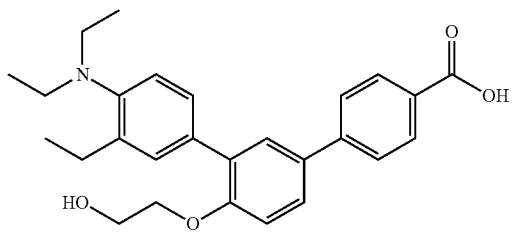 [SMILES: CCc1cc(-c2cc(-c3ccc(C(=O)O)cc3)ccc2OCCO)ccc1N(CC)CC]

a) Preparation of ethyl 4'-(2-acetoxyethoxy)-3'-bromobiphenyl-4-carboxylate

In a manner similar to that of Example 6a, by reacting 2 g (6 mmol) of ethyl 3'-bromo-4'-hydroxybiphenyl-4-carboxylate with 320 mg (8 mmol) of 60% sodium hydride and 0.7 mL (7 mmol) 2-bromoethan-1-ol acetate, 2.2 g of ethyl 4'-(2-acetoxyethoxy)-3'-bromobiphenyl-4-carboxylate are obtained (yield=95%) in the form of a colorless oil.

b) Preparation of ethyl 2'-(2-acetoxyethoxy)-3-tert-butyl-4-diethylamino[1,1';4',1"]terphenyl-3"-carboxylate In a manner similar to that of Example 1d, by reacting 400 mg of ethyl 4'-(2-acetoxyethoxy)-3'-bromobiphenyl-4-carboxylate (1 mmol) with 340 mg of 4-diethylamino-3-ethylphenylboronic acid (1.5 mmol) in the presence of tetrakis(triphenylphosphine)palladium, 500 mg of ethyl 2'-(2-acetoxymethoxy)-3-tert-butyl-4-diethylamino[1,1';4',1"]terphenyl-3"-carboxylate (yield=97%) are obtained in the form of a white solid.

c) Synthesis of 4"-diethylamino-3"-ethyl-4'-(2-hydroxyethoxy)-[1,1';3',1"]terphenyl-4-carboxylic acid In a manner similar to that of Example 6b, by reacting 690 mg (1.4 mmol) of ethyl 2'-(2-acetoxyethoxy)-3-tert-butyl-4-diethylamino[1,1';4',1"]terphenyl-3"-carboxylate with 550 mg (14 mmol) of sodium hydroxide, 470 mg of 4"-diethylamino-3"-ethyl-4'-(2-hydroxyethoxy)-[1,1';3',1"]terphenyl-4-carboxylic acid are obtained (yield=79%) in the form of a white solid (m.p.=206° C.).

$^1$H NMR (DMSO, 400 MHz): 1.05 (t, J=7.0 Hz, 6H); 1.27 (t, J=7.6 Hz, 3H); 2.80 (q, J=7.2 Hz, 2H); 3.03 (q, J=7.2 Hz, 4H); 3.90 (m, 2H); 4.15 (m, 2H); 7.09 (m, 1H); 7.18 (m, 1H); 7.38 (m, 1H); 7.47 (m, 1H); 7.56 (m, 1H); 7.7 (m, 3H); 8.18 (d, J=8.4 Hz, 2H).

Example 14

Synthesis of ethyl 4"-diethylamino-3"-ethyl-4'-(2-hydroxyethoxy)-[1,1';3',1"]terphenyl-4-carboxylate

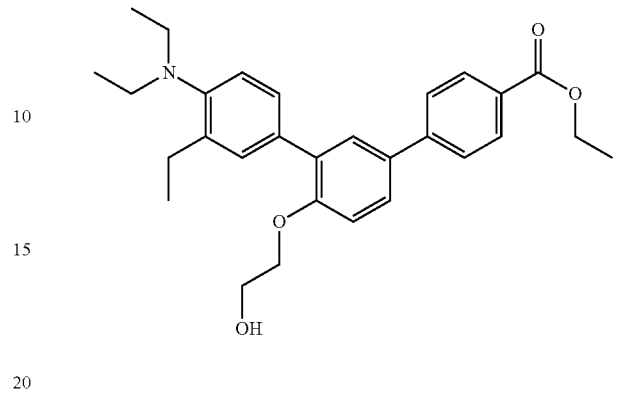

a) Synthesis of ethyl 4"-diethylamino-3"-ethyl-4'-(2-hydroxyethoxy)-[1,1';3',1"]terphenyl-4-carboxylate 6.6 g of ethyl 2'-(2-acetoxyethoxy)-3-tert-butyl-4-diethylamino[1,1';4',1"]terphenyl-3"-carboxylate (obtained in Example 13b) are dissolved in 200 mL of a 2% solution of potassium carbonate in ethanol. The reaction medium is stirred for 2 hours at room temperature and then poured into saturated ammonium chloride solution and extracted with ethyl acetate. The residue obtained is purified by chromatography on silica gel (eluent: 7/3 heptane/ethyl acetate). 4 g of ethyl 4"-diethylamino-3"-ethyl-4'-(2-hydroxyethoxy)-[1,1';3',1"]terphenyl-4-carboxylate (yield=66%) are obtained in the form of a white solid (m.p.=97° C.).

$^1$H NMR (DMSO, 400 MHz): 1.06 (t, J=7.0 Hz, 6H); 1.28 (t, J=7.5 Hz, 3H); 1.44 (t, J=7.1 Hz, 3H); 1.91 (bs, 1H); 2.80 (q, J=7.5 Hz, 2H); 3.04 (q, J=7.0 Hz, 4H); 3.90 (bs, 2H); 4.16 (m, 2H); 4.42 (q, J=7.1 Hz, 2H); 7.10 (d, J=8.5 Hz, 1H); 7.18 (d, J=8.5 Hz, 1H); 7.37 (dd, J=2.1 hz, 8.2 Hz, 1H); 7.47 (d, J=2.0 Hz, 1H); 7.57 (dd, J=2.4 Hz, 8.5 Hz, 1H); 7.66 (m, 1H); 7.69 (d, J=8.4 Hz, 2H); 8.12 (d, J=8.4 Hz, 2H).

Example 15

Synthesis of ethyl 3"-tert-butyl-4"-diethylamino-4'-(2-hydroxyethoxy)-[1,1';3',1"]terphenyl-4-carboxylate

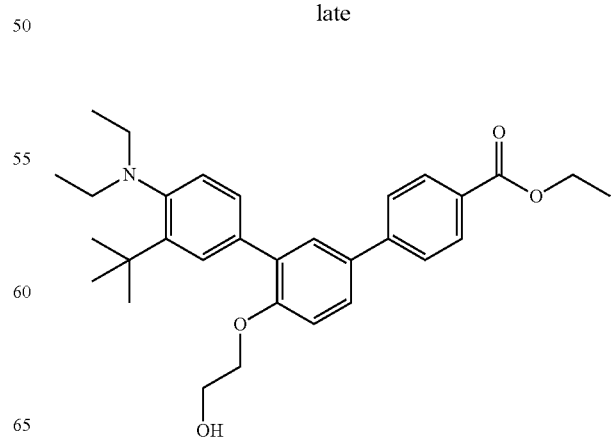

a) Synthesis of Ethyl 3"-tert-butyl-4"-diethylamino-4'-(2-hydroxyethoxy)-[1,1';3',1"]terphenyl-4-carboxylate In a manner similar to that of Example 14a, by reacting 490 mg of ethyl 4'-(2-acetoxymethoxy)-3"-tert-butyl-4"-diethylamino[1,1';3',1"]terphenyl-4-carboxylate (0.9 mmol) obtained in Example 6a with 10 mL of a 2% solution of potassium carbonate in ethanol, 400 mg of ethyl 3"-tert-butyl-4"-diethylamino-4'-(2-hydroxyethoxy)-[1,1';3',1"]terphenyl-4-carboxylate are obtained (yield=82%) in the form of a white solid (m.p.=127° C.).

$^1$H NMR (DMSO, 400 MHz): 1.10 (t, J=7.0 Hz, 6H); 1.41 (t, J=7.1 Hz, 3H); 1.49 (s, 9H); 1.81 (bs, 1H); 2.90 (bs, 2H); 3.0 (bs, 2H); 3.87 (m, 2H); 4.13 (m, 2H); 4.40 (q, J=7.1 Hz, 2H); 7.08 (d, J=8.5 Hz, 1H); 7.30 (d, J=8.5 Hz, 1H); 7.35 (dd, J=2.1 hz, 8.2 Hz, 1H); 7.56 (dd, J=2.0 Hz, 8.1 Hz, 1H); 7.62 (dd, J=2.4 Hz, 8.5 Hz, 1H); 7.65 (m, 1H); 7.66 (d, J=8.4 Hz, 2H); 8.09 (d, J=8.4 Hz, 2H).

Example 16

Synthesis of ethyl 4"-diethylamino-4'-(3-hydroxypropoxy)-3"-methyl[1,1';3',1"]terphenyl-4-carboxylate

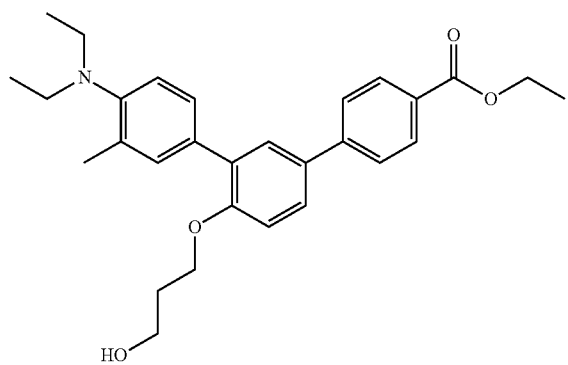 [SMILES: CCOC(=O)c1ccc(-c2ccc(OCCCO)c(-c3ccc(N(CC)CC)c(C)c3)c2)cc1]

a) Preparation of (4-bromo-2-methylphenyl)diethylamine

In a manner similar to that of Example 1b, by reacting 4.7 g (0.12 mol) of sodium hydride with 10 g (54 mmol) of 4-bromo-2-methylaniline, 8 g of (4-bromo-2-methylphenyl)diethylamine are obtained (yield=62%) in the form of a yellow oil.

b) Preparation of 4-diethylamino-3-methylphenylboronic acid

In a manner similar to that of Example 1c, by reacting 8 g of (4-bromo-2-methylphenyl)diethylamine (33 mmol) with 16 mL of a 2.5 M solution of n-butyllithium and 11.5 mL (50 mmol) of triisopropyl borate, 7.6 g of 4-diethylamino-3-methylphenylboronic acid (yield=100%) are obtained in the form of a thick oil.

c) Preparation of ethyl 4'-[3-(tert-butyldimethylsilanyloxy)propoxy]-4"-diethylamino-3"-methyl[1,1';3',1"]terphenyl-4-carboxylate In a manner similar to that of Example 1d, by reacting 1 g (2 mmol) of ethyl 3'-bromo-4'-[3-(tert-butyldimethylsilanyloxy)propoxy]biphenyl-4-carboxylate (obtained in Example 6b) with 630 mg of 4-diethylamino-3-methylphenylboronic acid (3 mmol) in the presence of tetrakis(triphenylphosphine)palladium, 1.1 g of ethyl 4'-[3-(tert-butyldimethylsilanyloxy)propoxy]-4"-diethylamino-3"-methyl[1,1';3',1"]terphenyl-4-carboxylate (yield=95%) are obtained in the form of a pale yellow oil.

d) Synthesis of ethyl 4"-diethylamino-4'-(3-hydroxypropoxy)-3"-methyl[1,1';3',1"]terphenyl-4-carboxylate In a manner similar to that of Example 2b, by reacting 1.1 g of ethyl 4'-[3-(tert-butyldimethylsilanyloxy)propoxy]-4"-diethylamino-3"-methyl[1,1';3',1"]terphenyl-4-carboxylate (1.9 mmol) in 25 mL of tetrahydrofuran with 2.3 mL of 1M tetrabutylammonium fluoride, 130 mg of ethyl 4"-diethylamino-4'-(3-hydroxypropoxy)-3"-methyl[1,1';3',1"]terphenyl-4-carboxylate are obtained (yield=15%).

$^1$H NMR (CDCl$_3$, 400 MHz): 1.06 (t, J=7.4 Hz, 6H); 1.44 (t, J=7.6H, 3H); 2.05 (m, 2H); 2.37 (s, 3H); 3.05 (q, J=7.4 Hz, 4H); 3.78 (q, J=5.6 Hz, 2H); 4.19 (t, J=5.7 Hz, 2H); 4.42 (q, J=7.6 Hz, 2H); 7.09 (d, J=8.5 Hz, 1H); 7.13 (d, J=8.1 Hz, 1H); 7.35-7.39 (m, 2H); 7.57 (dd, J$_1$=2.4 Hz, J$_2$=8.5 Hz, 1H); 7.63 (d, J=2.4 Hz, 1H); 7.68 (d, J=6.7 Hz, 2H); 8.11 (d, J=6.7 Hz, 2H).

Example 17

Synthesis of 4"-diethylamino-4'-(3-hydroxypropoxy)-3"-methyl[1,1';3',1"]terphenyl-4-carboxylic acid

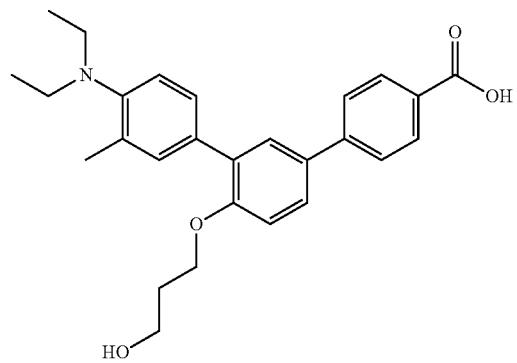 [SMILES: CCN(CC)c1ccc(-c2cc(-c3ccc(C(=O)O)cc3)ccc2OCCCO)cc1C]

In a manner similar to that of Example 12a, by reacting 130 mg (0.3 mmol) of ethyl 4"-diethylamino-4'-(3-hydroxypropoxy)-3"-methyl[1,1';3',1"]terphenyl-4-carboxylate (Example 15d) with 3 mL of 1N sodium hydroxide solution. 60 mg of 4"-diethylamino-4'-(3-hydroxypropoxy)-3"-methyl[1,1';3',1"]terphenyl-4-carboxylic acid are obtained in the form of a white solid (yield=46%, m.p.=208° C.).

HPLC Thermo Aquasil C$_{18}$, 3 microns, 2×150 mm, mobile phase: A (CH$_3$CN/0.1 v/v HCO$_2$H); B (H$_2$O/0.1 v/v HCO$_2$H), Flow rate: 0.5 mL/minutes. Gradient: 0 min: 90% B, 0-20 min: 90-5% B, 20-30 min: 5% B; retention time: 8.95 min, purity: 92%, MS (ESI) m/z 434.3 (M+H)$^+$.

Example 18

Synthesis of ethyl 3"-tert-butyl-4'-(4-hydroxybutoxy)-4"-pyrrolidin-1-yl[1,1';3',1"]terphenyl-4-carboxylate

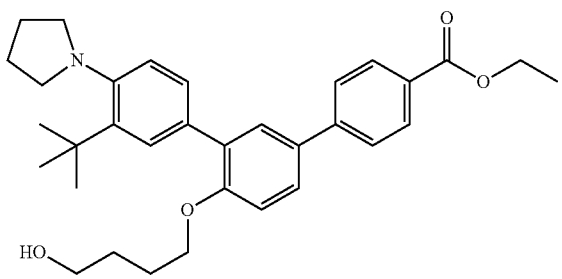 [SMILES: CCOC(=O)c1ccc(-c2ccc(OCCCCO)c(-c3ccc(N4CCCC4)c(C(C)(C)C)c3)c2)cc1]

a) Preparation of 1-(4-bromo-2-tert-butylphenyl)pyrrolidine 5.7 g (0.14 mol) of sodium hydride are suspended in 200 mL of tetrahydrofuran. 10 g (44 mmol) of 4-bromo-2-tert-butylaniline are added, along with 200 mL of dimethyl sulfoxide, added slowly. The mixture turns blue and, after 30 minutes, 13 mL (0.14 mol) of 1,4-dibromobutane are added and the reaction medium is stirred at room temperature for 13 hours. The reaction medium is then poured into saturated ammonium chloride solution and extracted with ethyl acetate, and the organic phase is then washed twice with water, dried and then concentrated to dryness. The residue is purified by chromatography on silica gel (eluent: 90/10 heptane/ethyl acetate). 6.4 g of 1-(4-bromo-2-tert-butylphenyl)pyrrolidine are obtained (yield=52%) in the form of a thick yellow oil.

b) Preparation of 3-tert-butyl-4-pyrrolidinophenylboronic acid

In a manner similar to that of Example 1c, by reacting 4.7 g (17 mmol) of 1-(4-bromo-2-tert-butylphenyl)pyrrolidine with 8 mL of a 2.5M solution of n-butyllithium and 6 mL (26 mmol) of triisopropyl borate, 2.8 g of 3-tert-butyl-4-pyrrolidinophenylboronic acid are obtained (yield=66%).

c) Preparation of ethyl 3"-tert-butyl-4'-hydroxy-4"-pyrrolidin-1-yl[1,1';3',1"]terphenyl-4-carboxylate In a manner similar to that of Example 1d, by reacting 1 g of ethyl 3'-bromo-4'-hydroxy-biphenyl-4-carboxylate (3 mmol) with 1.2 g of 3-tert-butyl-4-pyrrolidinophenylboronic acid (4.5 mmol) in the presence of 5 mL of 2M potassium carbonate (10 mmol) and 360 mg of tetrakis(triphenylphosphine)palladium (Pd(PPh$_3$)$_4$), 900 mg of ethyl 3"-tert-butyl-4'-hydroxy-4"-pyrrolidin-1-yl[1,1';3',1"]terphenyl-4-carboxylate are obtained (yield=63%) in the form of a yellow solid.

d) Preparation of ethyl 3"-tert-butyl-4'-[4-(tert-butyldimethylsilanyloxy)butoxy]-4"-pyrrolidin-4-yl[1,1';3',1"]terphenyl-4-carboxylate In a manner similar to that of Example 2a, by reacting 123 mg of ethyl 3"-tert-butyl-4'-hydroxy-4"-pyrrolidin-1-yl[1,1'; 3',1"]terphenyl-4-carboxylate (0.27 mmol) with 110 mg (0.34 mmol) of caesium carbonate and 80 μL of 1-bromo-4-(tert-butyldimethylsilanyloxy)butane (0.30 mmol), 170 mg of ethyl 3"-tert-butyl-4'-[4-(tert-butyldimethylsilanyloxy)butoxy]-4"-pyrrolidin-1-yl[1,1';3',1"]terphenyl-4-carboxylate are obtained (yield=97%) in the form of an oil.

e) Synthesis of ethyl 3"-tert-butyl-4'-(4-hydroxybutoxy)-4"-pyrrolidin-1-yl[1,1';3',1"]terphenyl-4-carboxylate In a manner similar to that of Example 2b, by reacting 170 mg (0.26 mmol) of ethyl 3"-tert-butyl-4'-[4-(tert-butyldimethylsilanyloxy)butoxy]-4"-pyrrolidin-1-yl[1,1';3',1"]terphenyl-4-carboxylate with 200 μL of a 1M solution of tetrabutylammonium fluoride, 100 mg of ethyl 3"-tert-butyl-4'-(4-hydroxybutoxy)-4"-pyrrolidin-1-yl[1,1';3',1"]terphenyl-4-carboxylate are obtained (yield=71%) in the form of a white solid.

$^1$H NMR (CDCl$_3$-400 MHz): 1.43 (t, J=7.5 Hz, 3H); 1.47 (s, 9H); 1.64-1.71 (m, 2H); 1.85-1.96 (m, 2H); 2.10-2.25 (m, 4H); 3.03 (m, 4H); 3.64 (m, 2H); 4.09 (t, J=6.1 Hz, 2H); 4.41 (t, J=7.5 Hz, 2H); 7.07 (d, J=8.0 Hz, 1H); 7.30 (s, 2H); 7.56-7.65 (m, 3H); 7.67 (d, J=8.2 Hz, 2H); 8.10 (d, J=8.2 Hz, 2H).

Example 19

Synthesis of 3"-tert-butyl-4'-(4-hydroxybutoxy)-4"-pyrrolidin-1-yl[1,1';3',1"]terphenyl-4-carboxylic acid

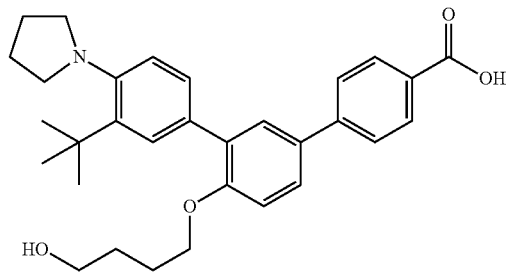 [SMILES: CC(C)(C)c1cc(-c2cc(-c3ccc(C(=O)O)cc3)ccc2OCCCCO)ccc1N1CCCC1]

In a manner similar to that of Example 3, by reacting 100 mg of ethyl 3"-tert-butyl-4'-(4-hydroxybutoxy)-4"-pyrrolidin-1-yl[1,1';3',1"]terphenyl-4-carboxylate (0.18 mmol) with 0.3 mL of 1N sodium hydroxide solution. 50 mg of 3"-tert-butyl-4'-(4-hydroxybutoxy)-4"-pyrrolidin-1-yl[1,1';3',1"] terphenyl-4-carboxylic acid are obtained (yield=56%) in the form of a white solid (m.p.=206° C.).

$^1$H NMR (DMSO, 400 MHz): 1.42 (s, 9H); 1.51 (m, 2H); 1.72 (m, 2H); 1.9 (s, 4H); 3.4 (m, 2H); 4 (m, 2H); 7.2 (d, 1H,

J=8.6 Hz); 7.4 (d, 1H, J=9.9 Hz); 7.45 (d, J=8.2 Hz); 7.55 (s); 7.63 (s, 1H); 7.67 (d, 1H, J=7.34 Hz); 7.8 (d, 2H, J=8.45 Hz); 7.97 (d, 2H, J=8.4 Hz).

Example 20

Synthesis of ethyl 4'-(4-hydroxybutoxy)-4"-pyrrolidin-1-yl-3"-trifluoromethyl[1,1';3',1"]terphenyl-4-carboxylate

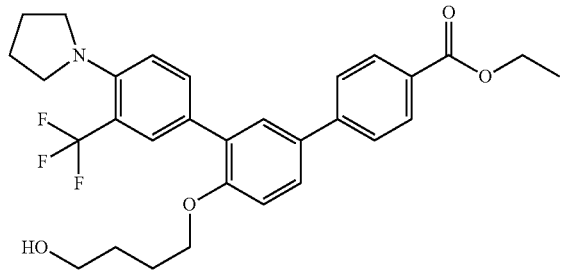 [SMILES: CCOC(=O)c1ccc(-c2ccc(OCCCCO)c(-c3ccc(N4CCCC4)c(C(F)(F)F)c3)c2)cc1]

a) Preparation of 1-(4-Bromo-2-trifluoromethylphenyl)pyrrolidine

In a manner similar to that of Example 18a, by reacting 40 g of 4-bromo-2-trifluoromethylphenylamine (0.167 mol) with 16.6 g of sodium hydride (0.42 mol) and 49.7 mL of 1,4-dibromobutane (0.42 mol), 8.5 g of 1-(4-bromo-2-trifluoromethylphenyl)pyrrolidine (yield=17%) are obtained in the form of a yellow oil.

b) Preparation of 4-pyrrolidino-3-trifluoromethylphenylboronic acid

In a manner similar to that of Example 1c, by reacting 2.3 g (7.9 mmol) of 1-(4-bromo-2-trifluoromethylphenyl)pyrrolidine with 3.8 mL of a 2.5M solution of n-butyllithium and 2.7 mL of triisopropyl borate (12 mmol), 2 g of 4-pyrrolidino-3-trifluoromethylphenylboronic acid are obtained (yield=100%) in the form of a beige-colored solid.

c) Preparation of ethyl 3'-bromo-4'-[4-(tert-butyldimethylsilanyloxy)butoxy]biphenyl-4-carboxylate In a manner similar to that of Example 2a, by reacting 2 g of ethyl 3'-bromo-4'-hydroxy-biphenyl-4-carboxylate (6 mmol) with 2.4 g (7.5 mmol) of caesium carbonate and 1.78 mL of 1-bromo-4-(tert-butyldimethylsilanyloxy)butane (6.7 mmol), 2.8 g of ethyl 3'-bromo-4'-[4-(tert-butyldimethylsilanyloxy)butoxy]biphenyl-4-carboxylate are obtained (yield=97%) in the form of an oil.

d) Preparation of ethyl 4'-[4-(tert-butyldimethylsilanyloxy)butoxy]-4"-pyrrolidin-1-yl-3"-trifluoromethy[1,1';3',1"]terphenyl-4-carboxylate In a manner similar to that of Example 1d, by reacting 500 mg of ethyl 3'-bromo-4'-[4-(tert-butyldimethylsilanyloxy)butoxy]biphenyl-4-carboxylate (1.2 mmol) with 450 mg of 4-pyrrolidino-3-trifluoromethylphenylboronic acid (1.7 mmol) in the presence of 1.5 mL of 2M potassium carbonate (3 mmol) and 40 mg of tetrakis(triphenylphosphine)palladium (Pd(PPh$_3$)$_4$), 400 mg of ethyl 4'-[4-(tert-butyldimethylsilanyloxy)butoxy]-4"-pyrrolidin-1-yl-3"-trifluoromethyl[1,1';3',1"]terphenyl-4-carboxylate are obtained (yield=56%) in the form of a colorless oil.

e) Synthesis of ethyl 4'-(4-hydroxybutoxy)-4"-pyrrolidin-1-yl-3"-trifluoromethyl[1,1';3',1"]terphenyl-4-carboxylate In a manner similar to that of Example 2b, by reacting 400 mg of ethyl 4'-[4-(tert-butyldimethylsilanyloxy)butoxy]-4"-pyrrolidin-1-yl-3"-trifluoromethyl[1,1';3',1"]terphenyl-4-carboxylate (0.6 mmol) with 0.75 mL of a 1N solution of tetrabutylammonium fluoride, 318 mg of ethyl 4'-(4-hydroxybutoxy)-4"-pyrrolidin-1-yl-3"-trifluoromethyl[1,1';3',1"]terphenyl-4-carboxylate are obtained (yield=97%) in the form of a colorless oil.

$^1$H NMR (CDCl$_3$-400 MHz): 1.43 (t, J=7.5 Hz, 3H); 1.55 (m, 2H); 1.68-1.73 (m, 2H); 1.93 (m, 8H); 3.42 (m, 2H); 4.08 (t, J=6.2 Hz, 2H); 4.41 (t, J=7.5 Hz, 2H); 4.43 (bs, 1H); 7.13 (d, J=8.7 Hz, 1H); 7.21 (d, J=8.7 Hz, 1H); 7.67-7.73 (m, 3H); 7.85 (d, J=8.2 Hz, 2H); 7.87 (s, 1H); 7.99 (d, J=8.2 Hz, 2H).

Example 21

Synthesis of 4'-(4-hydroxybutoxy)-4"-pyrrolidin-1-yl-3"-trifluoromethyl[1,1';3',1"]terphenyl-4-carboxylic acid

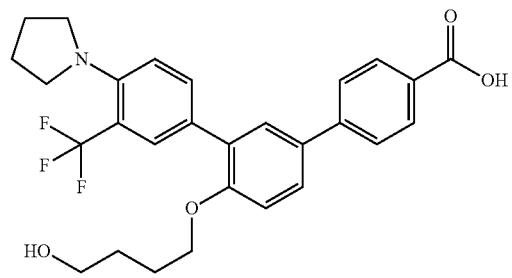

In a manner similar to that of Example 3, by reacting 318 mg of ethyl 4'-(4-hydroxybutoxy)-4"-pyrrolidin-1-yl-3"-trifluoromethyl[1,1';3',1"]terphenyl-4-carboxylate with 6 mL of 1N sodium hydroxide solution, 75 mg of 4'-(4-hydroxybutoxy)-4"-pyrrolidin-1-yl-3"-trifluoromethyl[1,1';3',1"]terphenyl-4-carboxylic acid are obtained (yield=25%) in the form of a white solid (m.p.=237° C.).

$^1$H NMR (DMSO, 400 MHz): 1.55 (m, 2H); 1.73 (m, 2H); 1.93 (m, 8H); 3.42 (m, 2H); 4.08 (t, J=6.2 Hz, 2H); 4.43 (bs,

1H); 7.13 (d, J=8.7 Hz, 1H); 7.21 (d, J=8.7 Hz, 1H); 7.67-7.73 (m, 3H); 7.85 (d, J=8.2 Hz, 2H); 7.87 (s, 1H); 7.99 (d, J=8.2 Hz, 2H); 12.9 (bs, 1H).

Example 22

Synthesis of ethyl 3"-tert-butyl-4'-(3-hydroxypropoxy)-4"-pyrrolidin-1-yl[1,1';3',1"]terphenyl-4-carboxylate

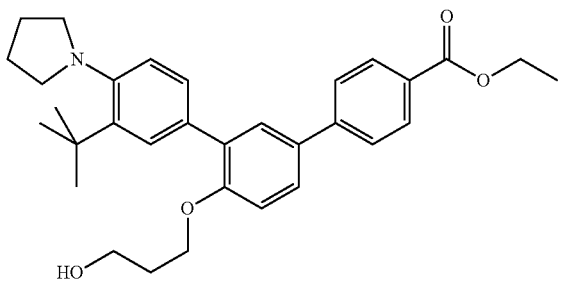 [SMILES: CCOC(=O)c1ccc(-c2ccc(OCCCO)c(-c3ccc(N4CCCC4)c(C(C)(C)C)c3)c2)cc1]

a) Preparation of Ethyl 3"-tert-butyl-4'-[3-(tert-butyldimethylsilanyloxy)propoxy]-4"-pyrrolidin-1-yl[1,1';3',1"]terphenyl-4-carboxylate In a manner similar to that of Example 1d, by reacting 500 mg of ethyl 3'-bromo-4'-[3-(tert-butyldimethylsilanyloxy)propoxy]biphenyl-4-carboxylate obtained in Example 9b (1.2 mmol) with 380 mg of 3-tert-butyl-4-pyrrolidinophenylboronic acid (1.5 mmol) obtained in Example 17b in the presence of 1.3 mL of 2M potassium carbonate (2.6 mmol) and 35 mg of tetrakis(triphenylphosphine)palladium (Pd(PPh$_3$)$_4$), 550 mg of ethyl 3"-tert-butyl-4'-[3-(tert-butyldimethylsilanyloxy)propoxy]-4"-pyrrolidin-1-yl[1,1';3',1"]terphenyl-4-carboxylate are obtained (yield=89%) in the form of a yellow oil.

b) Synthesis of ethyl 3"-tert-butyl-4'-(3-hydroxypropoxy)-4"-pyrrolidin-1-yl[1,1';3',1"]terphenyl-4-carboxylate In a manner similar to that of Example 2b, by reacting 550 mg of ethyl 3"-tert-butyl-4'-[3-(tert-butyldimethylsilanyloxy)propoxy]-4"-pyrrolidin-1-yl[1,1';3',1"]terphenyl-4-carboxylate (0.9 mmol) with 1.1 mL of a 1N solution of tetrabutylammonium fluoride, 260 mg of ethyl 3"-tert-butyl-4'-(3-hydroxypropoxy)-4"-pyrrolidin-1-yl[1,1';3',1"]terphenyl-4-carboxylate are obtained (yield=58%) in the form of a yellow oil.

$^1$H NMR (CDCl$_3$-400 MHz): 1.43 (t, J=7.5 Hz, 3H); 1.47 (s, 9H); 2.05 (m, 2H); 2.10-2.25 (m, 4H); 3.03 (m, 4H); 3.81 (m, 2H); 4.17 (t, J=5.7 Hz, 2H); 4.41 (t, J=7.5 Hz, 2H); 7.07 (d, J=8.0 Hz, 1H); 7.30 (s, 2H); 7.56-7.65 (m, 3H); 7.67 (d, J=8.2 Hz, 2H); 8.10 (d, J=8.2 Hz, 2H).

Example 23

Synthesis of 3"-tert-butyl-4'-(3-hydroxypropoxy)-4"-pyrrolidin-1-yl[1,1';3',1"]terphenyl-4-carboxylic acid

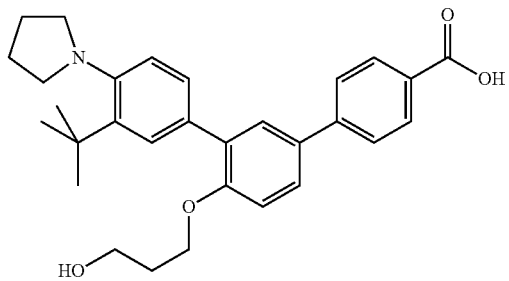 [SMILES: CC(C)(C)c1cc(-c2cc(-c3ccc(C(=O)O)cc3)ccc2OCCCO)ccc1N1CCCC1]

In a manner similar to that of Example 3, by reacting 260 mg of ethyl 3"-tert-butyl-4'-(3-hydroxypropoxy)-4"-pyrrolidin-1-yl[1,1';3',1"]terphenyl-4-carboxylate (0.5 mmol) with 5 mL of 1N sodium hydroxide solution, 120 mg of 3"-tert-butyl-4'-(3-hydroxypropoxy)-4"-pyrrolidin-1-yl[1,1';3',1"]terphenyl-4-carboxylic acid are obtained (yield=48%) in the form of a white solid (m.p.=230° C.).

HPLC Waters Atlantis C$_{18}$, 5 microns, 2×150 mm, mobile phase: A (CH$_3$CN/0.1 v/v HCO$_2$H); B (H$_2$O/0.1 v/v HCO$_2$H), Flow rate: 0.5 mL/minutes. Gradient: 0 min: 90% B, 0-20 min: 90-5% B, 20-30 min: 5% B; retention time: 13.2 min, purity: 97.8%, MS (ESI) m/z 474.3 (M+H)$^+$.

Example 24

Synthesis of ethyl 3"-tert-butyl-4'-(2-hydroxyethoxy)-4"-pyrrolidin-1-yl[1,1';3',1"]terphenyl-4-carboxylate

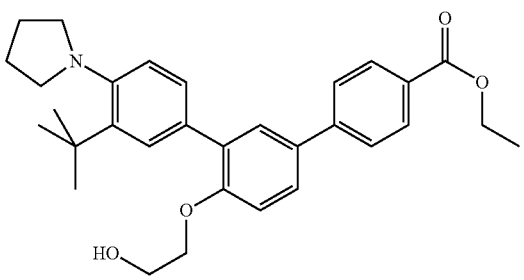 [SMILES: CCOC(=O)c1ccc(-c2ccc(OCCO)c(-c3ccc(N4CCCC4)c(C(C)(C)C)c3)c2)cc1]

a) Preparation of ethyl 4'-(2-acetoxyethoxy)-3"-tert-butyl-4"-pyrrolidin-1-yl[1,1';3',1"]terphenyl-4-carboxylate In a manner similar to that of Example 1d, by reacting 800 mg of ethyl 3'-bromo-4'-(2-acetoxyethoxy)biphenyl-4-carboxylate obtained in Example 13a (2 mmol) with 730 mg of 3-tert-butyl-4-pyrrolidinophenylboronic acid (2.9 mmol) obtained in Example 18b in the presence of 2.6 mL of 2M potassium carbonate (5.2 mmol) and 70 mg of tetrakis(triphenylphosphine)palladium (Pd(PPh$_3$)$_4$), 500 mg of ethyl 4'-(2- acetoxyethoxy)-3"-tert-butyl-4"-pyrrolidin-1-yl[1,1';3',1"]terphenyl-4-carboxylate are obtained (yield=47%) in the form of a yellow oil.

b) Synthesis of ethyl 3"-tert-butyl-4'-(2-hydroxyethoxy)-4"-pyrrolidin-1-yl[1,1';3',1"]terphenyl-4-carboxylate In a manner similar to that of Example 14a, by reacting 110 mg of ethyl 4'-(2-acetoxyethoxy)-3"-tert-butyl-4"-pyrrolidin-1-yl[1,1';3',1"]terphenyl-4-carboxylate (0.2 mmol) with 2 mL of a 1% solution of potassium carbonate in ethanol, 40 mg of ethyl 3"-tert-butyl-4'-(2-hydroxyethoxy)-4"-pyrrolidin-1-yl[1,1';3',1"]terphenyl-4-carboxylate are obtained (yield=39%) in the form of a white solid (m.p.=193° C.).

$^1$H NMR (DMSO, 400 MHz): 1.40 (t, 3H); 1.46 (m, 4H); 1.54 (s, 9H); 1.9 (bs, 4H); 3.0 (bs, 3H); 3.9 (bs, 2H); 4.15 (m, 2H); 4.40 (m, 2H); 7.1 (d, J=8.6 Hz, 1H); 7.4 (d, J=9.9 Hz, 1H); 7.45 (d, J=8.2 Hz, 1H); 7.55 (s, 1H); 7.63 (s, 1H); 7.67 (d, J=7.34 Hz, 1H); 7.80 (d, J=8.45 Hz, 2H); 7.97 (d, J=8.4 Hz, 2H).

Example 25

Synthesis of 3"-tert-butyl-4'-(2-hydroxyethoxy)-4"-pyrrolidin-1-yl[1,1';3',1"]terphenyl-4-carboxylic acid

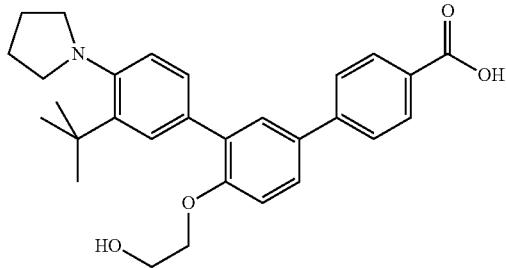 [SMILES: CC(C)(C)c1cc(-c2cc(-c3ccc(C(=O)O)cc3)ccc2OCCO)ccc1N1CCCC1]

In a manner similar to that of Example 6b, by reacting 500 mg (0.9 mmol) of ethyl 4'-(2-acetoxyethoxy)-3"-tert-butyl-4"-pyrrolidin-1-yl[1,1';3',1"]terphenyl-4-carboxylate with 300 mg (8 mmol) of sodium hydroxide, 242 mg of 3"-tert-butyl-4'-(2-hydroxyethoxy)-4"-pyrrolidin-1-yl[1,1';3',1"]terphenyl-4-carboxylic acid are obtained (yield=55%) in the form of a white solid (m.p.=223° C.).

$^1$H NMR (DMSO, 400 MHz): 1.43 (s, 9H); 1.90 (m, 4H); 3.0 (m, 4H); 3.73 (d, J=4.7 Hz, 2H); 4.1 (m, 2H); 4.7 (s, 1H); 7.2 (d, 1H, J=8.6 Hz); 7.48 (m, 2H); 7.59 (d, J=1.6 Hz, 1H); 7.64 (d, J=1.1 Hz, 1H); 7.68 (dd, J=2 Hz, 7.8 Hz, 1H); 7.82 (d, J=8.3 Hz, 2H); 7.99 (d, J=8.4 Hz, 2H).

Example 26

Synthesis of 4'-(3-hydroxypropoxy)-4"-pyrrolidin-1-yl[1,1';3',1"]terphenyl-4-carboxylic acid

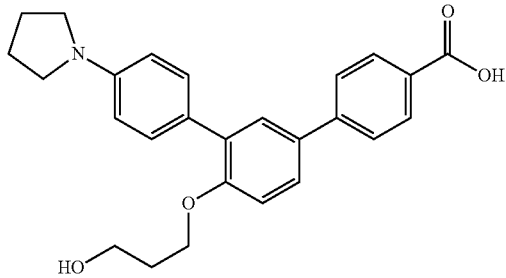 [SMILES: O=C(O)c1ccc(-c2ccc(OCCCO)c(-c3ccc(N4CCCC4)cc3)c2)cc1]

a) Preparation of 4-pyrrolidinophenylboronic acid

In a manner similar to that of Example 1c, by reacting 8.6 g (38 mmol) of 4-bromophenyl-1-pyrrolidine with 18 mL of a 2.5M solution of n-butyllithium and 13 mL of triisopropyl borate (57 mmol), 5 g of 4-pyrrolidinophenylboronic acid are obtained (yield=69%) in the form of a beige-colored solid.

b) Preparation of ethyl 4'-[3-(tert-butyldimethylsilanyloxy)propoxy]-4"-pyrrolidin-1-yl[1,1';3',1"]terphenyl-4-carboxylate In a manner similar to that of Example 1d, by reacting 520 mg of ethyl 3'-bromo-4'-[3-(tert-butyldimethylsilanyloxy)propoxy]biphenyl-4-carboxylate obtained in Example 8b (1 mmol) with 290 mg of 4-pyrrolidinophenylboronic acid (1.5 mmol) in the presence of 1.3 mL of 2M potassium carbonate (2.6 mmol) and 35 mg of tetrakis(triphenylphosphine)palladium (Pd(PPh$_3$)$_4$), 170 mg of ethyl 4'-[3-(tert-butyldimethylsilanyloxy)propoxy]-4"-pyrrolidin-1-yl[1,1';3',1"]terphenyl-4-carboxylate are obtained (yield=30%) in the form of a yellow oil.

c) Preparation of ethyl 4'-(3-hydroxypropoxy)-4"-pyrrolidin-1-yl[1,1';3',1"]terphenyl-4-carboxylate In a manner similar to that of Example 2b, by reacting 170 mg of ethyl 4'-[3-(tert-butyldimethylsilanyloxy)propoxy]-4"-pyrrolidin-1-yl[1,1';3',1"]terphenyl-4-carboxylate (0.3 mmol) with 0.4 mL of a 1N solution of tetrabutylammonium fluoride, 70 mg of ethyl 4'-(3-hydroxypropoxy)-4"-pyrrolidin-1-yl[1,1';3',1"]terphenyl-4-carboxylate are obtained (yield=52%) in the form of a yellow oil.

d) Synthesis of 4'-(3-hydroxypropoxy)-4"-pyrrolidin-1-yl[1,1';3',1"]terphenyl-4-carboxylic acid In a manner similar to that of Example 3, by reacting 70 mg of ethyl 4'-(3-hydroxypropoxy)-4"-pyrrolidin-1-yl[1,1';3', 1"]terphenyl-4-carboxylate (0.16 mmol) with 1.6 mL of 1N sodium hydroxide solution, 10 mg of 4'-(3-hydroxypropoxy)-4"-pyrrolidin-1-yl[1,1';3',1"]terphenyl-4-carboxylic acid are obtained (yield=15%) in the form of a white solid (m.p.=195° C.).

HPLC Thermo Aquasil C$_{18}$, 3 microns, 2×150 mm, mobile phase: A (CH$_3$CN/0.1 v/v HCO$_2$H); B (H$_2$O/0.1 v/v HCO$_2$H), Flow rate: 0.5 mL/minutes. Gradient: 0 min: 90% B, 0-20 min: 90-5% B, 20-30 min: 5% B; retention time: 14.77 min, purity: 93%, MS (ESI) m/z 418.2 (M+H)$^+$.

Example 27

Synthesis of 3"-tert-butyl-4"-diethylamino-4'-hydroxy[1,1';3',1"]terphenyl-4-carboxylic acid

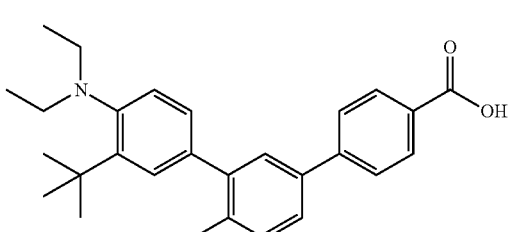

In a manner similar to that of Example 3, by reacting 300 mg of ethyl 3"-tert-butyl-4"-diethylamino-4'-hydroxy[1,1';3',1"]terphenyl-4-carboxylate obtained in Example 1d (0.67 mmol) with 7 mL of 1N sodium hydroxide solution, 236 mg of 3"-tert-butyl-4"-diethylamino-4'-hydroxy[1,1';3',1"]terphenyl-4-carboxylic acid are obtained (yield=84%) in the form of a white solid (m.p.=190° C.).

¹H NMR (DMSO, 400 MHz): 1.06 (t, J=7.4 Hz, 6H); 1.46 (s, 9H); 2.84 (bs, 2H); 2.94 (bs, 2H); 7.05 (d, J=8.5 Hz, 1H); 7.31-7.47 (m, 2H); 7.54-7.62 (m, 3H); 7.78 (d, J=6.7 Hz, 2H); 7.97 (d, J=6.7 Hz, 2H); 9.82 (s, 1H); 12.90 (bs, 1H).

Example 28

Synthesis of ethyl 4"-diethylamino-4'-hydroxy-3"-trifluoromethyl[1,1';3',1"]terphenyl-4-carboxylate

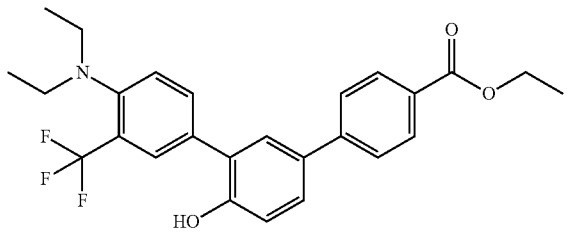 [SMILES: CCOC(=O)c1ccc(-c2ccc(O)c(-c3ccc(N(CC)CC)c(C(F)(F)F)c3)c2)cc1]

a) Preparation of (4-bromo-2-trifluoromethylphenyl)diethylamine

In a manner similar to that of Example 1b, by reacting 10 g of 4-bromo-2-trifluoromethylphenylamine (41 mmol) with 5 g (125 mmol) of 60% sodium hydride and 10 mL (125 mmol) of ethyl iodide, 7 g of (4-bromo-2-trifluoromethylphenyl)diethylamine are obtained (yield=60%) in the form of a yellow oil.

b) Preparation of 4-diethylamino-3-trifluoromethylphenylboronic acid

In a manner similar to that of Example 1c, by reacting 5 g of (4-bromo-2-trifluoromethylphenyl)diethylamine with 8.1 mL of a 2.5 M solution of n-butyllithium and 5.8 mL of triisopropyl borate, 4.3 g of 4-diethylamino-3-trifluoromethylphenylboronic acid are obtained (yield=100%) in the form of a thick orange oil.

c) Synthesis of ethyl 4"-diethylamino-4'-hydroxy-3"-trifluoromethyl[1,1';3',1"]terphenyl-4-carboxylate In a manner similar to that of Example 1d, by reacting 3.5 g of ethyl 3'-bromo-4'-hydroxy-biphenyl-4-carboxylate (10.9 mmol) with 4.3 g of 4-diethylamino-3-trifluoromethylphenylboronic acid (16.4 mmol) in the presence of 14.3 mL of 2M potassium carbonate solution (28.5 mmol) and 380 mg of tetrakis(triphenylphosphine)palladium (0.3 mmol), 1.4 g of ethyl 4"-diethylamino-4'-hydroxy-3"-trifluoromethyl[1,1';3',1"]terphenyl-4-carboxylate are obtained (yield=28%) in the form of a white solid (m.p.=170° C.).

¹H NMR (DMSO, 400 MHz): 0.97 (t, J=7.1 Hz, 6H); 1.44 (t, J=7.6H, 3H); 2.98 (q, J=7.1 Hz, 4H); 5.49 (s, 1H); 7.09 (d, J=8.4 Hz, 1H); 7.60 (m, 2H); 7.69 (d, J=2.3 Hz, 1H); 7.81 (d, J=8.4 Hz, 2H); 7.93 (m, 2H); 7.97 d, J=8.4 Hz, 2H).

Example 29

Synthesis of 4"-diethylamino-4'-hydroxy-3"-trifluoromethyl[1,1';3',1"]terphenyl-4-carboxylic acid

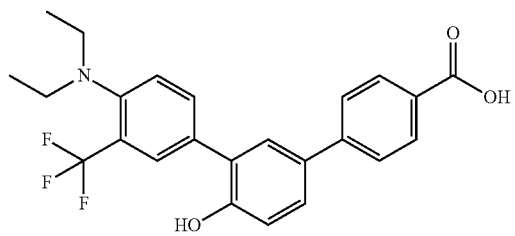 [SMILES: CCN(CC)c1ccc(-c2cc(-c3ccc(C(=O)O)cc3)ccc2O)cc1C(F)(F)F]

In a manner similar to that of Example 3, by reacting 200 mg of ethyl 4"-diethylamino-4'-hydroxy-3"-trifluoromethyl[1,1';3',1"]terphenyl-4-carboxylate (0.44 mmol) with 4 mL of 1N sodium hydroxide solution, 100 mg of 4"-diethylamino-4'-hydroxy-3"-trifluoromethyl[1,1';3',1"]terphenyl-4-carboxylic acid are obtained (yield=50%) in the form of a white solid (m.p. 195° C.).

¹H NMR (DMSO, 400 MHz): 0.97 (t, J=7.1 Hz, 6H); 2.98 (q, J=7.1 Hz, 4H); 7.09 (d, J=8.4 Hz, 1H); 7.60 (m, 2H); 7.69 (d, J=2.3 Hz, 1H); 7.81 (d, J=8.4 Hz, 2H); 7.93 (m, 2H); 7.97 d, J=8.4 Hz, 2H); 10.05 (s, 1H); 12.90 (bs, 1H).

Example 30

Synthesis of 3"-tert-butyl-4"-diethylamino-4'-(4-isopropylaminobutoxy)[1,1';3',1"]terphenyl-4-carboxylic acid

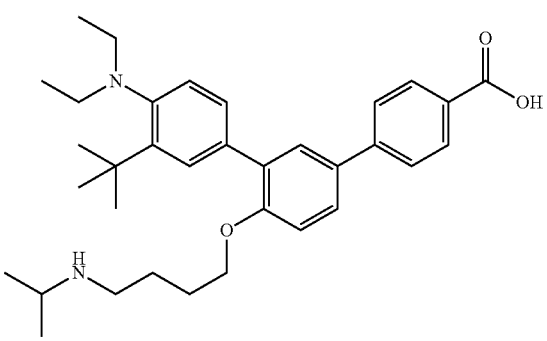 [SMILES: CCN(CC)c1ccc(-c2cc(-c3ccc(C(=O)O)cc3)ccc2OCCCCNC(C)C)cc1C(C)(C)C]

a) Preparation of ethyl 3"-tert-butyl-4"-diethylamino-4'-(4-oxobutoxy)-[1,1';3',1"]terphenyl-4-carboxylate 20 mL of dichloromethane placed in a three-necked flask are cooled to −78° C. and 0.3 mL of oxalyl chloride are added, followed by addition of 0.54 mL of dimethyl sulfoxide diluted in 4 mL of dichloromethane. The reaction medium is stirred at −78° C. for 30 minutes.

900 mg of ethyl 3"-tert-butyl-4"-diethylamino-4'-(4-hydroxybutoxy)-[1,1';3',1"]terphenyl-4-carboxylate obtained in Example 2b (1.7 mmol), dissolved in 55 mL of dichloromethane in the presence of 1 equivalent of triethylamine are added. The reaction medium is stirred at −78° C. for 1 hour and then at room temperature for 12 hours.

The reaction is stopped by adding 100 mL of saturated ammonium chloride solution and then extracted with dichloromethane. The organic phase is washed twice with water, dried over magnesium sulfate, filtered and concentrated. The residue obtained is chromatographed on silica gel (70/30 heptane/ethyl acetate). 720 mg of ethyl 3"-tert-butyl-4"-diethylamino-4'-(4-oxobutoxy)-[1,1';3',1"]terphenyl-4-carboxylate are obtained (yield=78%) in the form of a yellow oil.

b) Preparation of ethyl 3"-tert-butyl-4"-diethylamino-4'-(4-isopropylaminobutoxy)-[1,1';3',1"]terphenyl-4-carboxylate 720 mg of aldehyde ethyl 3"-tert-butyl-4"-diethylamino-4'-(4-oxobutoxy)-[1,1';3',1"]terphenyl-4-carboxylate (1.3 mmol) are dissolved in 15 mL of methanol under a nitrogen atmosphere. 0.6 mL of isopropylamine are then added. The reaction medium is stirred at room temperature for 1 hour 15 minutes. 94 mg of sodium cyanoborohydride are then added to the reaction medium with stirring. The medium is stirred for 3 days. The reaction is stopped by adding 5 mL of water and then extracted with ethyl acetate. The organic phases are combined and dried over magnesium sulfate. The solvents are evaporated off and the residue is precipitated from 8 mL of heptane and filtered through a sinter funnel. 178 mg of ethyl 3"-tert-butyl-4"-diethylamino-4'-(4-isopropylaminobutoxy)-[1,1';3',1"]terphenyl-4-carboxylate are obtained (yield=24%) in the form of a white solid.

c) Synthesis of 3"-tert-butyl-4"-diethylamino-4'-(4-isopropylaminobutoxy)-[1,1';3',1"]terphenyl-4-carboxylic acid In a manner similar to that of Example 3, by reacting 190 mg of ethyl 3"-tert-butyl-4"-diethylamino-4'-(4-isopropylaminobutoxy)-[1,1';3',1"]terphenyl-4-carboxylate (0.3 mmol) with 0.5 mL of 1N sodium hydroxide solution, 45 mg of 3"-tert-butyl-4"-diethylamino-4'-(4-isopropylaminobutog)-[1,1';3',1"]terphenyl-4-carboxylic acid are obtained (yield=25%) in the form of a white solid.

$^1$H NMR (CD$_3$OD, 400 MHz): 1.11 (t, 6H); 1.26 (d, 6H); 1.52 (s, 9H); 1.84 (m, 2H); 1.90 (m, 2H); 2.98 (s, 4H); 3.2 (m, 1H); 3.3 (m, 2H); 4.13 (t, 2H); 7.19 (d, J=8.54 Hz, 1H); 7.36 (s, 1H); 7.42 (s, 1H); 7.61 (s, 1H); 7.65 (s, 2H); 7.72 (d, J=8.36 Hz, 2H); 8.08 (d, J=8.35 Hz, 2H).

Example 31

Synthesis of 3"-tert-butyl-4'-(4-isopropylaminobutoxy)-4"-pyrrolidin-1-yl[1,1';3',1"]terphenyl-4-carboxylic acid

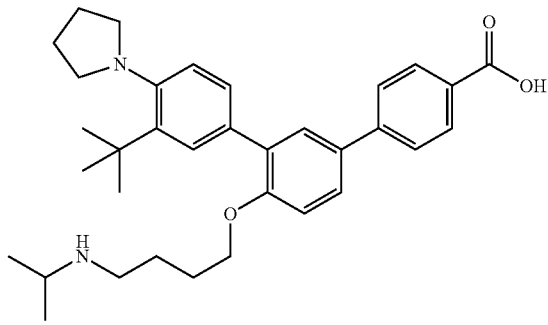 [SMILES: CC(C)NCCCCOc1ccc(-c2ccc(C(=O)O)cc2)cc1-c1ccc(N2CCCC2)c(C(C)(C)C)c1]

a) Preparation of ethyl 3"-tert-butyl-4'-(4-oxobutoxy)-4"-pyrrolidin-1-yl[1,1';3',1"]terphenyl-4-carboxylate In a manner similar to that of Example 30a, by reacting 900 mg of ethyl 3"-tert-butyl-4'-(4-hydroxybutoxy)-4"-pyrrolidin-1-yl[1,1';3',1"]terphenyl-4-carboxylate obtained in Example 18e with 0.3 mL of oxalyl chloride, 0.54 mL of DMSO and 0.25 mL of triethylamine, 700 mg of ethyl 3"-tert-butyl-4'-(4-oxobutoxy)-4"-pyrrolidin-1-yl[1,1';3',1"]terphenyl-4-carboxylate are obtained (yield=78%) in the form of a yellow oil.

b) Preparation of ethyl 3"-tert-butyl-4'-(4-isopropylaminobutoxy)-4"-pyrrolidin-1-yl[1,1';3',1"]terphenyl-4-carboxylate In a manner similar to that of Example 30b, by reacting 700 g of ethyl 3"-tert-butyl-4'-(4-oxobutoxy)-4"-pyrrolidin-1-yl[1,1';3',1"]terphenyl-4-carboxylate with 0.6 mL of isopropylamine and 94 mg of sodium cyanoborohydride, 228 mg of ethyl 3"-tert-butyl-4'-(4-isopropylaminobutoxy)-4"-pyrrolidin-1-yl[1,1';3',1"]terphenyl-4-carboxylate are obtained (yield=24%) in the form of a white solid.

c) Synthesis of 3"-tert-butyl-4'-(4-isopropylaminobutoxy)-4"-pyrrolidin-1-yl[1,1';3',1"]terphenyl-4-carboxylic acid In a manner similar to that of Example 3, by reacting 190 mg of ethyl 3"-tert-butyl-4'-(4-isopropylaminobutoxy)-4"-pyrrolidin-1-yl[1,1';3',1"]terphenyl-4-carboxylate (0.3 mmol) with 2 mL of 1N sodium hydroxide solution, 45 mg of 3"-tert-butyl-4"-diethylamino-4'-(4-isopropylaminobutoxy)-[1,1';3',1"]terphenyl-4-carboxylic acid are obtained (yield=25%) in the form of a white solid.

HPLC Waters Atlantis C$_{18}$, 5 microns, 2×150 mm, mobile phase: A (CH$_3$CN/0.05 v/v CF$_3$CO$_2$H); B (H$_2$O/0.05 v/v CF$_3$CO$_2$H), Flow rate: 1 mL/minutes. Gradient: 0 min: 90% B, 0-20 min: 90-10% B, 20-30 min: 10% B; retention time: 17.5 min, purity: 98%, MS (ESI) m/z 541.3 (M+H)$^+$.

Example 32

Synthesis of ethyl 3"-tert-butyl-4"-diethylamino-4'-(3-hydroxypropyl)[1,1';3',1"]terphenyl-4-carboxylate

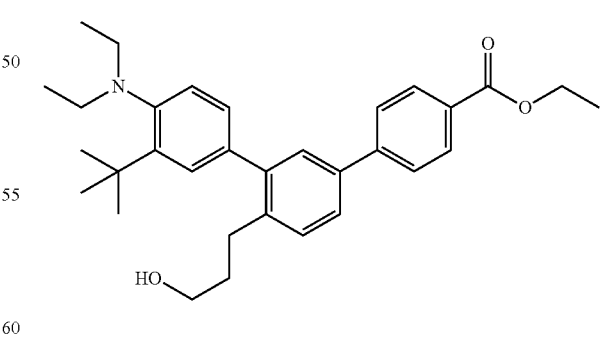

a) Preparation of ethyl 3"-tert-butyl-4"-diethylamino-4'-trifluoromethanesulfonyloxyl[1,1';3',1"]terphenyl-4-carboxylate g of ethyl 3"-tert-butyl-4"-diethylamino-4'-hydroxy[1,1'; 3',1"]terphenyl-4-carboxylate obtained in Example 1d (2.5 mmol) are dissolved at room temperature in 22.4 mL of dichloromethane and the temperature of the reaction medium is then lowered to 0° C.; 112 mg of dimethylaminopyridine are added, followed by addition of 0.88 mL of triethylamine (6 mmol) and dropwise addition of 0.5 mL of triflic anhydride (3 mmol). The temperature is raised to room temperature and the reaction medium is stirred for 20 minutes. The reaction is stopped by adding 30 mL of water and then extracted with 30 mL of dichloromethane. The organic phases are washed with 60 mL of water and then dried over sodium sulfate. The solvents are evaporated off and the residue is then purified by chromatography on silica gel (eluent: heptane). 1.2 g of ethyl 3"-tert-butyl-4"-diethylamino-4'-trifluoromethanesulfonyloxy[1,1';3',1"]terphenyl-4-carboxylate are obtained (yield=79%).

b) Preparation of ethyl 3"-tert-butyl-4"-diethylamino-4'-vinyl[1,1';3',1"]terphenyl-4-carboxylate g of ethyl 3"-tert-butyl-4"-diethylamino-4'-trifluoromethanesulfonyloxy[1,1';3',1"]terphenyl-4-carboxylate (2 mmol) are dissolved at room temperature in 23 mL of dimethylformamide, and 250 mg of LiCl (6 mmol) and 0.74 mL of allyltributyltin (2.4 mmol) are then added. The reaction medium is heated and, at 40° C., 70 mg of dichlorobis(triphenylphosphine)palladium (0.1 mmol) are added and the reaction medium brought to 120° C. and stirred for 20 minutes. The reaction is stopped by adding 30 mL of water and then extracted with 30 mL of ethyl acetate. The organic phases are washed with 80 mL of water and then dried over magnesium sulfate. The solvents are evaporated off and the residue is then purified by chromatography on silica gel (eluent: heptane). 940 mg of ethyl 3"-tert-butyl-4"-diethylamino-4'-vinyl[1,1'; 3',1"]terphenyl-4-carboxylate are obtained (yield=100%).

c) Synthesis of ethyl 3"-tert-butyl-4"-diethylamino-4'-(3-hydroxypropyl)[1,1';3',1"]terphenyl-4-carboxylate 8 g of ethyl 3"-tert-butyl-4"-diethylamino-4'-vinyl[1,1';3',1"]terphenyl-4-carboxylate (17 mmol) are dissolved in 400 mL of THF with stirring and, under cold conditions (ice bath), 6.2 g of 9 borabicyclo[3.3.1]nonane (51 mmol) are added and the ice bath is removed to raise the temperature of the reaction medium to room temperature, at which point the reaction medium is stirred for 1 hour 30 minutes. The temperature of the reaction medium is again reduced to 0° C., 52.8 mL of NaOH (53 mmol) are added portionwise, and the medium is stirred for 10 minutes at 0° C.; 37.3 mL of $H_2O_2$ (426 mmol) are then added dropwise and the reaction medium is warmed to room temperature and then stirred for 2 hours 30 minutes. The reaction is stopped by adding 500 mL of ice-water and then extracted with 500 mL of ethyl acetate. The organic phases are washed with 1 L of water and then dried over magnesium sulfate. The solvents are evaporated off and the residue is then purified by chromatography on silica gel (eluent: 7/3 heptane/ethyl acetate). 6.4 g of ethyl 3"-tert-butyl-4"-diethylamino-4'-(3-hydroxypropyl)[1,1';3',1"]terphenyl-4-carboxylate are obtained (yield=75%).

$^1$H NMR (CDCl$_3$, 400 MHz): 1.13 (t, 6H); 1.44 (t, J=7.5 Hz, 3H); 1.50 (s, 9H); 1.75-1.78 (m, 2H), 2.76 (t, 2H); 2.88 (bs, 2H); 2.97 (bs, 2H); 3.51-3.56 (m, 2H); 4.41 (q, J=7.5 Hz, 2H); 7.19 (m, 1H); 7.32 (d, J=8 Hz, 1H); 7.38-7.42 (m, 2H); 7.55-7.61 (m, 2H); 7.72 (d, J=8.4 Hz, 2H); 8.11 (d, J=8.4 Hz, 2H). 1.09 (t, 6H); 1.5 (s, 9H); 1.7 (m, 2H), 2.75 (t, 2H); 2.90-2.99 (m, 4H); 3.5 (t, 2H); 7.19 (d, 1H, J=7.0 Hz); 7.31 (d, 1H, J=8 Hz); 7.42 (d, 2H, J=8 Hz); 7.56 (s, 2H); 7.76 (d, 2H, J=8.4 Hz); 8.17 (d, 2H, J=8.4 Hz).

Example 33

Synthesis of 3"-tert-butyl-4"-diethylamino-4'-(3-hydroxypropyl)-[1,1';3',1"]terphenyl-4-carboxylic acid

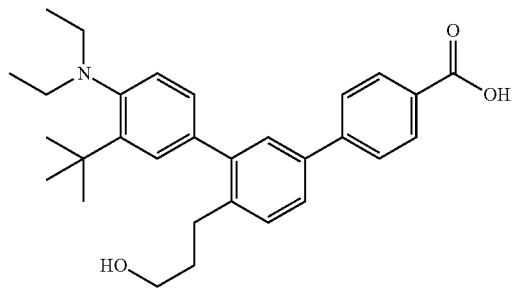 [SMILES: CCN(CC)c1ccc(-c2cc(-c3ccc(C(=O)O)cc3)ccc2CCCO)cc1C(C)(C)C]

In a manner similar to that of Example 3, by reacting 70 mg of ethyl 3"-tert-butyl-4"-diethylamino-4'-(3-hydroxypropyl)-[1,1';3',1"]terphenyl-4-carboxylate (0.14 mmol) with 0.2 mL of 1N sodium hydroxide solution, 64 mg of 3"-tert-butyl-4"-diethylamino-4'-(3-hydroxypropyl)[1,1';3',1"]terphenyl-4-carboxylic acid are obtained (yield=94%) in the form of a white solid (m.p.=95° C.).

$^1$H NMR (CDCl$_3$, 400 MHz): 1.09 (t, 6H); 1.5 (s, 9H); 1.7 (m, 2H), 2.75 (t, 2H); 2.90-2.99 (m, 4H); 3.5 (t, 2H); 7.19 (d, 1H, J=7.0 Hz); 7.31 (d, 1H, J=8 Hz); 7.42 (d, 2H, J=8 Hz); 7.56 (s, 2H); 7.76 (d, 2H, J=8.4 Hz); 8.17 (d, 2H, J=8.4 Hz).

Example 34

Synthesis of ethyl 3"-tert-butyl-4"-diethylamino-4'-(2,3-dihydroxypropyl)[1,1';3',1"]terphenyl-4-carboxylate

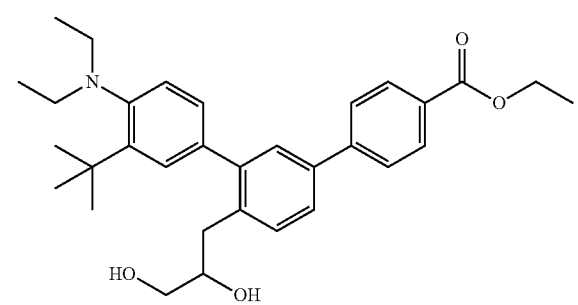 [SMILES: CCOC(=O)c1ccc(-c2ccc(CC(O)CO)c(-c3ccc(N(CC)CC)c(C(C)(C)C)c3)c2)cc1]

150 mg of ethyl 3"-tert-butyl-4"-diethylamino-4'-vinyl[1,1';3',1"]terphenyl-4-carboxylate obtained in Example 32b are dissolved in 10 mL of dichloromethane under a nitrogen atmosphere. 45 mg of N-methylmorpholine are added to the reaction medium, and 0.5 mL of a commercial 2.5% solution of osmium tetroxide in water is then added dropwise and the reaction medium is stirred at room temperature for 3 hours. The reaction is then stopped by adding 10 mL of water and extracted with dichloromethane. The organic phase is washed with water, dried over magnesium sulfate and filtered through a sinter funnel. The solvent is evaporated off and the residue obtained is purified by chromatography on silica (eluent: 7/3 heptane/ethyl acetate). 20 mg of ethyl 3"-tert-butyl-4"-diethylamino-4'-(2,3-dihydroxypropyl)[1,1';3',1"]terphenyl-4-carboxylate are obtained in the form of a white solid.

$^1$H NMR (CDCl$_3$, 400 MHz): 1.12 (t, 6H); 1.43 (t, J=7.5 Hz, 3H); 1.57 (s, 9H); 2.87 (t, 2H); 2.9 (bs, 2H); 2.97 (bs, 2H); 3.33-3.52 (m, 2H); 3.77 (m, 1H); 4.42 (q, J=7.5 Hz, 2H); 7.18 (d, 1H, J=8.0 Hz); 7.31 (d, J=8.0 Hz, 1H); 7.39 (d, J=2 Hz, 1H); 7.47 (d, J=7.8 Hz); 7.57-7.60 (m, 2H); 7.71 (d, J=8.4 Hz, 2H); 8.12 (d, J=8.4 Hz, 2H).

Example 35

Synthesis of 3"-tert-butyl-4"-diethylamino-4'-(2,3-dihydroxypropyl)-[1,1';3',1"]terphenyl-4-carboxylic acid

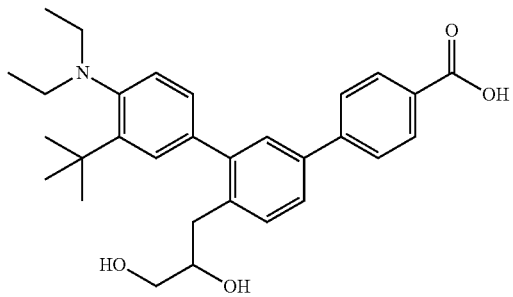 [SMILES: CCN(CC)c1ccc(-c2cc(-c3ccc(C(=O)O)cc3)ccc2CC(O)CO)cc1C(C)(C)C]

In a manner similar to that of Example 3, by reacting 70 mg of ethyl 3"-tert-butyl-4"-diethylamino-4'-(2,3-dihydroxypropyl)-[1,1';3',1"]terphenyl-4-carboxylate (0.14 mmol) with 0.2 mL of 1N sodium hydroxide solution, 58 mg of 3"-tert-butyl-4"-diethylamino-4'-(3-hydroxypropyl)-[1,1';3',1"]terphenyl-4-carboxylic acid are obtained (yield=86%) in the form of a white solid (m.p.=130° C.).

$^1$H NMR (CDCl$_3$, 400 MHz): 1.09 (t, 6H); 1.49 (s, 9H); 2.83 (t, 2H); 2.92 (m, 4H); 3.33-3.52 (m, 2H); 3.77 (m, 1H); 7.18 (d, J=7.9 Hz, 1H); 7.31 (d, J=8 Hz, 1H); 7.42 (d, J=8 Hz, 2H); 7.56 (s, 2H); 7.76 (d, J=8.4 Hz, 2H); 8.17 (d, J=8.4 Hz, 2H).

Example 36

Synthesis of ethyl 4"-(acetylethylamino)-3"-tert-butyl-4'-(3-hydroxypropyl)[1,1';3',1"]terphenyl-4-carboxylate

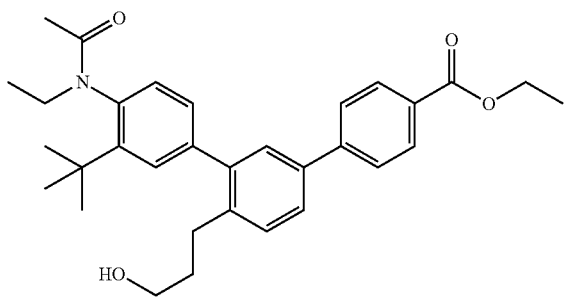 [SMILES: CCOC(=O)c1ccc(-c2ccc(CCCO)c(-c3ccc(N(CC)C(C)=O)c(C(C)(C)C)c3)c2)cc1]

a) Preparation of ethyl 4"-(acetylethylamino)-3"-tert-butyl-4'-trifluoromethanesulfonyloxy[1,1';3',1]terphenyl-4-carboxylate In a manner similar to that of Example 32a, by reacting 7 g (58.5 mmol) of ethyl 4"-(acetylethylamino)-3"-tert-butyl-4'-hydroxy[1,1';3',1"]terphenyl-4-carboxylate obtained in Example 4d with 3.85 g (38 mmol, 5.3 mL) of triethylamine and 0.70 g (5.7 mmol) of 4-dimethylaminopyridine and 5.16 g (18 mmol, 3.1 mL) of triflic anhydride, 2.56 g of ethyl 4"-(acetylethylamino)-3"-tert-butyl-4'-trifluoromethanesulfonyloxy[1,1';3',1"]terphenyl-4-carboxylate are obtained (yield=28%) in the form of a yellow oil.

b) Preparation of ethyl 4"-(acetylethylamino)-4'-allyl-3"-tert-butyl[1,1';3',1"]terphenyl-4-carboxylate In a manner similar to that of Example 32b, by reacting 2.5 g (4.3 mmol) of ethyl 4"-(acetylethylamino)-3"-tert-butyl-4'-trifluoromethanesulfonyloxy[1,1';3',1"]terphenyl-4-carboxylate with 540 mg (12.7 mmol) of lithium chloride and 1.66 g (5.0 mmol) of allyltributyltin and 148 mg (0.2 mmol) of dichlorobis(triphenylphosphine)palladium, 1.67 g of ethyl 4"-(acetylethylamino)-4'-allyl-3"-tert-butyl[1,1';3',1"]terphenyl-4-carboxylate are obtained (yield=80%) in the form of a yellow oil.

c) Synthesis of ethyl 4"-(acetylethylamino)-3"-tert-butyl-4'-(3-hydroxypropyl)[1,1';3',1"]terphenyl-4-carboxylate In a manner similar to that of Example 32c, by reacting 0.2 g (0.41 mmol) of ethyl 4"-(acetylethylamino)-4'-allyl-3"-tert-butyl[1,1';3',1"]terphenyl-4-carboxylate with 150 mg (1.24 mmol) of 9-borabicyclo[3.3.1]nonane, followed by addition of 1.25 mL (1.28 mmol) of 1N sodium hydroxide solution and 1 g (10.3 mmol) of hydrogen peroxide, 205 mg of ethyl 4"-(acetylethylamino)-3"-tert-butyl-4'-(3-hydroxypropyl)-[1,1';3',1"]terphenyl-4-carboxylate are obtained (yield=100%) in the form of a colorless oil.

$^1$H NMR (CDCl$_3$, 400 MHz): 1.28 (t, J=7.2 Hz, 3H); 1.43 (s, 9H); 1.46 (t, 3H); 1.78 (m, 2H); 1.88 (s, 3H); 2.76 (t, J=7.2 Hz, 2H); 2.94 (m, 1H); 3.57 (t, J=6.4 Hz, 2H); 4.43 (t, J=7.2 Hz, 2H); 4.45 (m, 1H); 7.07 (d, J=8.0 Hz, 1H); 7.23 (dd, J$_1$=2 Hz, J$_2$=8.0 Hz, 1H); 7.45 (d, J=8.0 Hz, 1H); 7.52 (d, J=2.0 Hz, 1H); 7.56 (d, J=2.0 Hz, 1H); 7.62 (dd, J$_1$=2.0 Hz, J$_2$=8.0 Hz, 1H); 7.73 (d, J=8.4 Hz, 2H); 8.12 (d, J=8.4 Hz, 2H).

Example 37

Synthesis of 4"-(acetylethylamino)-3"-tert-butyl-4'-(3-hydroxypropyl)-[1,1';3',1"]terphenyl-4-carboxylic acid

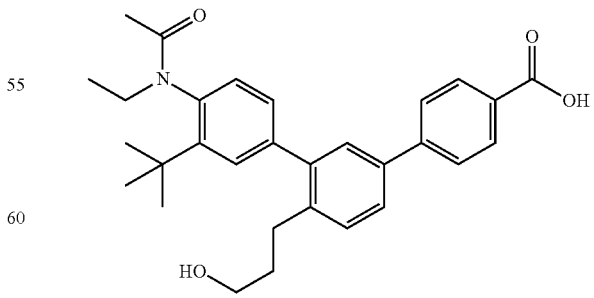

In a manner similar to that of Example 3, by reacting 200 mg of ethyl 4"-(acetylethylamino)-3"-tert-butyl-4'-(3-hydroxypropyl)-[1,1';3',1"]terphenyl-4-carboxylate (0.4 mmol)

with 1 mL of 1N sodium hydroxide solution, 45 mg of 4"-(acetylethylamino)-3"-tert-butyl-4'-(3-hydroxypropyl)-[1,1'; 3',1"]terphenyl-4-carboxylic acid are obtained (yield=23%) in the form of a white solid (m.p.=209° C.).

$^1$H NMR (CDCl$_3$, 400 MHz): 1.21 (t, J=7.2 Hz, 3H); 1.41 (s, 9H); 1.78 (m, 2H); 1.88 (s, 3H); 2.75 (t, J=7.2 Hz, 2H); 2.94 (m, 1H); 3.56 (t, J=6.4 Hz, 2H); 4.45 (m, 1H); 7.07 (d, J=8.0 Hz, 1H); 7.23 (dd, J$_1$=2 Hz, J$_2$=8.0 Hz, 1H); 7.45 (d, J=8.0 Hz, 1H); 7.52 (d, J=2.0 Hz, 1H); 7.56 (d, J=2.0 Hz, 1H); 7.62 (dd, J$_1$=2.0 Hz, J$_2$=8.0 Hz, 1H); 7.73 (d, J=8.4 Hz, 2H); 8.18 (d, J=8.4 Hz, 2H).

Example 38

Synthesis of ethyl 3"-tert-butyl-4'-(3-cyclopropylaminopropyl)-4"-diethylamino[1,1';3',1"]terphenyl-4-carboxylate

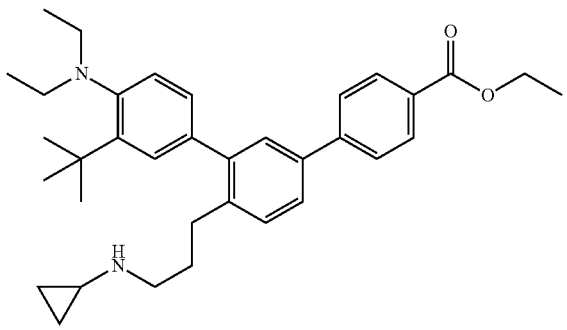 [SMILES: CCOC(=O)c1ccc(-c2ccc(CCCNC3CC3)c(-c3ccc(N(CC)CC)c(C(C)(C)C)c3)c2)cc1]

a) Preparation of ethyl 4'-(3-bromopropyl)-3"-tert-butyl-4"-diethylamino[1,1';3',1"]terphenyl-4-carboxylate 6.4 g of ethyl 3"-tert-butyl-4"-diethylamino-4'-(3-hydroxypropyl)-[1,1';3',1"]terphenyl-4-carboxylate obtained in Example 32c (13 mmol) are dissolved in 128 mL of diethyl ether. The dissolution is performed under cold conditions (0° C.), and 11.4 mL of trioctylphosphine are then added (26 mmol) followed by addition of a solution of 8.5 g of carbon tetrabromide (26 mmol) dissolved in 10 volumes of Et$_2$O added dropwise. The reaction medium is stirred at 0° C. for 30 minutes and then for 1 hour 30 minutes at room temperature. The reaction is stopped by adding 100 mL of water and then extracted with 100 mL of ethyl acetate. The organic phases are washed with 400 mL of water and then dried over magnesium sulfate. The solvents are evaporated off and the residue is then purified by chromatography on silica gel (eluent: 9/1 heptane/ethyl acetate). 6 g of ethyl 4'-(3-bromopropyl)-3"-tert-butyl-4"-diethylamino[1,1';3',1"]terphenyl-4-carboxylate are obtained (yield=83%) in the form of a thick brown oil.

b) Synthesis of ethyl 3"-tert-butyl-4'-(3-cyclopropylaminopropyl)-4"-diethylamino[1,1';3',1"]terphenyl-4-carboxylate 600 mg of ethyl 4'-(3-bromopropyl)-3"-tert-butyl-4"-diethylamino[1,1';3',1"]terphenyl-4-carboxylate (1.1 mmol) are dissolved in 12 mL of ethanol at room temperature, and 0.76 mL of cyclopropylamine (11 mmol) are then added. The medium is brought to reflux, and stirred for 24 hours. After concentrating the reaction mixture, the residue is purified by chromatography on silica gel.

(eluent: 95/5 dichloromethane/methanol). 300 mg of ethyl 3"-tert-butyl-4'-(3-cyclopropylaminopropyl)-4"-diethylamino[1,1';3',1"]terphenyl-4-carboxylate are obtained (yield=53%).

$^1$H NMR (CDCl$_3$, 400 MHz): 0.66 (d, J=6.7 Hz, 2H); 0.95 (d, J=7.3 Hz, 2H); 1.12 (t, J=7.2 Hz, 6H); 1.43 (t, J=7.5 Hz, 3H); 1.49 (s, 9H); 2.01-2.08 (m, 2H); 2.30-2.34 (m, 1H); 2.76 (t, J=7.7 Hz, 2H); 2.83 (t, J=7.7 Hz, 2H); 2.90 (bs, 2H); 2.98 (bs, 2H); 4.42 (q, J=7.5 Hz, 2H); 7.16 (m, 1H); 7.28-7.34 (m, 2H); 7.43 (d, J=8.0 Hz, 1H); 7.52-7.56 (m, 2H); 7.68 (dd, J$_1$=1.9 Hz, J$_2$=6.8 Hz, 2H); 8.10 (d, J$_1$=1.9 Hz, J$_2$=6.8 Hz, 2H).

Example 39

Synthesis of 3"-tert-butyl-4'-(3-cyclopropylaminopropyl)-4"-diethylamino[1,1';3',1"]terphenyl-4-carboxylic acid

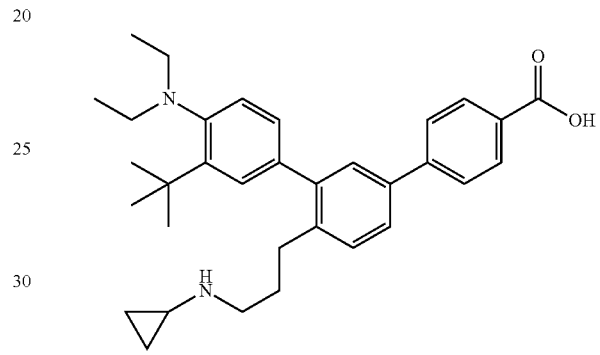

In a manner similar to that of Example 3, by reacting 300 mg of ethyl 3"-tert-butyl-4'-(3-cyclopropylaminopropyl)-4"-diethylamino[1,1';3',1"]terphenyl-4-carboxylate (0.57 mmol) with 2 mL of 1N sodium hydroxide solution, 50 mg of 3"-tert-butyl-4'-(3-cyclopropylaminopropyl)-4"-diethylamino[1,1';3',1"]terphenyl-4-carboxylic acid are obtained (yield=18%) in the form of a white solid (m.p.=189° C.).

$^1$H NMR (CD$_3$OD, 400 MHz): 0.62 (m, 2H); 0.72 (m, 2H); 1.14 (t, J=7.17 Hz, 6H); 1.52 (s, 9H); 1.83 (m, 2H); 2.42 (m, 1H); 2.81 (m, 4H); 2.92 (m, 2H); 3.05 (m, 2H); 7.22 (dd, J$_1$=2.01 Hz, J$_2$=8.04 Hz, 1H); 7.24-7.44 (m, 3H); 7.49 (s, 1H); 7.61-7.67 (m, 3H); 8.03 (d, J=8.39 Hz, 2H).

Example 40

Synthesis of ethyl 3"-tert-butyl-4'-(3-cyclopentylaminopropyl)-4"-diethylamino[1,1';3',1"]terphenyl-4-carboxylate

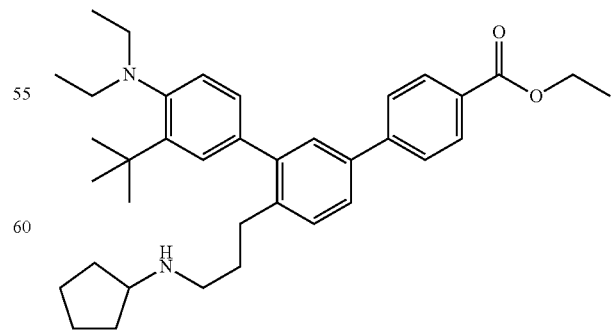

In a manner similar to that of Example 38b, by reacting 600 mg of ethyl 4'-(3-bromopropyl)-3"-tert-butyl-4"-diethylamino[1,1';3',1"]terphenyl-4-carboxylate (1.1 mmol) with 1.1 mL of cyclopentylamine (11 mmol), 560 mg of ethyl 3"-tert-butyl-4'-(3-cyclopentylaminopropyl)-4"-diethylamino[1,1';3',1"]terphenyl-4-carboxylate are obtained (yield=93%) in the form of an orange-colored oil.

$^1$H NMR (CDCl$_3$, 400 MHz): 1.14 (t, J=8.2 Hz, 6H); 1.46 (t, J=7.5 Hz, 3H); 1.49 (s, 9H); 1.52-1.54 m, 2H); 1.75-1.81 (m, 2H); 1.91-1.98 (m, 2H); 2.07-2.13 (m, 2H); 2.73 (t, J=8.2 Hz, 4H); 2.94 (bs, 2H); 3.0 (bs, 2H); 3.20 (m, 1H); 4.41 (q, J=7.5 Hz, 2H); 5.2 (bs, 1H); 7.15 (m, 1H); 7.29-7.32 (m, 2H); 7.44 (d, J=8.0 Hz, 1H); 7.51-7.55 (m, 2H); 7.67 (dd, J$_1$=1.8 Hz, J$_2$=6.7 Hz, 2H); 8.09 (d, J$_1$=1.8 Hz, J$_2$=6.7 Hz, 2H).

Example 41

Synthesis of 3"-tert-butyl-4'-(3-cyclopentylaminopropyl)-4"-diethylamino[1,1';3',1"]terphenyl-4-carboxylic acid

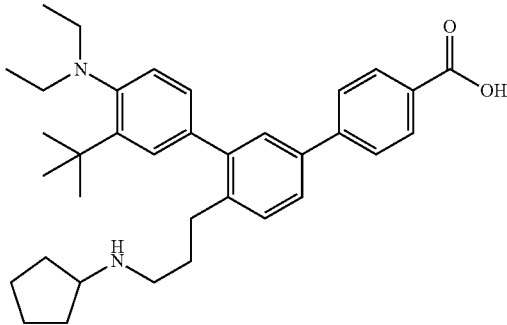 [SMILES: CCN(CC)c1ccc(-c2cc(-c3ccc(C(=O)O)cc3)ccc2CCCNC2CCCC2)cc1C(C)(C)C]

In a manner similar to that of Example 3, by reacting 300 mg of ethyl 3"-tert-butyl-4'-(3-cyclopentylaminopropyl)-4"-diethylamino[1,1';3',1"]terphenyl-4-carboxylate (0.57 mmol) with 2 mL of 1N sodium hydroxide solution, 300 mg of 3"-tert-butyl-4'-(3-cyclopentylaminopropyl)-4"-diethylamino[1,1';3',1"]terphenyl-4-carboxylic acid are obtained (yield=56%) in the form of a white solid (m.p.=255° C.).

$^1$H NMR (CD$_3$OD, 400 MHz): 1.14 (t, J=7.18 Hz, 6H); 1.52 (s, 9H); 1.45-1.95 (m, 8H); 2.03 (m, 2H); 2.82 (t, J=8.06 Hz, 4H); 2.94 (m, 2H); 3.05 (m, 2H); 7.24 (d, J=2.08 Hz, 2H); 7.40 (m, 2H); 7.49 (d, J=1.94 Hz, 1H); 7.62 (m, 3H); 8.0 (d, J=8.4 Hz, 2H).

Example 42

Synthesis of ethyl 3"-tert-butyl-4'-(3-cyclohexylaminopropyl)-4"-diethylamino[1,1';3',1"]terphenyl-4-carboxylate

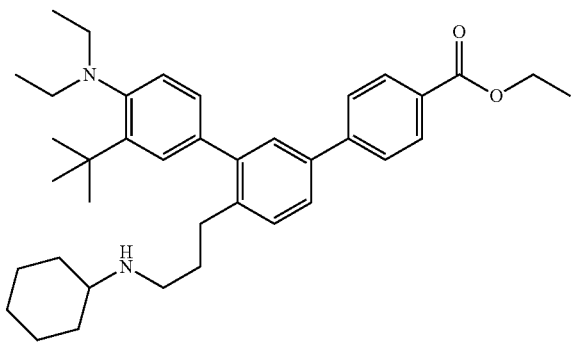 [SMILES: CCOC(=O)c1ccc(-c2ccc(CCCNC3CCCCC3)c(-c3ccc(N(CC)CC)c(C(C)(C)C)c3)c2)cc1]

In a manner similar to that of Example 38b, by reacting 600 mg of ethyl 4'-(3-bromopropyl)-3"-tert-butyl-4"-diethylamino[1,1';3',1"]terphenyl-4-carboxylate (1.1 mmol) with 1.25 mL of cyclohexylamine (11 mmol), 620 mg of ethyl 3"-tert-butyl-4'-(3-cyclohexylaminopropyl)-4"-diethylamino[1,1';3',1"]terphenyl-4-carboxylate are obtained (yield=100%) in the form of an orange-colored oil.

$^1$H NMR (CDCl$_3$, 400 MHz): 1.12 (t, J=7.8 Hz, 6H); 1.46 (t, J=7.5 Hz, 3H); 1.49 (s, 9H); 1.52-1.54 (m, 2H); 1.71-1.81 (m, 4H); 1.91-1.98 (m, 2H); 2.00-2.05 (m, 2H); 2.71 (m, 4H); 2.90 (bs, 2H); 2.90 m, 1H); 2.97 (bs, 2H); 3.20 (m, 1H); 4.2 (bs, 1H); 4.41 (q, J=7.5 Hz, 2H); 7.15 (m, 1H); 7.28-7.33 (m, 2H); 7.45 (d, J=7.8 Hz, 1H); 7.52-7.56 (m, 2H); 7.67 (dd, J$_1$=1.8 Hz, J$_2$=6.7 Hz, 2H); 8.10 (dd, J$_1$=1.8 Hz, J$_2$=6.7 Hz, 2H).

Example 43

Synthesis of 3"-tert-butyl-4'-(3-cyclohexylaminopropyl)-4"-diethylamino[1,1';3',1"]terphenyl-4-carboxylic acid

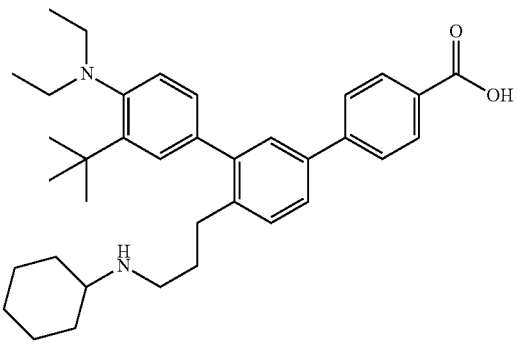 [SMILES: CCN(CC)c1ccc(-c2cc(-c3ccc(C(=O)O)cc3)ccc2CCCNC2CCCCC2)cc1C(C)(C)C]

In a manner similar to that of Example 3, by reacting 600 mg of ethyl 3"-tert-butyl-4'-(3-cyclohexylaminopropyl)-4"-diethylamino[1,1';3',1"]terphenyl-4-carboxylate (1.2 mmol) with 3 mL of 1N sodium hydroxide solution, 400 mg of 3"-tert-butyl-4'-(3-cyclohexylaminopropyl)-4"-diethylamino[1,1';3',1"]terphenyl-4-carboxylic acid are obtained (yield=56%) in the form of a white solid (m.p.=253° C.).

$^1$H NMR (CD$_3$OD, 400 MHz): 1.13 (t, J=7.13 Hz, 6H); 1.52 (s, 9H); 1.58-1.93 (m, 12H); 2.45 (m, 1H); 2.52 (t, J=7.66 Hz, 2H); 2.73 (t, J=7.67 Hz, 2H); 2.52 (m, 2H); 3.05 (m, 2H); 7.22 (dd, J$_1$=2.02 Hz, J$_2$=7.98 Hz, 1H); 7.39 (m, 3H); 7.47 (d, J=1.90 Hz, 1H); 7.61 (m, 3H); 8.02 (d, J=8.28 Hz, 2H).

Example 44

Synthesis of ethyl 3"-tert-butyl-4'-(3-tert-butylaminopropyl)-4"-diethylamino[1,1';3',1"]terphenyl-4-carboxylate

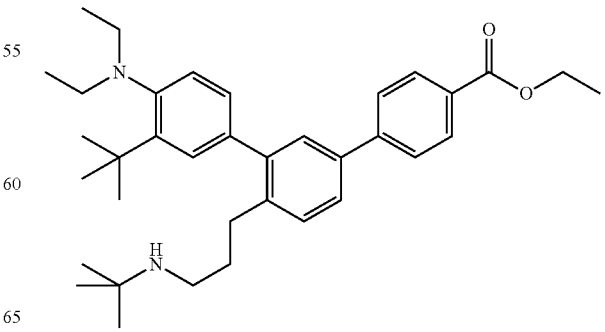

In a manner similar to that of Example 38b, by reacting 600 mg of ethyl 4'-(3-bromopropyl)-3"-tert-butyl-4"-diethylamino[1,1';3',1"]terphenyl-4-carboxylate (1.1 mmol) with 1.06 mL of tert-butylamine (11 mmol), 500 mg of ethyl 3"-tert-butyl-4'-(3-tert-butylaminopropyl)-4"-diethylamino [1,1';3',1"]terphenyl-4-carboxylate are obtained (yield=92%) in the form of an orange-colored oil.

$^1$H NMR (CDCl$_3$, 400 MHz): 1.12 (t, J=7.2 Hz, 6H); 1.43 (t, J=7.5 Hz, 3H); 1.44 (s, 9H); 1.48 (s, 9H); 2.37-2.41 (m, 2H); 2.68-2.74 (m, 4H); 2.85 (bs, 2H); 2.95 (bs, 2H); 4.40 (q, J=7.5 Hz, 2H); 7.12 (m, 1H); 7.28-7.31 (m, 2H); 7.44 (d, J=8.0 Hz, 1H); 7.50-7.53 (m, 2H); 7.63 (d, J=6.8 Hz, 2H); 8.07 (d, J=6.8 Hz, 2H); 8.88 (bs, 1H).

Example 45

Synthesis of 3"-tert-butyl-4'-(3-tert-butylaminopropyl)-4"-diethylamino[1,1';3',1"]terphenyl-4-carboxylic acid

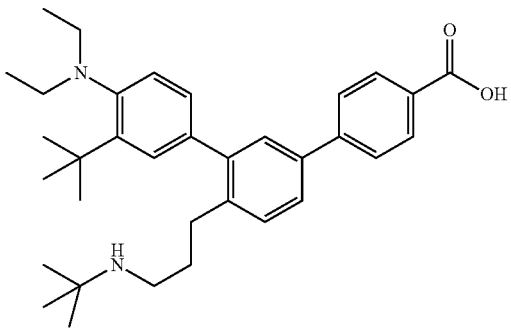 [SMILES: CCN(CC)c1ccc(-c2cc(-c3ccc(C(=O)O)cc3)ccc2CCCNC(C)(C)C)cc1C(C)(C)C]

In a manner similar to that of Example 3, by reacting 480 mg of ethyl 3"-tert-butyl-4'-(3-tert-butylaminopropyl)-4"-diethylamino[1,1';3',1"]terphenyl-4-carboxylate (0.8 mmol) with 3 mL of 1N sodium hydroxide solution, 250 mg of 3"-tert-butyl-4'-(3-tert-butylaminopropyl)-4"-diethylamino [1,1';3',1"]terphenyl-4-carboxylic acid are obtained (yield=55%) in the form of a white solid (m.p.=273° C.).

$^1$H NMR (CDCl$_3$, 400 MHz): 1.10 (t, J=7.2 Hz, 6H); 1.41 (s, 9H); 1.46 (s, 9H); 2.31 (m, 2H); 2.64 (m, 2H); 2.72 (m, 2H); 2.89 (m, 2H); 2.97 (m, 2H); 7.11 (m, 2H); 7.21 (d, J=8.0 Hz, 1H), 7.28 (m, 2H); 7.42-7.47 (m, 3H); 7.94 (d, J=8.0 Hz, 2H); 9.28 (bs, 1H).

Example 46

Synthesis of ethyl 4"-(acetylethylamino)-3"-tert-butyl-4'-(3-cyclopropylaminopropyl)-[1,1';3',1"]terphenyl-4-carboxylate

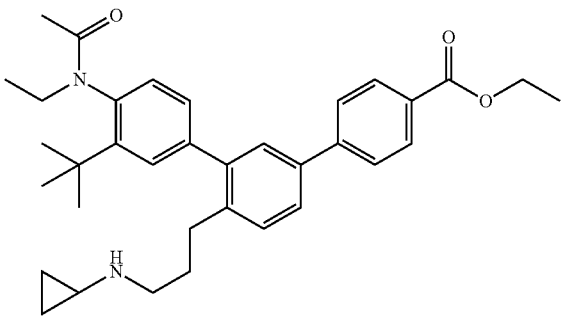 [SMILES: CCOC(=O)c1ccc(-c2ccc(CCCNC3CC3)c(-c3ccc(N(CC)C(C)=O)c(C(C)(C)C)c3)c2)cc1]

a) Preparation of ethyl 4"-(acetylethylamino)-4'-(3-bromopropyl)-3"-tert-butyl[1,1';3',1"]terphenyl-4-carboxylate In a manner similar to that of Example 38a, by reacting 450 mg of ethyl 4"-(acetylethylamino)-3"-tert-butyl-4'-(3-hydroxypropyl)-[1,1';3',1"]terphenyl-4-carboxylate (0.9 mmol) with 665 mg (1.8 mmol, 0.80 mL) of trioctylphosphine and 600 mg (1.80 mmol) of carbon tetrabromide, 500 mg of ethyl 4"-(acetylethylamino)-4'-(3-bromopropyl)-3"-tert-butyl-[1,1';3',1"]terphenyl-4-carboxylate are obtained (yield=98%) in the form of an orange oil.

b) Synthesis of ethyl 4"-(acetylethylamino)-3"-tert-butyl-4'-(3-cyclopropylaminopropyl)-[1,1';3',1"]terphenyl-4-carboxylate In a manner similar to that of Example 38b, by reacting 490 mg of ethyl 4"-(acetylethylamino)-4'-(3-bromopropyl)-3"-tert-butyl[1,1';3',1"]terphenyl-4-carboxylate (0.87 mmol) with 0.6 mL of cyclopropylamine (9 mmol). 270 mg of ethyl 4"-(acetylethylamino)-3"-tert-butyl-4'-(3-cyclopropylaminopropyl)-[1,1';3',1"]terphenyl-4-carboxylate are obtained (yield=57%) in the form of an orange-colored oil.

$^1$H NMR (CDCl$_3$, 400 MHz): 0.73 (m, 4H); 1.27 (t, J=6.8 Hz, 3H); 1.42 (s, 9H); 1.44 (t, 3H); 1.87 (s, 3H); 1.89 (m, 2H); 2.48 (m, 1H); 2.73 (t, J=8.0 Hz, 2H); 2.86 (t, J=8.0 Hz, 2H); 2.97 (m, 1H); 3.89 (m, 2H); 4.42 (q, J=7.4 Hz, 2H); 7.12 (d, J=8.0 Hz, 1H); 7.25 (m, 1H); 7.50-7.53 (m, 3H); 7.58-7.62 (m, 1H); 7.68 (d, J=8.0 Hz, 2H); 8.11 (d, J=8.0 Hz, 2H).

Example 47

Synthesis of 4"-(acetylethylamino)-3"-tert-butyl-4' (3-cyclopropylaminopropyl)[1,1';3',1"]terphenyl-4-carboxylic acid

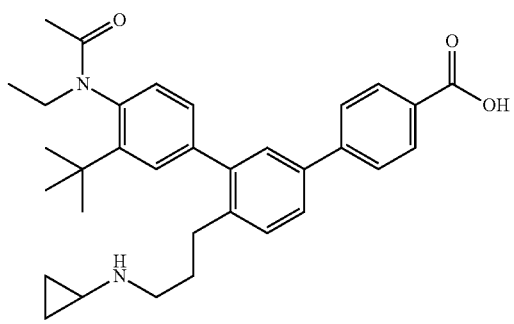 [SMILES: CCN(C(C)=O)c1ccc(-c2cc(-c3ccc(C(=O)O)cc3)ccc2CCCNC2CC2)cc1C(C)(C)C]

In a manner similar to that of Example 3, by reacting 260 mg of ethyl 4"-(acetylethylamino)-3"-tert-butyl-4'-(3-cyclopropylaminopropyl)-[1,1';3',1"]terphenyl-4-carboxylate (0.48 mmol) with 2 mL of 1N sodium hydroxide solution, 100 mg of 4"-(acetylethylamino)-3"-tert-butyl-4'-(3-cyclopropylaminopropyl)-[1,1';3',1"]terphenyl-4-carboxylic acid are obtained (yield=41%) in the form of a white solid (m.p.=190° C.).

$^1$H NMR (CDCl$_3$, 400 MHz): 0.73 (m, 4H); 1.26 (t, J=6.8 Hz, 3H); 1.42 (s, 9H); 1.87 (s, 3H); 1.89 (m, 2H); 2.48 (m, 1H); 2.73 (t, J=8.0 Hz, 2H); 2.86 (t, J=8.0 Hz, 2H); 2.97 (m, 1H); 4.34 (m, 1H); 7.12 (d, J=8.0 Hz, 1H); 2.58 (dd, J$_1$=2.0

Hz, J$_2$=8.0 Hz, 1H); 7.35 (d, J=8.0 Hz, 1H); 7.49 (d, J=2.0 Hz, 1H); 7.51 (dd, J$_1$=2.0 Hz, J$_2$=8.0 Hz, 1H); 7.58-7.62 (m, 3H); 8.00 (d, J=8.0 Hz, 2H).

Example 48

Synthesis of ethyl 3"-tert-butyl-4"-diethylamino-4'-(3-isopropylaminopropyl)-[1,1';3',1"]terphenyl-4-carboxylate

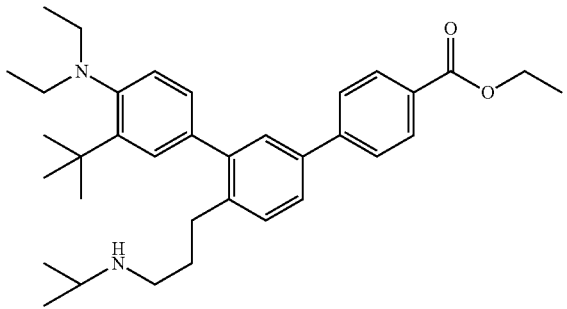 [SMILES: CCOC(=O)c1ccc(-c2ccc(CCCNC(C)C)c(-c3ccc(N(CC)CC)c(C(C)(C)C)c3)c2)cc1]

In a manner similar to that of Example 38b, by reacting 600 mg of ethyl 4'-(3-bromopropyl)-3"-tert-butyl-4"-diethylamino[1,1';3',1"]terphenyl-4-carboxylate (1.1 mmol) with 0.93 mL of isopropylamine (11 mmol), 353 mg of ethyl 3"-tert-butyl-4'-(3-isopropylaminopropyl)-4"-diethylamino[1,1';3',1"]terphenyl-4-carboxylate are obtained (yield=57%) in the form of a white solid.

$^1$H NMR (CDCl$_3$, 400 MHz): 1.16 (t, J=7.2 Hz, 6H); 1.37 (d, J=6.8 Hz, 6H); 1.42 (t, 3H); 1.48 (s, 9H); 2.20-2.25 (m, 2H); 2.75-2.79 (m, 4H); 2.93 (bs, 2H); 3.00 (bs, 2H); 3.28 m, 1H); 4.41 (q, J=7.5 Hz, 2H); 7.15 (d, J=2.0 Hz, 1H); 7.30 (dd, J$_1$=2.1 Hz, J$_2$=8.3 Hz, 2H); 7.44-7.55 (m, 3H); 7.65 (d, J=8.0 Hz, 2H); 8.09 (d, J=8.0 Hz, 2H); 8.98 (bs, 1H).

Example 49

Synthesis of 3"-tert-butyl-4'-(3-isopropylaminopropyl)-4"-diethylamino[1,1';3',1"]terphenyl-4-carboxylic acid

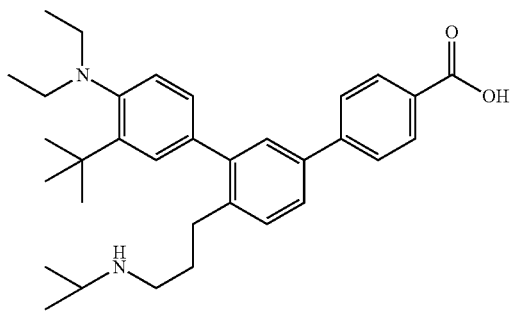 [SMILES: CCN(CC)c1ccc(-c2cc(-c3ccc(C(=O)O)cc3)ccc2CCCNC(C)C)cc1C(C)(C)C]

In a manner similar to that of Example 3, by reacting 350 mg of ethyl 3"-tert-butyl-4'-(3-isopropylaminopropyl)-4"-diethylamino[1,1';3',1"]terphenyl-4-carboxylate (0.67 mmol) with 2 mL of 1N sodium hydroxide solution, 200 mg of 3"-tert-butyl-4'-(3-isopropylaminopropyl)-4"-diethylamino[1,1';3',1"]terphenyl-4-carboxylic acid are obtained (yield=59%) in the form of a white solid (m.p.=253° C.).

$^1$H NMR (CD$_3$OD, 400 MHz): 1.23 (t, J=7.2 Hz, 6H); 1.37 (d, J=6.8 Hz, 6H); 1.62 (s, 9H); 1.97 (m, 2H); 2.74 (m, 1H); 2.89-2.96 (m, 4H); 3.02 (m, 2H); 3.14 (m, 2H); 7.35 (dd, J$_1$=2.0 Hz, 1H); 7.49-7.51 (m, 2H); 7.55 (d, J=8.0 Hz, 1H); 7.62 (d, J=2.0 Hz, 1H); 7.75 (dd, J$_1$=2.0 Hz, J$_2$=8.0 Hz, 1H); 7.78 (d, J=8.0 Hz, 2H); 8.13 (d, J=8.0 Hz, 2H).

Example 50

Synthesis of ethyl 3"-tert-butyl-4'-(3-aminopropyl)-4"-diethylamino[1,1';3',1"]terphenyl-4-carboxylate

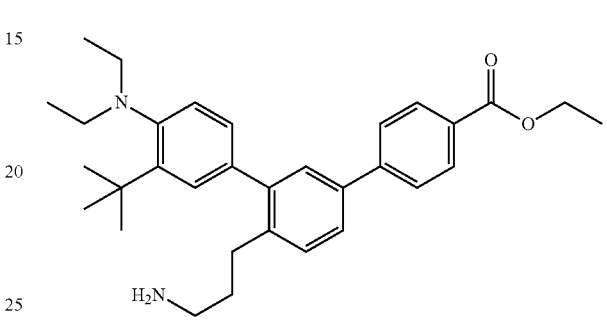

a) Preparation of ethyl 3"-tert-butyl-4"-diethylamino-4'-[3-(1,3-dioxo-1,3-dihydroisoindol-2-yl)propyl]-[1,1';3',1"]terphenyl-4-carboxylate In a 50 mL three-necked flask under a nitrogen atmosphere, equipped with a magnetic stirrer, 1.0 g (1.82 mmol) of ethyl 4'-(3-bromopropyl)-3"-tert-butyl-4"-diethylamino[1,1';3',1"]terphenyl-4-carboxylate, 294 mg (2 mmol) of isoindole-1,3-dione and 276 mg of potassium carbonate (2 mmol) are placed in 20 mL of dimethylformamide. The reaction medium is heated at 100° C. for 3 hours and is then poured into water beforehand and acidified slightly with a 1 mol/L solution of hydrochloric acid, and extracted twice with ethyl acetate. The organic phases obtained are combined and washed with water, dried over anhydrous magnesium sulfate, filtered and evaporated to give a brownish oil. This oil is purified by chromatography on silica (eluent: 80/20 heptane/ethyl acetate) to give 950 mg of ethyl 3"-tert-butyl-4"-diethylamino-4'-[3-(1,3-dioxo-1,3-dihydroisoindol-2-yl)propyl]-[1,1';3',1"]terphenyl-4-carboxylate (yield=86%) in the form of a colorless oil.

b) Synthesis of ethyl 3"-tert-butyl-4'-(3-aminopropyl)-4"-diethylamino[1,1';3',1"]terphenyl-4-carboxylate In a 50 mL three-necked flask under a nitrogen atmosphere, equipped with a magnetic stirrer, 900 mg (1.46 mmol) of ethyl 3"-tert-butyl-4"-diethylamino-4'-[3-(1,3-dioxo-1,3-dihydroisoindol-2-yl)propyl]-[1,1';3',1"]terphenyl-4-carboxylate and 292 mg (5.8 mmol) of hydrazine hydrate are placed in 20 mL of ethanol. The reaction medium is heated to the reflux point of the ethanol for 20 hours and then filtered; the filtrate obtained is evaporated and then purified directly on a column of silica (eluent: 94/6 dichloromethane/methanol) to give, after evaporation of the purest fractions, 545 mg of ethyl 3"-tert-butyl-4'-(3-aminopropyl)-4"-diethylamino[1,1';3',1"]terphenyl-4-carboxylate (yield=77%) in the form of a colorless oil.

¹H NMR (CDCl₃, 400 MHz): 1.12 (t, J=7.2 Hz, 6H); 1.43 (t, J=7.5 Hz, 3H); 1.50 (s, 9H); 1.63-1.69 (m, 2H); 2.61 (t, J=6.9 Hz, 2H); 2.70 (t, J=6.9 Hz, 2H); 2.90 (bs, 2H); 2.95 (bs, 2H); 4.42 (q, J=7.5 Hz, 2H); 7.18 (m, 1H); 7.28-7.32 (m, 1H); 7.38 (d, J=2.0 Hz, 1H); 7.40 (d, J=8.3 Hz, 1H); 7.55-7.59 (m, 2H); 7.71 (d, J=6.8 Hz, 2H); 8.11 (d, J=6.8 Hz, 2H).

Example 51

Synthesis of 3"-tert-butyl-4'-(3-aminopropyl)-4"-diethylamino[1,1';3',1"]terphenyl-4-carboxylic acid

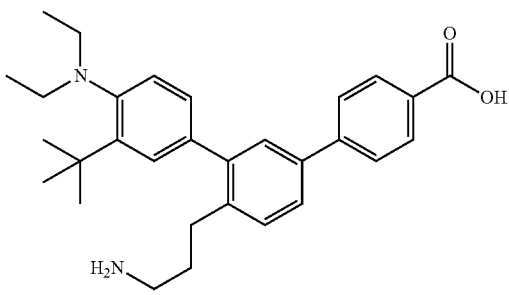

In a manner similar to that of Example 3, by reacting 545 mg of ethyl 3"-tert-butyl-4'-(3-aminopropyl)-4"-diethylamino[1,1';3',1"]terphenyl-4-carboxylate (1.1 mmol) with 4 mL of 1N sodium hydroxide solution, 282 mg of 3"-tert-butyl-4'-(3-aminopropyl)-4"-diethylamino[1,1';3',1"]terphenyl-4-carboxylic acid are obtained (yield=55%) in the form of a white solid (m.p.=272° C.).

¹H NMR (CDCl₃+ECD₃COOD, 400 MHz): 1.11 (t, J=7.2 Hz, 6H); 1.47 (s, 9H); 1.91 (m, 2H); 2.72 (t, J=7.2 Hz, 2H); 2.84 (t, J=7.6 Hz, 2H); 2.92 (m, 2H); 3.00 (m, 2H); 7.14 (dd, J₁=2.0 Hz, J₂=8.0 Hz, 1H); 7.31 (m, 2H); 7.38 (d, J=7.6 Hz, 1H); 7.52-7.56 (m, 2H); 7.70 (d, J=8.4 Hz, 2H); 8.12 (d, J=8.4 Hz, 2H).

Example 52

Synthesis of [3"-tert-butyl-4-carboxy-4'-(3-hydroxypropyl)-[1,1';3',1"]terphenyl-4"-yl]diethylamine hydrochloride

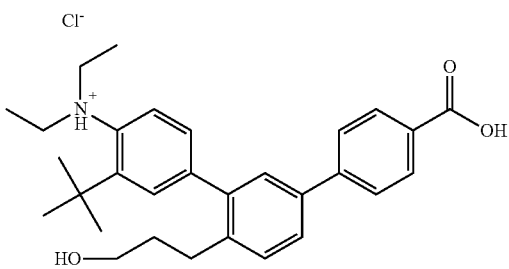 [SMILES: [Cl-] ; CCN(CC)c1ccc(-c2cc(-c3ccc(C(=O)O)cc3)ccc2CCCO)cc1C(C)(C)C]

0.7 g of 3"-tert-butyl-4"-diethylamino-4'-(3-hydroxypropyl)-[1,1';3',1"]terphenyl-4-carboxylic acid (1.5 mmol, 1 eq) obtained in Example 33 are dissolved at room temperature in 7 mL of Et₂O (10 vol) and 7 ml of ethanol, and 0.14 mL of HCl (1.6 mmol, 1.1 eq) is then added.

The reaction mixture is then stirred for 5 hours.
Crystallization is performed in THF.
0.3 g of [3"-tert-butyl-4-carboxy-4'-(3-hydroxypropyl)-[1,1';3',1"]terphenyl-4"-yl]diethylamine hydrochloride is obtained (yield=41%), (m.p.=164-166° C.).

¹H NMR (Methanol, 400 MHz) 1.36 (m, 6H); 1.61 (s, 9H); 1.72 (m, 2H); 1.68 (m, 1H); 2.71 (m, 2H); 3.47 (t, 6.3 Hz, 2H); 3.74 (m, 1H); 3.90 (m, 2H); 3.99 (m, 2H); 7.50 (d, 8.04 Hz, 1H); 7.53 (d, 1.30 Hz, 1H); 7.58 (d, 7.8 Hz, 1H); 7.70 (m, 5.52 Hz, 2H); 7.76 (d, 8.2 Hz, 2H); 7.81 (d, 1H); 8.10 (d, 8.2 Hz, 2H).

Example 53

Synthesis of 3"-tert-butyl-4'-(2-hydroxyethoxy)-4"-(2-oxopyrrolidin-1-yl)-[1,1';3',1"]terphenyl-4-carboxylic acid

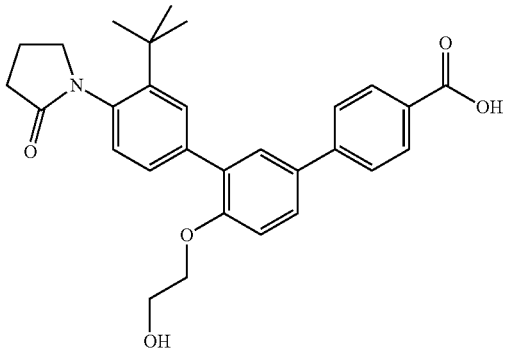 [SMILES: CC(C)(C)c1cc(-c2cc(-c3ccc(C(=O)O)cc3)ccc2OCCO)ccc1N1CCCC1=O]

a) Preparation of N-(2-tert-Butyl-4-bromophenyl)-4-chlorobutanamide 20 g (0.0877 mol; 1 eq.) of 2-tert-butyl-4-bromoaniline (prepared according to Example 1a)) are dissolved in 100 ml of dichloromethane at about 0° C.

13 ml (0.0921 mol; 1.05 eq.) of triethylamine are added, followed, after 15 minutes, by addition of 10.5 ml (0.0921 mol; 1.05 eq.) of 4-chlorobutanoyl chloride.

At the end of the addition, the reaction medium is returned to room temperature and stirred for 1 hour 30 minutes. 70 ml of H₂O are added and the reaction medium is then allowed to settle. The aqueous phase is re-extracted with dichloromethane, and the organic phases are collected and washed successively with aqueous 1M NaHCO₃ and then with H₂O.

The resulting organic phase is dried over sodium sulfate, filtered and concentrated on a rotavapor.

An orange crystalline powder (m=31 g) is obtained, which, after recrystallization from heptane/ethyl acetate medium, gives 24 g of N-(2-tert-butyl-4-bromophenyl)-4-chlorobutanamide (yield=82%).

b) Preparation of 1-(-2-tert-butyl-4-bromophenyl) pyrrolidin-2-one 24 g (0.0721 mol; 1 eq.) of N-(2-tert-butyl-4-bromophenyl)-4-chlorobutanamide (obtained from step a)) are suspended in 170 ml of absolute ethanol.

This suspension is cooled to about 0° C., and 60 ml (0.155 mol; 2.2 eq.) of sodium ethoxide as a 21% w/w solution in ethanol are added slowly. The reaction medium is then brownish-colored; it is stirred for 15 hours at room temperature. 200 ml of $H_2O$ are added and the mixture is extracted with heptane/ethyl acetate and washed with $H_2O$ until the aqueous phase is neutral. The organic phase is concentrated on a rotavapor: 20 g of an orange crystalline powder are isolated and recrystallized from 200 ml of diisopropyl ether. Finally, 16 g of 1-(−2-tert-butyl-4-bromophenyl)pyrrolidin-2-one are obtained (yield=75%).

c) Preparation of 1-[2-tert-butyl-4-(4,4,5,5-tetramethyl[1,3,2]dioxaborolan-2-yl)phenyl]pyrrolidin-2-one 6.5 g (0.022 mol; 1 eq.) of 1-(−2-tert-butyl-4-bromophenyl)pyrrolidin-2-one (obtained in step b)), 5.85 g (0.023 mol; 1.05 eq.) of bis(pinacolato)diborane and 6.46 g (0.066 mol; 3 eq.) of potassium acetate are suspended in 50 ml of dimethylformamide. After bubbling nitrogen into the reaction medium for 15 minutes, 540 mg (0.66 mmol; 0.03 eq.) of catalyst ($PdCl_2$(dppf)) are added and the medium is then heated at 90° C. until the reaction is complete.

The reaction medium cooled to room temperature and filtered through a sinter funnel packed with Celite; the filter cake is rinsed thoroughly with ethyl acetate, and $H_2O$ is added to the filtrate, which is then allowed to settle. The organic phase obtained is then concentrated on a rotavapor to give a residue, which is purified by chromatography on silica.

5.7 g of 1-[2-tert-butyl-4-(4,4,5,5-tetramethyl[1,3,2]dioxaborolan-2-yl)phenyl]pyrrolidin-2-one are isolated in the form of a white powder (yield=75%).

d) Preparation of ethyl[3'-bromo-4'-(2-hydroxyethoxy)]biphenyl-4-benzoate 70 g (0.218 mol; 1 eq.) of ethyl[3'-bromo-4'-hydroxy]biphenyl-4-benzoate are suspended with 45.2 g (0.327 mol; 1.5 eq.) of potassium carbonate, in 700 ml of methyl ethyl ketone.

39 ml (0.545 mol; 2.5 eq.) of 2-bromoethanol are added in a single portion, and this suspension is heated to reflux. The reaction medium is maintained under these conditions for 14 hours and then cooled to room temperature.

The reaction medium is filtered and the filtrate is concentrated. The residue is added to ethyl acetate, washed with $H_2O$ and once again concentrated. 90 g of a powder are obtained, which product is recrystallized from heptane/ethyl acetate to give after drying 65 g of ethyl[3'-bromo-4'-(2-hydroxyethoxy)]biphenyl-4-benzoate, in the form of a white crystalline powder (yield=82%).

f) Preparation of [3'-bromo-4'-(2-hydroxyethoxy)]biphenyl-4-carboxylic acid 63 g (0.173 mol; 1 eq.) of ethyl[3'-bromo-4'-(2-hydroxyethoxy)]biphenyl-4-benzoate (obtained in step d)) are dissolved in 300 ml of tetrahydrofuran. 10.9 g (0.259 mol; 1.5 eq.) of lithium hydroxide monohydrate as a solution in 70 ml of $H_2O$ are added at room temperature.

The reaction medium is refluxed for about 1 hour 30 minutes.

The reaction medium is then cooled to room temperature and dilute hydrochloric acid solution is added (330 ml; ~1M).

100 ml of $H_2O$ are added and this suspension is cooled to about 0° C.; it is maintained at this temperature for about 15 minutes then filtered. After drying, 59 g of a white powder are obtained.

This product is slurried in 240 ml of acetone for two hours at room temperature and then filtered and oven-dried. 55 g of [3'-bromo-4'-(2-hydroxyethoxy)]biphenyl-4-carboxylic acid are thus isolated (yield=95%).

g) Synthesis of 3"-tert-butyl-4'-(2-hydroxyethoxy)-4"-(2-oxopyrrolidin-1-yl)-[1,1';3',1"]terphenyl-4-carboxylic acid 1.3 g (3.78 mmol; 1 eq.) of 1-[2-tert-butyl-4-(4,4,5,5-tetramethyl[1,3,2]dioxaborolan-2-yl)phenyl]pyrrolidin-2-one (obtained in step c)) and 1.68 g (4.98 mmol; 1.3 eq.) of [3'-bromo-4'-(2-hydroxyethoxy)]biphenyl-4-carboxylic acid (obtained in step e)) are dissolved in 8 ml of dimethylformamide. 7.5 ml (0.015 mol; 3.97 eq.) of aqueous 2M potassium carbonate solution and 35 mg (0.10 mmol; 0.026 eq.) of 2-dicyclohexylphosphinobiphenyl are then added.

A stream of nitrogen is bubbled through the medium for about 10 minutes, and 11 mg (0.08 mmol; 0.014 eq.) of palladium acetate are introduced. The mixture is then heated to about 90° C. and maintained under these conditions for 4-6 hours.

The reaction medium is then cooled to room temperature, filtered through a sinter funnel packed with Celite and rinsed with a minimum amount of dimethylformamide, and dilute hydrochloric acid solution (~2M) is added to the filtrate.

After stirring for 4 hours, the precipitate formed is filtered off, rinsed to neutrality with $H_2O$, filtered off by suction and oven-dried. 1.05 g of 3"-tert-butyl-4'-(2-hydroxyethoxy)-4"-(2-oxopyrrolidin-1-yl)-[1,1';3',1"]terphenyl-4-carboxylic acid are thus isolated (yield=57%).

Example 54

Synthesis of 3"-tert-butyl-4"-ethylamino-4'-(3-hydroxypropoxy)-[1,1';3',1"]terphenyl-4-carboxylic acid

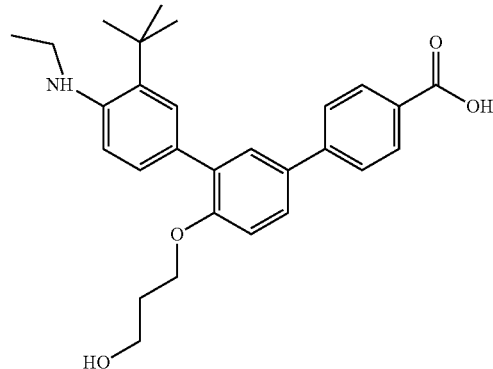 [SMILES: CCNc1ccc(-c2cc(-c3ccc(C(=O)O)cc3)ccc2OCCCO)cc1C(C)(C)C]

a) Preparation of N-(2-tert-butyl-4-bromophenyl)acetamide 18 g (0.079 mol; 1 eq.) of 2-tert-butyl-4-bromoaniline (prepared according to Example 1a)) are dissolved in 150 ml of dichloromethane at about 0° C. 12.1 ml (0.087 mol; 1.1 eq.) of triethylamine are added, followed, after 15 minutes, by addition of 6.2 ml (0.087 mol; 1.1 eq.) of acetyl chloride. The mixture is warmed to room temperature at the end of addition and stirred for 2 hours. 70 ml of $H_2O$ are added and the resulting mixture is allowed to settle. The aqueous phase is re-extracted with dichloromethane, and the organic phases are combined, washed to neutrality with H₂O, dried over sodium sulfate, filtered and concentrated on a rotavapor.

21 g of a beige-colored crystalline powder are obtained, which product is slurried in heptane for 2 hours at room temperature, chilled and then filtered. After drying, 17.6 g of N-(2-tert-butyl-4-bromophenyl)acetamide are obtained (yield=83%).

b) Preparation of (2-tert-butyl-4-bromophenyl)ethylamine 17.5 g (0.065 mol; 1 eq.) of N-(2-tert-butyl-4-bromophenyl)acetamide (obtained in step a)) are suspended in 100 ml of tetrahydrofuran.

162 ml (0.162 mol; 2.5 eq.) of 1M borane-tetrahydrofuran complex are added and the mixture is heated to reflux. The conditions are maintained for about 12 hours.

The reaction mixture is cooled to room temperature and 70 ml of methanol are added to destroy the excess borane. The mixture is stirred until the evolution of gas has ceased and is then concentrated on a rotavapor. The oil obtained is dissolved in ethyl acetate and washed with saturated aqueous ammonium chloride solution and then with H₂O.

The resulting solution is concentrated and purified by filtration on silica; 13 g of (2-tert-butyl-4-bromophenyl)ethylamine are thus obtained in the form of a relatively colorless oil (yield=78%).

c) Preparation of [2-tert-butyl-4-(4,4,5,5-tetramethyl[1,3,2]dioxaborolan-2-yl)phenyl]ethylamine 13 g (0.0507 mol; 1 eq.) of (2-tert-butyl-4-bromophenyl)ethylamine (obtained in step b)), 15.5 g (0.061 mol; 1.2 eq.) of bis(pinacolato)diborane and 15 g (0.152 mol; 3 eq.) of potassium acetate are suspended in 75 ml of dimethylformamide. After bubbling a stream of nitrogen through the reaction medium for 15 minutes, 1.66 g (2.03 mmol; 0.04 eq.) of catalyst (PdCl₂(dppf)) are added and the medium is heated at about 90° C. for about 10 hours.

The reaction medium is cooled to room temperature and filtered through a sinter funnel packed with Celite; the filter cake is rinsed thoroughly with ethyl acetate, and H₂O is added to the filtrate and the phases are allowed to separate by settling. The organic phase obtained is thus concentrated on a rotavapor to give a residue, which is chromatographed on a column of silica. 7 g of [2-tert-butyl-4-(4,4,5,5-tetramethyl[1,3,2]dioxaborolan-2-yl)phenyl]ethylamine are isolated in the form of an orange crystalline powder (yield=45%).

d) Preparation of ethyl[3'-bromo-4'-(3-hydroxypropoxy)]biphenyl-4-benzoate 47 g (0.146 mol; 1 eq.) of ethyl[3'-bromo-4'-hydroxy]biphenyl-4-benzoate are suspended with 30.3 g (0.219 mol; 1.5 eq.) of potassium carbonate in 470 ml of methyl ethyl ketone. 13.5 ml (0.154 mol; 1.05 eq.) of 3-bromopropan-1-ol are added in a single portion and this suspension is brought to reflux. These conditions are maintained for 14 hours and the mixture is then cooled to room temperature. The medium is filtered and the filtrate is concentrated. The residue is taken up in ethyl acetate, washed with H₂O and then concentrated again. 60 g of a powder are isolated, and are recrystallized from a heptane/ethyl acetate mixture to give, after drying, 40 g of ethyl[3'-bromo-4'-(3-hydroxypropoxy)]biphenyl-4-benzoate in the form of an off-white crystalline powder (yield=72%).

e) Preparation of ethyl[3'-bromo-4'-(3-acetoxypropoxy)]biphenyl-4-benzoate 2 g (5.27 mmol; 1 eq.) of ethyl[3'-bromo-4'-(3-hydroxypropoxy)]biphenyl-4-benzoate (obtained in step d)) are dissolved in 20 ml of dichloromethane. 64 mg (0.527 mmol; 0.1 eq.) of 4-dimethylaminopyridine and 430 μl (5.27 mmol; 1 eq.) of pyridine are added at room temperature. The mixture is stirred for 15 minutes at room temperature, and 750 μl (7.91 mmol; 1.5 eq.) of acetic anhydride are then added. The mixture is maintained at room temperature for 1 hour. H₂O is added, the phases are allowed to separate by settling and the organic phase is neutralized with aqueous 1M NHCO₃ solution. The resulting organic phase is washed with H₂O until neutral and concentrated on a rotavapor. 2.2 g of a powder are obtained, and are recrystallized from a heptane/ethyl acetate mixture. This gives, after drying, 1.9 g of ethyl[3'-bromo-4'-(3-acetoxypropoxy)]biphenyl-4-benzoate in the form of a white crystalline powder (yield=85%).

f) Preparation of ethyl 4'-(3-acetoxypropoxy)-3"-tert-butyl-4"-ethylamino[1,1';3',1"]terphenyl-4-benzoate 720 mg (2.3 mmol; 1 eq.) of [2-tert-butyl-4-(4,4,5,5-tetramethyl[1,3,2]dioxaborolan-2-yl)-phenyl]ethylamine (obtained in step c)) and 1 g (2.3 mmol; 1 eq.) of ethyl [3'-bromo-4'-(3-acetoxypropoxy)]biphenyl-4-benzoate (obtained in step e)) are dissolved in 10 ml of dimethylformamide. 2.5 ml (5 mmol; 2 eq.) of aqueous 2M tribasic potassium phosphate solution and 16.1 mg (0.046 mmol; 0.02 eq.) of 2-dicyclohexylphosphinobiphenyl are added at room temperature.

After bubbling a stream of nitrogen into the medium for about 10 minutes, 5.2 mg (0.023 mmol; 0.01 eq.) of palladium acetate are added and the mixture is heated at 80° C. for about 5 hours. The reaction medium is filtered through a sinter funnel packed with Celite and rinsed thoroughly with ethyl acetate. Saturated aqueous ammonium chloride solution is then added to the filtrate, the phases are allowed to separate by settling and the organic phase is washed with H₂O and then dried over sodium sulfate. The organic phase is concentrated; the oil obtained is chromatographed on a column of silica, and 900 mg of ethyl 4'-(3-acetoxypropoxy)-3"-tert-butyl-4"-ethylamino[1,1';3',1"]terphenyl-4-benzoate are isolated (yield=73%).

g) Synthesis of 3"-tert-butyl-4"-ethylamino-4'-(3-hydroxypropoxy)-[1,1';3',1"]terphenyl-4-carboxylic acid 900 mg (1.74 mmol; 1 eq.) of ethyl 4'-(3-acetoxypropoxy)-3"-tert-butyl-4"-ethylamino-[1,1';3',1"]terphenyl-4-benzoate are dissolved in 10 ml of absolute ethanol. 312 mg (7.8 mmol; 4.5 eq.) of sodium hydroxide and 4 ml of H₂O are added at room temperature and the mixture is then heated to reflux. These conditions are maintained for about 1 hour 30 minutes. The reaction medium is concentrated to a small volume; H₂O is added to the precipitate formed, and the mixture is then acidified with acetic acid to pH ~4-5. This suspension is fluidized by adding H₂O and stirred at room temperature for 1 hour. The resulting mixture is filtered through a sinter funnel, rinsed with H₂O until the filtrate is neutral, and oven-dried. 694 mg of 3"-tert-butyl-4"-ethylamino-4'-(3-hydroxypropoxy)-[1,1';3',1"]terphenyl-4-carboxylic acid are thus obtained in the form of a white powder (yield=89%).

Example 55

Transactivation Test

The activation of receptors with an agonist (activator) in HeLa cells leads to the expression of a reporter gene, luciferase, which, in the presence of a substrate, generates light. The activation of the receptors may thus be measured by quantifying the luminescence produced after incubating the cells in the presence of a reference agonist. The inhibitory products displace the agonist from its site, thus preventing activation of the receptor. The activity is measured by quantifying the reduction in light produced. This measurement makes it possible to determine the inhibitory activity of the compounds according to the invention.

In this study, a constant is determined which is the affinity of the molecule for the receptor. Since this value can fluctuate depending on the basal activity and the expression of the receptor, it is referred to as the Kd apparent (KdApp).

To determine this constant, "crossed curves" of the test product against a reference agonist, 4-[2-(5,5,8,8-tetramethyl-5,6,7,8-tetrahydro-2-naphthyl)propenyl]benzoic acid, are performed in 96-well plates. The test product is used at 10 concentrations and the reference agonist at 7 concentrations. In each well, the cells are in contact with a concentration of the test product and a concentration of the reference agonist, 4-[2-(5,5,8,8-tetramethyl-5,6,7,8-tetrahydro-2-naphthyl)propenyl]benzoic acid. Measurements are also taken for the total agonist (4-[2-(5,5,8,8-tetramethyl-5,6,7,8-tetrahydro-2-naphthyl)propenyl]benzoic acid) and inverse agonist, 4-{(E)-3-[4-(4-tert-butylphenyl)-5,5,8,8-tetramethyl-5,6,7,8-tetrahydro-2-naphthyl]-3-oxopropenyl}benzoic acid, controls.

These crossed curves make it possible to determine the $AC_{50}$ values (concentration at which 50% activation is observed) for the reference ligand at various concentrations of test product. These $AC_{50}$ values are used to calculate the Schild regression by plotting a straight line corresponding to the Schild equation ("quantitation in receptor pharmacology" Terry P. Kenakin, *Receptors and Channels*, 2001, 7, 371-385).

The HeLa cell lines used are stable transfectants containing the plasmids ERE-βGlob-Luc-SV-Neo (reporter gene) and RAR (α, β, γ) ER-DBD-puro. These cells are inoculated into 96-well plates at a rate of 10,000 cells per well in 100 μl of DMEM medium without phenol red, and supplemented with 10% defatted calf serum. The plates are then incubated at 37° C. and 7% $CO_2$ for 4 hours.

The various dilutions of the test products, of the reference ligand (4-[2-(5,5,8,8-tetramethyl-5,6,7,8-tetrahydro-2-naphthyl)propenyl]benzoic acid), of the 100% control (100 nM 4-[2-(5,5,8,8-tetramethyl-5,6,7,8-tetrahydro-2-naphthyl)propenyl]benzoic acid) and of the 0% control (500 nM 4-{(E)-3-[4-(4-tert-butylphenyl)-5,5,8,8-tetramethyl-5,6,7,8-tetrahydro-2-naphthyl]-3-oxopropenyl}benzoic acid) are added at a rate of 5 μl per well. The plates are then incubated for 18 hours at 37° C. and 7% $CO_2$.

The culture medium is removed by turning over and 100 μl of a 1:1 PBS/luciferine mixture is added to each well. After 5 minutes, the plates are read using the luminescence reader.

| | RARalpha Kdapp (nM) | RARbeta Kdapp (nM) | RARgamma Kdapp (nM) |
|---|---|---|---|
| Compound of Example 3 | 30 | 8 | 2 |
| Compound of Example 5 | 8 | 8 | 0.5 |
| Compound of Example 6 | 60 | 8 | 0.25 |
| Compound of Example 8 | 60 | 4 | 0.12 |
| Compound of Example 12 | 250 | 4 | 2 |
| Compound of Example 13 | 500 | 4 | 0.5 |
| Compound of Example 17 | 250 | 8 | 30 |
| Compound of Example 19 | 60 | 4 | 1 |
| Compound of Example 21 | 4 | 4 | 30 |
| Compound of Example 23 | 60 | 8 | 2 |
| Compound of Example 25 | 500 | 15 | 2 |
| Compound of Example 33 | 60 | 8 | 0.5 |
| Compound of Example 35 | 4000 | 500 | 8 |
| Compound of Example 37 | 250 | 120 | 30 |
| Compound of Example 47 | 120 | 250 | 120 |
| Compound of Example 52 | 30 | 2 | 0.25 |
| Compound of Example 53 | 2000 | 8000 | 60 |
| Compound of Example 54 | 8 | 4 | 0.25 |

The results obtained with the compounds according to the invention clearly show Kdapp values of less than or equal to 1000 nM.

Example 56

Formulation Examples

This example illustrates various specific formulations based on the compounds according to the invention.

A—Oral Route:

(a) 0.2 g tablet:

| | |
|---|---|
| Compound of Example 5 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable Suspension in 5 ml Ampoules:

| | |
|---|---|
| Compound of Example 3 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavouring | qs |
| Purified water | qs 5 ml |

(c) 0.8 g tablet:

| | |
|---|---|
| Compound of Example 4 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable Suspension in 10 ml Ampoules:

| | |
|---|---|
| Compound of Example 2 | 0.200 g |
| Glycerol | 1.000 g |

-continued

| | |
|---|---|
| 70% sorbitol | 1.000 g |
| Sodium saccharinate | 0.010 g |
| Methyl para-hydroxybenzoate | 0.080 g |
| Flavoring | qs |
| Purified water | qs 10 ml |

B—Parenteral Route:
(a) Composition:

| | |
|---|---|
| Compound of Example 3 | 0.002 g |
| Ethyl oleate | qs 10 g |

(b) Composition:

| | |
|---|---|
| Compound of Example 1 | 0.05% |
| Polyethylene glycol | 20% |
| 0.9% NaCl solution | qs 100 |

(c) Composition:

| | |
|---|---|
| Compound of Example 3 | 2.5% |
| Polyethylene glycol 400 | 20% |
| 0.9% NaCl solution | qs 100 |

(d) Injectable Cyclodextrin Composition:

| | |
|---|---|
| Compound of Example 3 | 0.1 mg |
| β-Cyclodextrin | 0.10 g |
| Water for injection | qs 10.00 g |

C—Topical Route:
(a) Ointment:

| | |
|---|---|
| Compound of Example 2 | 0.020 g |
| Isopropyl myristate | 81.700 g |
| Liquid petroleum jelly oil | 9.100 g |
| Silica ("Aerosil 200" marketed by Degussa) | 9.180 g |

(b) Ointment:

| | |
|---|---|
| Compound of Example 5 | 0.300 g |
| White petroleum jelly codex | qs 100 g |

(c) Nonionic Water-in-Oil Cream:

| | |
|---|---|
| Compound of Example 4 | 0.100 g |
| Mixture of emulsifying lanolin alcohols, waxes and oils ("Anhydrous Eucerin" marketed by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion:

| | |
|---|---|
| Compound of Example 2 | 0.100 g |
| Polyethylene glycol (PEG 400) | 69.900 g |
| 95% ethanol | 30.000 g |

(e) Hydrophobic Ointment:

| | |
|---|---|
| Compound of Example 4 | 0.300 g |
| Isopropyl myristate | 36.400 g |
| Silicone oil ("Rhodorsil 47 V 300" marketed by Rhône-Poulenc) | 36.400 g |
| Beeswax | 13.600 g |
| Silicone oil ("Abil 300 000 cSt" marketed by Goldschmidt) | qs 100 g |

(f) Nonionic Oil-in-Water Cream:

| | |
|---|---|
| Compound of Example 5 | 1.000 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:
1. A method for activating RARγ receptors, said method comprising contacting said receptors with a RARγ receptor activating amount of at least one ligand compound having the formula (I) below:

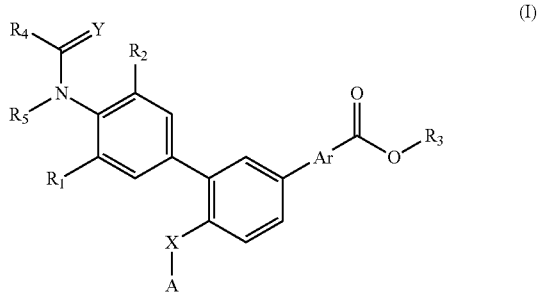

in which:
$R_1$ is a hydrogen atom, an alkyl radical of 1 to 4 carbon atoms or a —$CF_3$ radical;
$R_2$ is a hydrogen atom, an alkyl or alkoxy radical of 1 to 4 carbon atoms or a chlorine atom;

R₃ is a hydrogen atom or a linear or branched alkyl or alkoxy radical of 1 to 10 carbon atoms optionally substituted with a methoxy group;

R₄ is a hydrogen atom or an alkyl radical of 1 to 3 carbon atoms;

R₅ is a hydrogen atom or an alkyl radical of 1 to 3 carbon atoms;

or alternatively R₄ and R₅ form, together with the bond —N—C(=Y)—, a pyrrolidine, pyrrolidinone, piperidine or piperidinone ring;

Y is two hydrogen atoms or a hetero atom;

Ar is a 1,4-phenyl, 2,5-pyridyl, 5,2-pyridyl or 2,5-thiophenyl ring;

X is an oxygen atom optionally substituted with an alkyl or alkylamine radical or a C—C single bond;

A is a hydrogen atom or the following formula:

in which,

Q is an oxygen atom or an —NH— bond;

R₆ is a hydrogen atom, an alkyl radical of 1 to 6 carbon atoms, a cycloalkyl radical of 3 to 6 carbon atoms or a —C(O)CH₃ or —C(O)CH₂CH₃ radical;

R₇ and R₇' represent, independently of each other, a hydrogen atom or a hydroxyl group, with the proviso that R₇ and R₇' are not simultaneously a hydroxyl group;

n is 0, 1, 2, 3, 4 or 5;

or a salt of a compound of formula (I) when R₃ is a hydrogen atom, or a geometrical isomer of a compound of formula (I).

2. The method as defined by claim 1, wherein, in formula (I), R₁ is a —CF₃ radical.

3. The method as defined by claim 1, wherein, in formula (I), Ar is a 1,4-phenyl ring.

4. The method as defined by claim 1, wherein, in formula (I), Ar is a 2,5-pyridyl ring.

5. The method as defined by claim 1, wherein, in formula (I), Ar is a 5,2-pyridyl ring.

6. The method as defined by claim 1, wherein, in formula (I), Ar is a 2,5-thiophenyl ring.

7. The method as defined by claim 1, wherein, in formula (I), Y is oxygen.

8. The method as defined by claim 1, wherein, in formula (I), Y is sulfur.

9. The method as defined by claim 1, wherein, in formula (I), R₄ and R₅ together form, with the —N—C(=Y)-radical, a pyrrolidine, pyrrolidinone, piperidine or piperidinone ring.

10. The method as defined by claim 1, wherein the compound is an alkali metal or alkaline-earth metal salt, a zinc salt or a salt of an organic amine or of an acidic partner when the compound is itself basic.

11. The method as defined by claim 1, wherein the alkyl radical of 1 to 3 carbon atoms is selected from the group consisting of methyl, ethyl, i-propyl and n-propyl radicals.

12. The method as defined by claim 1, wherein the alkyl radical of 1 to 4 carbon atoms is selected from the group consisting of methyl, ethyl, i-propyl, i-butyl and t-butyl radicals.

13. The method as defined by claim 1, wherein the alkyl radical of 1 to 10 carbon atoms is selected from the group consisting of methyl, ethyl, propyl, i-propyl, butyl, i-butyl, t-butyl, pentyl, hexyl, heptyl, octyl, nonyl and dodecyl radicals.

14. The method as defined by claim 1, wherein the alkoxy radical having from 1 to 10 carbon atoms is selected from the group consisting of methoxy, ethoxy, isopropyloxy, tert-butoxy and hexyloxy radicals.

15. The method as defined by claim 1, wherein the alkoxy radical having from 1 to 4 carbon atoms is selected from the group consisting of methoxy, ethoxy, isopropyloxy and tert-butoxy radicals.

16. The method as defined by claim 1, wherein the cycloalkyl radical of 3 to 6 carbon atoms is selected from the group consisting of cyclopropyl, cyclopentyl and cyclohexyl radicals.

17. The method as defined by claim 1, wherein the ligand compound having formula (I) is selected from the group consisting of:

ethyl 3"-tert-butyl-4"-diethylamino-4'-hydroxy[1,1';3',1"]terphenyl-4-carboxylate, ethyl 3"-tert-butyl-4"-diethylamino-4'-(4-hydroxybutoxy)-[1,1';3',1"]terphenyl-4-carboxylate, 3"-tert-butyl-4"-diethylamino-4'-(4-hydroxybutoxy)-[1,1';3',1"]terphenyl-4-carboxylic acid, ethyl 4"-(acetylethylamino)-3"-tert-butyl-4'-(4-hydroxybutoxy)-[1,1';3',1"]terphenyl-4-carboxylate, 4"-(acetylethylamino)-3"-tert-butyl-4'-(4-hydroxybutoxy)-[1,1';3',1"]terphenyl-4-carboxylic acid, 3"-tert-butyl-4"-diethylamino-4'-(2-hydroxyethoxy)-[1,1';3',1"]terphenyl-4-carboxylic acid, ethyl 3"-tert-butyl-4"-diethylamino-4'-(3-hydroxypropoxy)-[1,1';3',1"]terphenyl-4-carboxylate, 3"-tert-butyl-4"-diethylamino-4'-(3-hydroxypropoxy)-[1,1';3',1"]terphenyl-4-carboxylic acid, ethyl 4"-diethylamino-4'-(3-hydroxypropoxy)-[1,1';3',1"]terphenyl-4-carboxylate, 4"-diethylamino-4'-(3-hydroxypropoxy)-[1,1';3',1"]terphenyl-4-carboxylic acid, ethyl 4"-diethylamino-3"-ethyl-4'-(3-hydroxypropoxy)-[1,1';3',1"]terphenyl-4-carboxylate, 4"-diethylamino-3"-ethyl-4'-(3-hydroxypropoxy)-[1,1';3',1"]terphenyl-4-carboxylic acid, 4"-diethylamino-3"-ethyl-4'-(2-hydroxyethoxy)-[1,1';3',1"]terphenyl-4-carboxylic acid, ethyl 4"-diethylamino-3"-ethyl-4'-(2-hydroxyethoxy)-[1,1';3',1"]terphenyl-4-carboxylate, ethyl 3"-tert-butyl-4"-diethylamino-4'-(2-hydroxyethoxy)-[1,1';3',1"]terphenyl-4-carboxylate, ethyl 4"-diethylamino-4'-(3-hydroxypropoxy)-3"-methyl[1,1';3',1"]terphenyl-4-carboxylate, 4"-diethylamino-4'-(3-hydroxypropoxy)-3"-methyl[1,1';3',1"]terphenyl-4-carboxylic acid, ethyl 3"-tert-butyl-4'-(4-hydroxybutoxy)-4"-pyrrolidin-1-yl[1,1';3',1"]terphenyl-4-carboxylate, 3"-tert-butyl-4'-(4-hydroxybutoxy)-4"-pyrrolidin-1-yl[1,1';3',1"]terphenyl-4-carboxylic acid, ethyl 4'-(4-hydroxybutoxy)-4"-pyrrolidin-1-yl-3"-trifluoromethyl[1,1';3',1"]terphenyl-4-carboxylate, 4'-(4-hydroxybutoxy)-4"-pyrrolidin-1-yl-3"-trifluoromethyl[1,1';3',1"]terphenyl-4-carboxylic acid, ethyl 3"-tert-butyl-4'-(3-hydroxypropoxy)-4"-pyrrolidin-1-yl[1,1';3',1"]terphenyl-4-carboxylate, 3"-tert-butyl-4'-(3-hydroxypropoxy)-4"-pyrrolidin-1-yl[1,1';3',1"]terphenyl-4-carboxylic acid, ethyl 3"-tert-butyl-4'-(2-hydroxyethoxy)-4"-pyrrolidin-1-yl[1,1';3',1"]terphenyl-4-carboxylate,
3"-tert-butyl-4'-(2-hydroxyethoxy)-4"-pyrrolidin-1-yl[1,1';3',1"]terphenyl-4-carboxylic acid,
4'-(3-hydroxypropoxy)-4"-pyrrolidin-1-yl[1,1';3',1"]terphenyl-4-carboxylic acid,
3"-tert-butyl-4"-diethylamino-4'-hydroxy[1,1';3',1"]terphenyl-4-carboxylic acid,
ethyl 4"-diethylamino-4'-hydroxy-3"-trifluoromethyl[1,1';3',1"]terphenyl-4-carboxylate,
4"-diethylamino-4'-hydroxy-3"-trifluoromethyl[1,1';3',1"]terphenyl-4-carboxylic acid,
3"-tert-butyl-4"-diethylamino-4'-(4-isopropylaminobutoxy)-[1,1';3',1"]terphenyl-4-carboxylic acid,
3"-tert-butyl-4'-(4-isopropylaminobutoxy)-4"-pyrrolidin-1-yl[1,1';3',1"]terphenyl-4-carboxylic acid,
ethyl 3"-tert-butyl-4"-diethylamino-4'-(3-hydroxypropyl)-[1,1';3',1"]terphenyl-4-carboxylate,
3"-tert-butyl-4"-diethylamino-4'-(3-hydroxypropyl)-[1,1';3',1"]terphenyl-4-carboxylic acid,
ethyl 3"-tert-butyl-4"-diethylamino-4'-(2,3-dihydroxypropyl)-[1,1';3',1"]terphenyl-4-carboxylate,
3"-tert-butyl-4"-diethylamino-4'-(2,3-dihydroxypropyl)-[1,1';3',1"]terphenyl-4-carboxylic acid,
ethyl 4"-(acetylethylamino)-3"-tert-butyl-4'-(3-hydroxypropyl)-[1,1';3',1"]terphenyl-4-carboxylate,
4"-(acetylethylamino)-3"-tert-butyl-4'-(3-hydroxypropyl)-[1,1';3',1"]terphenyl-4-carboxylic acid,
ethyl 3"-tert-butyl-4'-(3-cyclopropylaminopropyl)-4"-diethylamino[1,1';3',1"]terphenyl-4-carboxylate,
3"-tert-butyl-4'-(3-cyclopropylaminopropyl)-4"-diethylamino[1,1';3',1"]terphenyl-4-carboxylic acid,
ethyl 3"-tert-butyl-4'-(3-cyclopentylaminopropyl)-4"-diethylamino[1,1';3',1"]terphenyl-4-carboxylate,
3"-tert-butyl-4'-(3-cyclopentylaminopropyl)-4"-diethylamino[1,1';3',1"]terphenyl-4-carboxylic acid,
ethyl 3"-tert-butyl-4'-(3-cyclohexylaminopropyl)-4"-diethylamino[1,1';3',1"]terphenyl-4-carboxylate,
3"-tert-butyl-4'-(3-cyclohexylaminopropyl)-4"-diethylamino[1,1';3',1"]terphenyl-4-carboxylic acid,
ethyl 3"-tert-butyl-4'-(3-tert-butylaminopropyl)-4"-diethylamino[1,1';3',1"]terphenyl-4-carboxylate,
3"-tert-butyl-4'-(3-tert-butylaminopropyl)-4"-diethylamino[1,1';3',1"]terphenyl-4-carboxylic acid,
ethyl 4"-(acetylethylamino)-3"-tert-butyl-4'-(3-cyclopropylaminopropyl)-[1,1';3',1"]terphenyl-4-carboxylate,
4"-(acetylethylamino)-3"-tert-butyl-4'-(3-cyclopropylaminopropyl)-[1,1';3',1"]terphenyl-4-carboxylic acid,
ethyl 3"-tert-butyl-4"-diethylamino-4'-(3-isopropylaminopropyl)-[1,1';3',1"]terphenyl-4-carboxylate,
3"-tert-butyl-4"-diethylamino-4'-(3-isopropylaminopropyl)-[1,1';3',1"]terphenyl-4-carboxylic acid,
ethyl 4'-(3-aminopropyl)-3"-tert-butyl-4"-diethylamino[1,1';3',1"]terphenyl-4-carboxylate,
4'-(3-aminopropyl)-3"-tert-butyl-4"-diethylamino[1,1';3',1"]terphenyl-4-carboxylic acid,
[3"-tert-butyl-4-carboxy-4'-(3-hydroxypropyl)-[1,1';3',1"]terphenyl-4"-yl]diethylamine hydrochloride,
3"-tert-butyl-4'-(2-hydroxyethoxy)-4"-(2-oxopyrrolidin-1-yl)-[1,1';3',1"]terphenyl-4-carboxylic acid,
3"-tert-butyl-4"-ethylamino-4'-(3-hydroxypropoxy)-[1,1';3',1"]terphenyl-4-carboxylic acid,
4'-(3-acetoxypropoxy)-3"-tert-butyl-4"-diethylamino[1,1';3',1"]terphenyl-4-carboxylic acid,
3"-tert-butyl-4"-diethylamino-4'-(3-propionyloxypropoxy)-[1,1';3',1"]terphenyl-4-carboxylic acid,
methyl 3"-tert-butyl-4"-diethylamino-4'-(3-hydroxypropoxy)-[1,1';3',1"]terphenyl-4-carboxylate,
isopropyl 3"-tert-butyl-4"-diethylamino-4'-(3-hydroxypropoxy)-[1,1';3',1"]terphenyl-4-carboxylate,
isobutyl 3"-tert-butyl-4"-diethylamino-4'-(3-hydroxypropoxy)-[1,1';3',1"]terphenyl-4-carboxylate,
3"-tert-butyl-4"-diethylamino-4'-(3-hydroxypropoxy)-5"-methyl[1,1';3',1"]terphenyl-4-carboxylic acid,
4"-diethylamino-4'-(3-hydroxypropoxy)-3"-isopropyl-5"-methyl[1,1';3',1"]terphenyl-4-carboxylic acid,
3"-tert-butyl-5"-chloro-4"-diethylamino-4'-(3-hydroxypropoxy)-[1,1';3',1"]terphenyl-4-carboxylic acid,
4"-diethylamino-4'-(3-hydroxypropoxy)-3",5"-diisopropyl[1,1';3',1"]terphenyl-4-carboxylic acid,
3",5"-di-tert-butyl-4"-diethylamino-4'-(3-hydroxypropoxy)-[1,1';3',1"]terphenyl-4-carboxylic acid,
4"-diethylamino-4'-(3-hydroxypropoxy)-3"-trifluoromethyl[1,1';3',1"]terphenyl-4-carboxylic acid,
3"-tert-butyl-4"-(ethylmethylamino)-4'-(2-hydroxyethoxy)-[1,1';3',1"]terphenyl-4-carboxylic acid,
3"-tert-butyl-4"-dimethylamino-4'-(2-hydroxyethoxy)-[1,1';3',1"]terphenyl-4-carboxylic acid,
3"-tert-butyl-4"-(ethylisopropylamino)-4'-(2-hydroxyethoxy)-[1,1';3',1"]terphenyl-4-carboxylic acid,
3"-tert-butyl-4"-(ethylpropylamino)-4'-(2-hydroxyethoxy)-[1,1';3',1"]terphenyl-4-carboxylic acid,
3"-tert-butyl-4"-dipropylamino-4'-(2-hydroxyethoxy)-[1,1';3',1"]terphenyl-4-carboxylic acid,
3"-tert-butyl-4"-(ethylpropionylamino)-4'-(2-hydroxyethoxy)-[1,1';3',1"]terphenyl-4-carboxylic acid,
6-[3'-tert-butyl-4'-diethylamino-6-(2-hydroxyethoxy)biphenyl-3-yl]nicotinic acid,
5-[3'-tert-butyl-4'-diethylamino-6-(2-hydroxyethoxy)biphenyl-3-yl]pyridine-2-carboxylic acid,
5-[3'-tert-butyl-4'-diethylamino-6-(2-hydroxyethoxy)biphenyl-3-yl]thiophene-2-carboxylic acid,
3"-tert-butyl-4'-(2-hydroxyethoxy)-5"-methyl-4"-pyrrolidin-1-yl[1,1';3',1"]terphenyl-4-carboxylic acid,
3"-tert-butyl-5"-chloro-4'-(2-hydroxyethoxy)-4"-pyrrolidin-1-yl[1,1';3',1"]terphenyl-4-carboxylic acid,
4'-(2-hydroxyethoxy)-3"-isopropyl-4"-pyrrolidin-1-yl[1,1';3',1"]terphenyl-4-carboxylic acid,
3"-ethyl-4'-(2-hydroxyethoxy)-4"-pyrrolidin-1-yl[1,1';3',1"]terphenyl-4-carboxylic acid,
4'-(2-hydroxyethoxy)-3",5"-diisopropyl-4"-pyrrolidin-1-yl[1,1';3',1"]terphenyl-4-carboxylic acid,
3",5"-diethyl-4'-(2-hydroxyethoxy)-4"-pyrrolidin-1-yl[1,1';3',1"]terphenyl-4-carboxylic acid,
3",5"-dimethyl-4'-(2-hydroxyethoxy)-4"-pyrrolidin-1-yl[1,1';3',1"]terphenyl-4-carboxylic acid,
4'-(2-acetoxyethoxy)-3"-tert-butyl-4"-pyrrolidin-1-yl[1,1';3',1"]terphenyl-4-carboxylic acid,
4'-(2-propionyloxyethoxy)-3"-tert-butyl-4"-pyrrolidin-1-yl[1,1';3',1"]terphenyl-4-carboxylic acid,
methyl 3"-tert-butyl-4'-(2-hydroxyethoxy)-4"-pyrrolidin-1-yl[1,1';3',1"]terphenyl-4-carboxylate,
isopropyl 3"-tert-butyl-4'-(2-hydroxyethoxy)-4"-pyrrolidin-1-yl[1,1';3',1"]terphenyl-4-carboxylate,
isobutyl 3"-tert-butyl-4'-(2-hydroxyethoxy)-4"-pyrrolidin-1-yl[1,1';3',1"]terphenyl-4-carboxylate,
ethyl 3"-tert-butyl-4'-(3-hydroxypropoxy)-4"-pyrrolidin-1-yl[1,1';3',1"]terphenyl-4-carboxylate,
ethyl 3"-tert-butyl-5"-chloro-4'-(2-hydroxyethoxy)-4"-pyrrolidin-1-yl[1,1';3',1"]terphenyl-4-carboxylate,
6-[3'-tert-butyl-6-(2-hydroxyethoxy)-4'-pyrrolidin-1-ylbiphenyl-3-yl]nicotinic acid, 5-[3'-tert-butyl-6-(2-hydroxyethoxy)-4'-pyrrolidin-1-ylbiphenyl-3-yl]pyridine-2-carboxylic acid,
ethyl 6-[3'-tert-butyl-6-(2-hydroxyethoxy)-4'-pyrrolidin-1-ylbiphenyl-3-yl]nicotinate,
ethyl 3"-tert-butyl-4'-(3-hydroxypropyl)-4"-pyrrolidin-1-yl[1,1';3',1"]terphenyl-4-carboxylate,
3"-tert-butyl-4'-(3-hydroxypropyl)-4"-pyrrolidin-1-yl[1,1';3',1"]terphenyl-4-carboxylic acid,
3"-tert-butyl-4'-(2-hydroxyethoxy)-4"-(2-oxopyrrolidin-1-yl)-[1,1';3',1"]terphenyl-4-carboxylic acid,
3"-tert-butyl-4'-(2-hydroxyethoxy)-4"-(2-oxopiperid-1-yl)-[1,1';3',1"]terphenyl-4-carboxylic acid,
3"-tert-butyl-4'-(2-hydroxyethoxy)-4"-piperid-1-yl[1,1';3',1"]terphenyl-4-carboxylic acid, and
5-[3'-tert-butyl-6-(2-hydroxyethoxy)-4'-pyrrolidin-1-ylbiphenyl-3-yl]thiophene-2-carboxylic acid.

18. The method as defined by claim 1, wherein, in formula (I), at least one of the following conditions is satisfied:
$R_1$ is a hydrogen atom or a t-butyl or i-propyl radical;
$R_2$ is a hydrogen atom or a t-butyl or i-propyl radical;
$R_3$ is a hydrogen atom or an ethyl radical;
$R_4$ and $R_5$ are, independently of each other, a methyl or ethyl radical or together form a pyrrolidine ring;
A is as defined in which $R_6$ is a hydrogen atom, an i-propyl or t-butyl radical, a cycloalkyl radical of 3 to 6 carbon atoms or a —C(O)CH$_3$ or —C(O)CH$_2$CH$_3$ radical.

19. The method as defined by claim 18, wherein, in formula (I), all of the following conditions are satisfied:
$R_1$ is a hydrogen atom or a t-butyl or i-propyl radical;
$R_2$ is a hydrogen atom or a t-butyl or i-propyl radical;
$R_3$ is a hydrogen atom or an ethyl radical;
$R_4$ and $R_5$ are, independently of each other, a methyl or ethyl radical or together form a pyrrolidine ring;
A is as defined in which $R_6$ is a hydrogen atom, an i-propyl or t-butyl radical, a cycloalkyl radical of 3 to 6 carbon atoms or a —C(O)CH$_3$ or —C(O)CH$_2$CH$_3$ radical.

20. The method as defined by claim 1, wherein the ligand compound having formula (I) is selected from the group consisting of:
3"-tert-butyl-4"-diethylamino-4'-(4-hydroxybutoxy)-[1,1';3',1"]terphenyl-4-carboxylic acid,
4"-(acetylethylamino)-3"-tert-butyl-4'-(4-hydroxybutoxy)-[1,1';3',1"]terphenyl-4-carboxylic acid,
3"-tert-butyl-4"-diethylamino-4'-(2-hydroxyethoxy)-[1,1';3',1"]terphenyl-4-carboxylic acid,
3"-tert-butyl-4"-diethylamino-4'-(3-hydroxypropoxy)-[1,1';3',1"]terphenyl-4-carboxylic acid,
4"-diethylamino-3"-ethyl-4'-(3-hydroxypropoxy)-[1,1';3',1"]terphenyl-4-carboxylic acid,
4"-diethylamino-3"-ethyl-4'-(2-hydroxyethoxy)-[1,1';3',1"]terphenyl-4-carboxylic acid,
4"-diethylamino-4'-(3-hydroxypropoxy)-3"-methyl[1,1';3',1"]terphenyl-4-carboxylic acid,
3"-tert-butyl-4'-(4-hydroxybutoxy)-4"-pyrrolidin-1-yl[1,1';3',1"]terphenyl-4-carboxylic acid,
4'-(4-hydroxybutoxy)-4"-pyrrolidin-1-yl-3"-trifluoromethyl[1,1';3',1"]terphenyl-4-carboxylic acid,
3"-tert-butyl-4'-(3-hydroxypropoxy)-4"-pyrrolidin-1-yl[1,1';3',1"]terphenyl-4-carboxylic acid,
3"-tert-butyl-4'-(2-hydroxyethoxy)-4"-pyrrolidin-1-yl[1,1';3',1"]terphenyl-4-carboxylic acid,
3"-tert-butyl-4"-diethylamino-4'-(3-hydroxypropyl)-[1,1';3',1"]terphenyl-4-carboxylic acid,
3"-tert-butyl-4"-diethylamino-4'-(2,3-dihydroxypropyl)-[1,1';3',1"]terphenyl-4-carboxylic acid,
4"-(acetylethylamino)-3"-tert-butyl-4'-(3-hydroxypropyl)-[1,1';3',1"]terphenyl-4-carboxylic acid,
4"-(acetylethylamino)-3"-tert-butyl-4'-(3-cyclopropylaminopropyl)-[1,1';3',1"]terphenyl-4-carboxylic acid,
[3"-tert-butyl-4-carboxy-4'-(3-hydroxypropyl)-[1,1';3',1"]terphenyl-4"-yl]diethylamine hydrochloride,
3"-tert-butyl-4'-(2-hydroxyethoxy)-4"-(2-oxopyrrolidin-1-yl)-[1,1';3',1"]terphenyl-4-carboxylic acid, and
3"-tert-butyl-4"-ethylamino-4'-(3-hydroxypropoxy)-[1,1';3',1]terphenyl-4-carboxylic acid.

21. The method as defined by claim 1, wherein the ligand compound having formula (I) is 3"-tert-butyl-4'-(2-hydroxyethoxy)-4"-pyrrolidin-1-yl[1,1';3',1"]terphenyl-4-carboxylic acid.

* * * * *